US006357163B1

(12) United States Patent
Buchardt et al.

(10) Patent No.: US 6,357,163 B1
(45) Date of Patent: Mar. 19, 2002

(54) USE OF NUCLEIC ACID ANALOGUES IN DIAGNOSTICS AND ANALYTICAL PROCEDURES

(76) Inventors: Ole Buchardt, Søndergardsvej 73, 3500 Værløse; Michael Egholm, Sindshvilevej 5, 3. tv., 2000 Fredericksberg; Peter E. Nielsen, Hjortevaenget 509, 2980 Kokkedal; Rolf H. Berg, Langelandsvej 20 B, 3. th., 2000 Fredericksberg, all of (DK)

( * ) Notice: Subject to any disclaimer, the term of this patent is extended or adjusted under 35 U.S.C. 154(b) by 0 days.

(21) Appl. No.: 08/150,156
(22) PCT Filed: May 22, 1992
(86) PCT No.: PCT/EP92/01220
  § 371 Date: May 4, 1994
  § 102(e) Date: May 4, 1994
(87) PCT Pub. No.: WO92/20703
  PCT Pub. Date: Nov. 26, 1992

(30) Foreign Application Priority Data

May 24, 1991 (DK) .............................................. 0986/91
May 24, 1991 (DK) .............................................. 0987/91
Apr. 15, 1992 (DK) .............................................. 0510/92

(51) Int. Cl.$^7$ .......................... C12Q 1/68; C07H 21/02; C07H 21/04
(52) U.S. Cl. .......................... 43/6; 536/23.1; 536/24.3; 536/22.1
(58) Field of Search .............................. 435/6; 536/24.5, 536/22.1, 23.1, 29

(56) References Cited

U.S. PATENT DOCUMENTS

| 4,820,812 A |   | 4/1989 | Miyoshi et al. |
| 5,034,506 A | * | 7/1991 | Summerton et al. |
| 5,539,082 A | * | 7/1996 | Nielsen et al. |

FOREIGN PATENT DOCUMENTS

| DK | 2910129 |   | 5/1991 |
| DK | 2910130 |   | 5/1991 |
| WO | 8605518 |   | 9/1986 |
| WO | WO 86/05519 | * | 9/1986 |
| WO | 8903849 |   | 5/1989 |
| WO | 8912060 |   | 12/1989 |
| WO | 9002749 |   | 3/1990 |
| WO | 9220702 |   | 11/1992 |
| WO | 9312129 |   | 6/1993 |

OTHER PUBLICATIONS

The Stratagene Catalog, p. 39 (1988).*
Matthews et al., Analytical Biochemistry 169: 1–25 (1988).*
Goldberg et al., Methods in Enzymology 68: 206–220, 1979.*
Bergstrom et al. J. Org. Chem. 57(3):873–876(1992).*
Mitchell et al. Nucleic Acids Research 18(17): 5321(1990).*
Caruthers, "Antisense Inhibitors of Gene Expression", pp. 7–24, J.S. Cohen ed., CRC Press Boca Raton, FL (1989).*
Parkanyi et al., "Synthesis of Polymethylene Chain–Bridged 6–Substituted 8–Arapurines and Related Compounds", Collect. Czech. Chem. Commun., 1991, vol. 56, p. 2382–2388.
Shvachkin et al., "Advances in Chemistry", 1982, vol. 2, 311–331.
Pitha et al. "Synthetic Analogs of Nucleic Acids", Biomedical Polymers Polymeric Material and Pharmaceuticals For Biomedical Use, Academic Press, 1980, p. 271–297.
Takemoto, "Recent Problems Concerning Functional Monomers and Polymers Containing Nucleic Acid Bases" Polymeric Drugs, Acad. Press, 1978, p. 103–129.
Akashi, M. and Takamoto, K. "New Aspects of Polymer Drugs", Adv. Polym. Sci., 1990, 97, 108–146.
D.P. Mack et al. "Design and Chemical Synthesis of a Sequence–Specific DNA–Cleaving Protein", J. Amer. Chem. Soc. 1988, 110, 7572–7574.
Buttrey, J.D., et al. "Synthetic Analogues of Polynucleotides–XIII, The Resolution of DL–β–(Thymine–1–YL) Alanine and Polymerisation of the β–(Thymine–1–YL) Alamines", Tetrahedron 1975, 31, 73–75.
De Koning, H., et al. "Unconventional Nucleotide Analogues V. Derivatives of 6–(1–pyrimidinyl)–and 6–(9–purinyl) –2–aminocaproic acids.", Recueil, 1971, 90, 874–884.
Doel, M.T., et al. "An Approach to the Synthesis of Peptide Analogues of Oligonucleotides (Nucleopeptides)", Tetrahedron Letters, 1969, 27, 2285–2288.
Doel, M.T., et al. "The Synthesis of Peptides Containing Purine and Pyrimidine Derivatives of DL–Alanine", Tetrahedron, 1974, 30, 2755–2759.
Hanvey, J.C., et al. "Antisense and Antigene Properties of Peptide Nucleic Acids", Science 1992, 258, 1481–1485.

(List continued on next page.)

*Primary Examiner*—Ethan C. Whisenant
(74) *Attorney, Agent, or Firm*—Pillsbury Winthrop LLP

(57) ABSTRACT

Methods of capture, recognition, detection, identification or quantitation of nucleic acids and diagnostics uses generally are described in which are used: (a) a peptide nucleic acid (PNA) comprising a polyamide backbone bearing a plurality of ligands at respective spaced locations along said backbone, said ligands being each independently naturally occurring nucleobases, non-naturally occurring nucleobases or nucleobase-binding groups, each said ligand being bound directly or indirectly to a nitrogen atom in said backbone, and said ligand bearing nitrogen atoms mainly being separated from one another in said backbone by from 4 to 8 intervening atoms; or (b) a nucleic acid analogue capable of hybridizing to a nucleic acid of complementary sequence to form a hybrid which is more stable against denaturation by heat than a hybrid between the conventional deoxyribonucleotide corresponding to said analogue and said nucleic acid; or (c) a nucleic acid analogue capable of hybridizing to a double stranded nucleic acid in which one strand has a sequence complementary to said analogue, so as to displace the other strand from said one strand.

15 Claims, 33 Drawing Sheets

OTHER PUBLICATIONS

Huang, S., et al. "Acyclic Nuclei Acid Analogues: Synthesis and Oligomerization of γ,4–Diamino–2–oxo–1(2H)–pyrimidinepentanoic Acid and σ 4–Diamino–2–oxo–12(2HO–pyrimidinehexanoic Acid", J. Or. Chem., 1991, 56,6007–6018.

Inaki, et al. K. "Functionality and Applicability of Synthetic Nucleic Acid Analogs", In Current Topics in Polymer Science; Ottenbrite, Utracki, Inoue, Eds. Munich; New York. 1:80–100.

Inaki, Y. "Synthetic Nuclei Analogs", Prog. Polym. Sci. 1992, 17, 515–570.

Lu, et al., Synthesis of Polyesters Containing Nucleic Acid Base Derivatives as Pending Side Chains: J. Polym. Sci.: Part A: Polymer Chemistry 1986, 24, 525–36.

Nagae, S., et al. Functional Monomers and Polymers. CLIV. Application of Nucleic Acid Base Containing Polymers to High Performance Liquid Chromatography:, J. Polym. Sci.: Part A:Polymer Chemistry 1989, 27, 2593–2609.

Nollet, A.J.H., et al. "Uncoventional Nucleotide Analogues–III, 4–($N_1$–Pyrimidyl)–2–Aminobutyric Acids", Tetrahedron , 1986, 25, 5989–5994.

Nollet, A.J.H.et al. "Unconventional Nucleotide Analogues–I, $N_9$–Purinyl α–Amino Acids", Tetrahedron, 1969, 25, 5971–5981.

Nollet, A.J.H., et al. "Unconventional Nucleotide Analogues–II, Synthesis of the Adenyl Analogue of Willardine" Tetrahedron, 1969, 25, 5983–5987.

Nollet, A.J.H., et al. "Michael Addition of 4–O–Ethyluracil. A Method for Specific $N_1$–Alkylation of Hydroxpyrimidines", Tetrahedron Letters, 1969, 53, 4605–4606.

Pitha, P.M., t al. "Inhibition of Murine Leukemia Virus Replication by Poly(vinyluracil) and Poly(vinylladenine)" Proc. Natl. Acad. Sci. USA, 1973, 70, 1204–1208.

Pitha, J. "Physiological Activities of Synthetic Analogs of Polynucleotides", Adv. Polym. Sci., 1983, 50, 1–16.

Simon, R.J., et al. "Peptoids: A Modular Approach to Drug Discovery", Proc. Natl. Acad. Sci. USA. 1992, 89, 9367–9371.

P.E. Nielsen et al., "Photochemical Cleavage of DNA by Nitrobenzamides Linked to 9–Aminoacridine", Biochem. 1988, 27, 6338–6343.

Takemoto, K. et al. "Synthetic Nucleic Acid Analogs. Preparation and Interactions", Adv. Polym. Sci., 1981 41, 1–51.

Uhlmann, E., et al. "Antisense Oligonucleotides: A New Therapeutic Principle", Chemical Reviews, 1990, 90, 544–584.

Weller, D.D., et al., "Molecular Modeling of Acyclic Polyamide Oligonucleotide Analogues", J. Org. Chem., 1991, 6000–6006.

Brady, et al., "Large–Scale Synthesis of a Cycli Xa Peptide Analogue of Somatostation" J. Org. Chemistry 52: 764–769 (1987).

P.E. Nielsen et al, "Sequence–Specific Recognition of DNA by Strand Displacement with a Thymine–Substituted Polyamide", Science, 1991, 254, 1497–1500.

E. Egholm et al, "Peptide Nucleic Acids (PNA) Oligonucleotide Analogues with an Achiral Peptide Backbone", J. Amer. Chem. Soc. 1992, 114, 1895–1897.

L.P.G. Wakelin et al, "Kinetic and Equilibrium Binding Studies of Amsacrine–4–Carboxamides: A Class of Asymmetrical DNA–Intercalating Agents Which Bind by Threading Through the DNA Helix", J.Med.Chem.1990, 2039–2044.

* cited by examiner

R¹ = AMINO ACID SIDECHAIN
R² = METHYL, ETHYL ETC.

PNA 1: $T_{10}$  PNA 2: $T_5CT_4$  PNA 3: $T_2CT_2CT_4$

Inhibition of Restriction Enzyme Cleavage by PNA

PNA/DNA    0   0.006   0.02   0.06   0.2   0.6

PvuII — 2364 bp — PvuII

PvuII   BamH1   PvuII

PvuII   BamH1
  211 bp

BamH1   PvuII
  111 bp

PNA Target

5´------GGATCCAAAAAAAAAAGGATCC-------
3´------CCTAGGTTTTTTTTTTCCTAGG-------

BamH1                    BamH1

Binding of $^{125}$I-Tyr-PNA-T$_{10}$ to dA$_{10}$

PNA        - - - + +   - - - + +
           P X B P X   P X B P X
           1 2 3 4 5   6 7 8 9 10
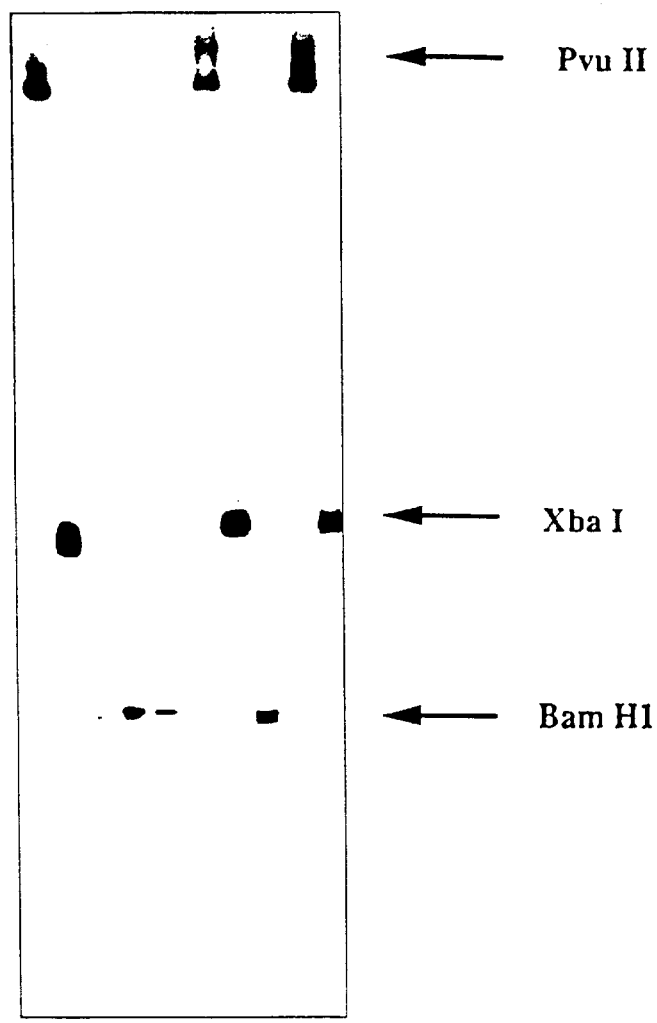
← Pvu II
*FIG. 26*
← Xba I
← Bam H1
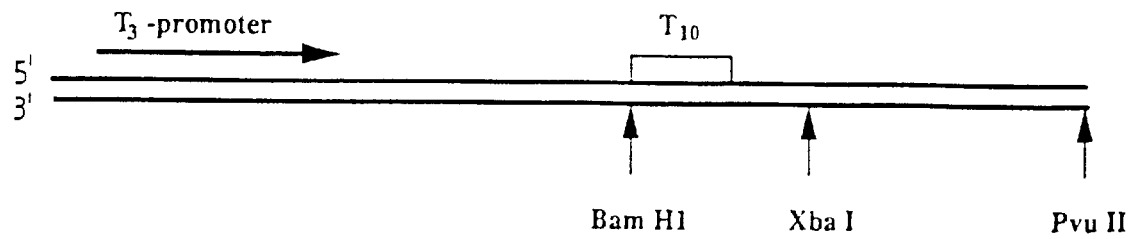

SEQUENCE LISTING

```
(1) GENERAL INFORMATION:

(iii) NUMBER OF SEQUENCES: 40

(2) INFORMATION FOR SEQ ID NO: 1:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
         (H) DOCUMENT NUMBER: WO PCT/EP92/01220
         (I) FILING DATE: 22-MAY-1992

(xi) SEQUENCE DESCRIPTION: SEQ ID NO: 1:

AAAAAAAAAA                                                                10

(2) INFORMATION FOR SEQ ID NO: 2:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

```
    (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 2:

AAAAGAAAAA                                                              10

(2) INFORMATION FOR SEQ ID NO: 3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 3:

AAAACAAAAA                                                              10

(2) INFORMATION FOR SEQ ID NO: 4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 4:

AAAATAAAAA                                                              10

(2) INFORMATION FOR SEQ ID NO: 5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 5:

AAAAAGAAAA                                                              10
```

```
(2) INFORMATION FOR SEQ ID NO: 6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 6:

AAAAACAAAA                                                          10

(2) INFORMATION FOR SEQ ID NO: 7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 7:

AAAAATAAAA                                                          10

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 8:

GATCCAAAAA AAGGATC                                                  17

(2) INFORMATION FOR SEQ ID NO: 9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(iii) HYPOTHETICAL: NO (iv) ANTI-SENSE: NO (x) PUBLICATION INFORMATION:
              (H) DOCUMENT NUMBER: WO PCT/EP92/01220
              (I) FILING DATE: 22-MAY-1992

(xi) SEQUENCE DESCRIPTION: SEQ ID NO: 9:

AAGAAGAAAA                                                                  10

(2) INFORMATION FOR SEQ ID NO: 10:

(i) SEQUENCE CHARACTERISTICS:
              (A) LENGTH: 10 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (x) PUBLICATION INFORMATION:
              (H) DOCUMENT NUMBER: WO PCT/EP92/01220
              (I) FILING DATE: 22-MAY-1992

(xi) SEQUENCE DESCRIPTION: SEQ ID NO: 10:

AAAAAAAAAA                                                                  10

(2) INFORMATION FOR SEQ ID NO: 11:

(i) SEQUENCE CHARACTERISTICS:
              (A) LENGTH: 10 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (x) PUBLICATION INFORMATION:
              (H) DOCUMENT NUMBER: WO PCT/EP92/01220
              (I) FILING DATE: 22-MAY-1992

(xi) SEQUENCE DESCRIPTION: SEQ ID NO: 11:

TTTTTTTTTT                                                                  10

(2) INFORMATION FOR SEQ ID NO: 12:

(i) SEQUENCE CHARACTERISTICS:
              (A) LENGTH: 8 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (x) PUBLICATION INFORMATION:
              (H) DOCUMENT NUMBER: WO PCT/EP92/01220
              (I) FILING DATE: 22-MAY-1992

(xi) SEQUENCE DESCRIPTION: SEQ ID NO: 12:

```
AAAAAAAA                                                         8
```

(2) INFORMATION FOR SEQ ID NO: 13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 13:

```
AAAAGAAGAA                                                       10
```

(2) INFORMATION FOR SEQ ID NO: 14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 14:

```
TTTTCTTTTT                                                       10
```

(2) INFORMATION FOR SEQ ID NO: 15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 15:

```
TTTTCTTCTT                                                       10
```

(2) INFORMATION FOR SEQ ID NO: 16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 16:

TTTTTCTTTT                                                                    10

(2) INFORMATION FOR SEQ ID NO: 17:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 17:

TTTTTCTTCT                                                                    10

(2) INFORMATION FOR SEQ ID NO: 18:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 18:

TTCTTCTTTT                                                                    10

(2) INFORMATION FOR SEQ ID NO: 19:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 19:

TTTTTTTTTT TTTTT                                                    15

(2) INFORMATION FOR SEQ ID NO: 20:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (x) PUBLICATION INFORMATION:
         (H) DOCUMENT NUMBER: WO PCT/EP92/01220
         (I) FILING DATE: 22-MAY-1992

(xi) SEQUENCE DESCRIPTION: SEQ ID NO: 20:

AAAAAAAAAA AAAAA                                                    15

(2) INFORMATION FOR SEQ ID NO: 21:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (x) PUBLICATION INFORMATION:
         (H) DOCUMENT NUMBER: WO PCT/EP92/01220
         (I) FILING DATE: 22-MAY-1992

(xi) SEQUENCE DESCRIPTION: SEQ ID NO: 21:

GATCCAAAAA AAAAAG                                                   16

(2) INFORMATION FOR SEQ ID NO: 22:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (x) PUBLICATION INFORMATION:
         (H) DOCUMENT NUMBER: WO PCT/EP92/01220
         (I) FILING DATE: 22-MAY-1992

(xi) SEQUENCE DESCRIPTION: SEQ ID NO: 22:

GATCCTTTTT TTTTTG                                                   16

(2) INFORMATION FOR SEQ ID NO: 23:

(i) SEQUENCE CHARACTERISTICS:
         (A) LENGTH: 10 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 23:

AAAAGGAGAG                                                                      10

(2) INFORMATION FOR SEQ ID NO: 24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 24:

GAGAGGAAAA                                                                      10

(2) INFORMATION FOR SEQ ID NO: 25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 25:

AAAAGTAGAG                                                                      10

(2) INFORMATION FOR SEQ ID NO: 26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
            (H) DOCUMENT NUMBER: WO PCT/EP92/01220
            (I) FILING DATE: 22-MAY-1992

(xi) SEQUENCE DESCRIPTION: SEQ ID NO: 26:

AAAAGGTGAG                                                                10

(2) INFORMATION FOR SEQ ID NO: 27:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (x) PUBLICATION INFORMATION:
            (H) DOCUMENT NUMBER: WO PCT/EP92/01220
            (I) FILING DATE: 22-MAY-1992

(xi) SEQUENCE DESCRIPTION: SEQ ID NO: 27:

GAGATGAAAA                                                                10

(2) INFORMATION FOR SEQ ID NO: 28:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (x) PUBLICATION INFORMATION:
            (H) DOCUMENT NUMBER: WO PCT/EP92/01220
            (I) FILING DATE: 22-MAY-1992

(xi) SEQUENCE DESCRIPTION: SEQ ID NO: 28:

GAGTGGAAAA                                                                10

(2) INFORMATION FOR SEQ ID NO: 29:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (x) PUBLICATION INFORMATION:
            (H) DOCUMENT NUMBER: WO PCT/EP92/01220
            (I) FILING DATE: 22-MAY-1992

(xi) SEQUENCE DESCRIPTION: SEQ ID NO: 29:

TCGACTTTTC TTTTTG                                                         16

(2) INFORMATION FOR SEQ ID NO: 30:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (x) PUBLICATION INFORMATION:
    (H) DOCUMENT NUMBER: WO PCT/EP92/01220
    (I) FILING DATE: 22-MAY-1992

(xi) SEQUENCE DESCRIPTION: SEQ ID NO: 30:

TCGACAAAAA GAAAAG      16

(2) INFORMATION FOR SEQ ID NO: 31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 31:

GAAGAAGAAA ATGCA      15

(2) INFORMATION FOR SEQ ID NO: 32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 32:

GTTTTCTTCT TCTGCA      16

(2) INFORMATION FOR SEQ ID NO: 33:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 33:

GAAGAAGAAA CTGAC                                                          15

(2) INFORMATION FOR SEQ ID NO: 34:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 34:

GATCACGCGT ATACGCGT                                                       18

(2) INFORMATION FOR SEQ ID NO: 35:

(i) SEQUENCE CHARACTERISTICS:
             (A) LENGTH: 77 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 35:

GATCCGGCAA ATCGGCAATA CGGCATACGG CTAAACGGCT TTACGGCTTA                    50

TCGGCTATTC GGCATTTCGG CAATTCG                                             77

(2) INFORMATION FOR SEQ ID NO: 36:

(i) SEQUENCE CHARACTERISTICS:
             (A) LENGTH: 64 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (H) DOCUMENT NUMBER: WO PCT/EP92/01220
             (I) FILING DATE: 22-MAY-1992

(xi) SEQUENCE DESCRIPTION: SEQ ID NO: 36:

```
GATCCGGCTT AACGGCAATT CGCTTATACG GCATATCGGC TAATCGGCAT            50

TACGGCTTTT CGGG                                                  64
```

(2) INFORMATION FOR SEQ ID NO: 37:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 37:

```
GACAAACATA CAATTTCAAC AGAACCAAAA AAAAAAAAAA                      40
```

(2) INFORMATION FOR SEQ ID NO: 38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 38:

```
ACTGACTACC TAGGTTTACC GTGCCAGTCA                                 30
```

(2) INFORMATION FOR SEQ ID NO: 39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: WO PCT/EP92/01220
        (I) FILING DATE: 22-MAY-1992

(xi) SEQUENCE DESCRIPTION: SEQ ID NO: 39:

```
GAAACGGATA GCTGCA                                                16
```

(2) INFORMATION FOR SEQ ID NO: 40:

(i) SEQUENCE CHARACTERISTICS:
        (A) LENGTH: 22 base pairs

```
       (B) TYPE: nucleic acid
       (C) STRANDEDNESS: double
       (D) TOPOLOGY: linear (ii) MOLECULE TYPE: DNA (genomic)

(x) PUBLICATION INFORMATION:
         (H) DOCUMENT NUMBER: WO PCT/EP92/01220
         (I) FILING DATE: 22-MAY-1992

(xi) SEQUENCE DESCRIPTION: SEQ ID NO: 40:

GGATCCAAAA AAAAAAGGAT CC                                          22
```

USE OF NUCLEIC ACID ANALOGUES IN DIAGNOSTICS AND ANALYTICAL PROCEDURES

The present invention relates to the use of certain nucleic acid analogues in the field of diagnostics, for instance in the capture, recognition, detection, identification or quantitation of one or more chemical or microbiological entities.

Oligodioxyribonucleotides (oligo-DNA's) are finding increasing use in diagnostics procedures. They are for instance finding use in testing for the presence of specific micro-organisms or for testing for the presence of generic predispositions, for instance to disease, in forensic science and in microbiology generally. The uses of oligo-DNA's in this field are of course dependent upon the ability of such oligo-DNA's to hybridise to complementary nucleic acid sequences. By way of example, labelled oligo-DNA probes are used in hybridisation assays to probe immobilised target DNA's for the presence of specific sequences. In amplification procedures, the hybridisation property of oligo-DNA's is utilised to hybridise oligo-DNA primers to template molecules to be amplified.

Oligo-DNA's as long as 100 base pairs in length are now routinely synthesised using a solid support method and fully automatic synthesis machines are commercially available. Attention has nonetheless been given to the possibility of constructing synthetic DNA-analogues capable of hybridising to natural DNA in a sequence specific manner and yet having chemical properties advantageously distinct from DNA itself. This work has been largely motivated by the possible use of such compounds in "anti-sense" therapeutics where the use of conventional oligo-DNA's encounters difficulties because such unmodified oligonucleotides have a short half life in vivo due to the natural presence of nucleases, are difficult and costly to prepare in any quantity and are poor at penetrating cell membranes.

For instance, International (PCT) Patent Application WO86/05518 discloses DNA analogues having a backbone bearing a sequence of ligands, typically nucleotide bases, supposedly capable of sequence specific hybridisation to naturally occurring nucleic acids. A number of different backbone structures are disclosed. No specific exemplification of the provision of such compounds is given and there are no data showing the affinity of the claimed analogues for DNA.

International (PCT) Patent Application WO86/05519 claims diagnostic reagents and systems comprising DNA analogues of the same kind but once again, there is no exemplification.

International (PCT) Patent Application WO89/12060 describes oligonucleotide analogues based on various building blocks from which they are synthesised. Whilst there is exemplification of the building blocks, there is no example of actually preparing an oligonucleotide analogue from them and hence no indication of the performance of the analogues.

Furthermore, it is known to modify the DNA backbone with the aim of increasing resistance to nuclease and generally improving the suitability of the DNA for use in anti-sense therapeutic methods. Other attempts to design DNA analogues are discussed in the introductory portion of WO86/05518 mentioned above.

The universal experience has been that modifications of the backbone of natural DNA lead to a decrease in the stability of the hybrid formed between the modified oligonucleotide and its complementary normal oligonucleotide, assayed by measuring the $T_m$ value. Consequently, the conventional wisdom in this area is that modifications of the backbone always destabilise the hybrid, i.e. result in lower $T_m$ values, and therefore the modification should be as minor as possible in order to obtain hybrids with only a slight decrease in $T_m$ value as the best obtainable result.

The present invention relates to the use in diagnostics or in analysis of nucleic acid analogues of novel structure, preferably having the previously unknown property of forming hybrids with complementary sequence conventional nucleic acids which are more stable in terms of $T_m$ value than would be a similar hybrid formed by a conventional nucleic acid of corresponding sequence and/or exhibiting greater selectively for the complementary sequence compared to sequences involving a degrees of mis-match than would be exhibited by said corresponding conventional nucleic acid of corresponding sequence.

The invention provides a nucleic acid analogue for use in the capture, recognition, detection, identification or quantitation of one or more chemical or microbiological entities, which analogue is (a) a peptide nucleic acid (PNA) comprising a polyamide backbone bearing a plurality of ligands at respective spaced locations along said backbone, said ligands being each independently naturally occurring nucleobases, non-naturally occurring nucleobases or nucleobase-binding groups, each said ligand being bound directly or indirectly to a nitrogen atom in said backbone, and said ligand bearing nitrogen atoms mainly being separated from one another in said backbone by from 4 to 8 intervening atoms.

(b) a nucleic acid analogue capable of hybridising to a nucleic acid of complementary sequence to form a hybrid which is more stable against denaturation by heat than a hybrid between the conventional deoxyribonucleotide corresponding to said analogue and said nucleic acid; or (c) a nucleic acid analogue capable of hybridising to a double stranded nucleic acid in which one strand has a sequence complementary to said analogue, so as to displace the other strand from said one strand.

The separation of the nitrogen bearing atoms in the backbone of nucleic acid analogues defined in paragraph (a) above (PNA's) is preferably by five atoms. In nucleic acid analogues having the Formula I (below) this has been found to provide the strongest affinity for DNA. However, it may in some cases be desired to reduce the strength of binding between the PNA's and DNA by spacing one or more of the ligands by a less than optimal spacing, e.g. by a spacing of more than 5 atoms, e.g. by up to 14 atoms or more.

Preferably not more than 25% of interligand spacings will be 6 atoms or more. More preferably not more than 10 to 15% of interligand spacings will be 6 atoms or more. The aza nitrogen atoms which carry the ligands (directly or via linker groups are not themselves counted in the spacings referred to above.

An alternative or additional method for reducing the strength of DNA binding is to omit certain of the ligands, putting in their place a moiety which contributes little or nothing to the binding of DNA, e.g. hydrogen. Preferably, not more than 25% of the ligand positions will be occupied by non-binding moieties, e.g. not more than 10 to 15%.

Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromouracil, azaadenines or azaguanines, etc.) attached to a peptide backbone through a suitable linker.

In preferred embodiments, the nucleic acid analogues used in the invention have the general formula (I):

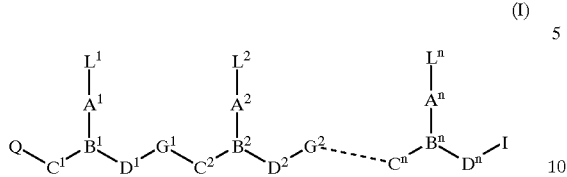

(I)

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups and reporter ligands, at least one of $L^1$–$L^n$ being a naturally occurring nucleobase, a non-naturally occurring nucleobase, a DNA intercalator, or a nucleobase-binding group;

each of $A^1$–$A^n$ is a single bond, a methylene group or a group of formula (IIa) or (IIb):

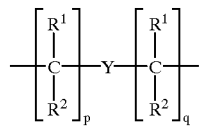

(IIa)

or

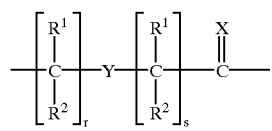

(IIb)

where:
$X$ is O, S, Se, $NR^3$, $CH_2$ or $C(CH_3)_2$;
$Y$ is a single bond, O, S or $NR^4$;
each of p and q is an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, ($C_1$–$C_4$)alkyl which may be hydroxy- or alkoxy- or alkylthio-substituted, hydroxy, alkoxy, alkylthio, amino and halogen; and
each $R^3$ and $R^4$ is independently selected from the group consisting of hydrogen, ($C_1$–$C_4$)alkyl, hydroxy- or alkoxy- or alkylthio-substituted ($C_1$–$C_4$)alkyl, hydroxy, alkoxy, alkylthio and amino;

each of $B^1$–$B^n$ is N or $R^3N^+$, where $R^3$ is as defined above;
each of $C^1$–$C^n$ is $CR^6R^7$, $CHR^6CHR^7$ or $CR^6R^7CH_2$, where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;
each of $D^1$–$D^n$ is $CR^6R^7$, $CH_2CR^6R^7$ or $CHR^6CHR^7$, where $R^6$ and $R^7$ are as defined above;
each of $G^1$–$G^{n-1}$ is

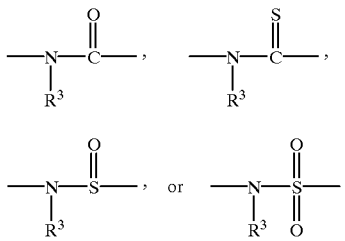

in either orientation, where $R^3$ is as defined above;
Q is —$CO_2H$, —CONR'R", —$SO_3H$ or —$SO_2NR'R"$ or an activated derivative of —$CO_2H$ or —$SO_3H$; and
I is —NHR'''R'''' or —NR'''C(O)R'''', where R', R", R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers. Alternatively, C and D may be $CHR^6(CH_2)_sCHR^7$ where S may be from 0 to 2.

Preferred peptide nucleic acids have general formula (III):

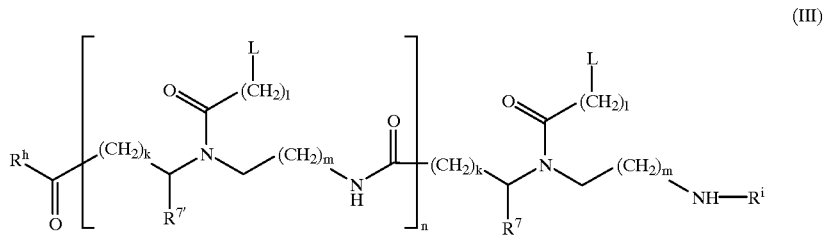

(III)

wherein:
each L is independently selected from the group consisting of hydrogen, phenyl, heterocycles, e.g. of one, two or three rings, naturally occurring nucleobases, and non-naturally occurring nucleobases;
each $R^{7'}$ is independently selected from the group consisting of hydrogen and the side chains of naturally occurring alpha amino acids;
n is an integer from 1 to 60;
each of k, l and m is independently zero or an integer from 1 to 5; preferably the sum of k and m is 1 or 2, most preferably 1;
$R^h$ is OH, $NH_2$ or —$NHLysNH_2$; and
$R^i$ is H or $COCH_3$.

Particularly preferred are compounds having formula (III) wherein each L is independently selected from the group consisting of the nucleobases thymine (T), adenine (A), cytosine (C), guanine (G) and uracil (U), in particular thymine, and n is an integer from 1 to 30, in particular from 4 to 20. An example of such a compound is provided in FIG. 1, which shows the structural similarity between such compounds and single-stranded DNA.

The peptide nucleic acids of the invention may be synthesized by adaptation of standard peptide synthesis procedures, either in solution or on a solid phase. The synthons used may be specially designed monomer amino acids or their activated derivatives, protected by standard protecting groups. The oligonucleotide analogues also can be synthesized by using the corresponding diacids and diamines.

Thus, the monomer synthons used to produce compounds for use on the invention may be selected from the group consisting of amino acids, diacids and diamines having general formulae:

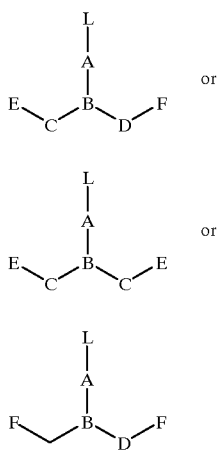

(IV)

or (V)

or (VI)

wherein L, A, B, C and D are as defined above, except that any amino groups therein may be protected by amino protecting groups; E is COOH, CSOH, SOOH, SO$_2$OH or an activated derivative thereof; and F is NHR$^3$ or NPgR$^3$, where R$^3$ is as defined above and Pg is an amino protecting group.

Preferred monomer synthons are amino acids having formula (VII):

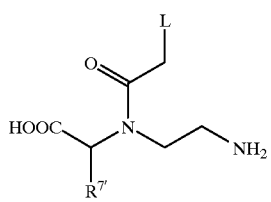

(VII)

or amino-protected and/or acid terminal activated derivatives thereof, wherein L is selected from the group consisting of hydrogen, phenyl, heterocycles, naturally occurring nucleobases, non-naturally occurring nucleobases, and protected derivatives thereof; and R$^{7'}$ is independently selected from the group consisting of hydrogen and the side chains of naturally occurring alpha amino acids. Especially preferred are such synthons having formula (4) wherein R$^{7'}$ is hydrogen and L is selected from the group consisting of the nucleobases thymine (T), adenine (A), cytosine (C), guanine (G) and uracil (U) and protected derivatives thereof.

In accordance with the invention there is included the use of nucleic acid analogues as hereinbefore defined in the capture, recognition, detection, identification or quantitation of one or more chemical or micro-biological entities. Usually it is envisaged the entity which is detected in the first instance will be a nucleic acid and said entity will be detected via its characteristic sequences of nucleic acid bases by hybridisation.

Nucleic acid analogues as hereinbefore defined may be used in a method of capturing a nucleic acid comprising contacting under hybridising conditions said nucleic acid with a nucleic acid analogue for use in the invention immobilised to a solid support, which immobilised nucleic acid analogue has a sequence of ligands suitable to hybridise to said nucleic acid or nucleic acid analogue to be captured.

The solid support may take a wide variety of forms as is known in connection with the immobilisation of conventional oligo-nucleotides for use in affinity capture. A solid support may for instance be a plate, a filter, a multi-well plate or a dip stick. It may take the form of individual particles such as beads and such particles may be held in a column through which nucleic acid containing solutions may be run to allow the capture of desired species therefrom.

The captured nucleic acid may be recognised, detected, identified or quantitated by a wide variety of methods. Since after washing the captured nucleic acid may be the only nucleic acid remaining in the system, it may be detected by any reagent system suitable for demonstrating the presence of nucleic acid, whether or not specific for the captured sequence. Thus by way of example if the captured nucleic acid is DNA and is captured in single stranded form by a relatively short PNA, overhanging single stranded DNA may be digested by nuclease and the digestion products may be detected by conventional means. If the DNA is double stranded and the PNA is once again relatively short, that part of the DNA which remains in its original double stranded form (i.e. which is not displaced by the PNA) can be detected by conventional DNA intercalators that do not bind to the PNA-DNA duplex. Antibodies which recognise nucleic acids may be used to detect nucleic acids (RNA, dsDNA or ssDNA) bound to the immobilised nucleic acid analogue.

In the affinity capture of nucleic acid species using conventional oligonucleotides immobilised to a solid support, it is necessary normally to purify the target nucleic acid. Nucleases which may be present in the sample are liable to attack the immobilised nucleic acid. Little specific binding is obtained in practice with much non-specific binding. Furthermore, it is necessary to denature the DNA to single stranded form before the capture can take place.

The nucleic acid analogues of Formula I above are not susceptible to attack by nucleases and typically provide higher levels of specific binding by virtue of their higher affinity for nucleic acid of complementary sequence than is obtained using conventional oligonucleotides as the immobilised species. Furthermore, the nucleic acid analogues used in accordance with the invention are typically capable of hybridising to nucleic acids of complementary sequence without those nucleic acids first being denatured into single stranded form. Once the target nucleic acid has been captured, it may be released from the immobilised nucleic acid analogue by subjecting the immobilised nucleic acid analogue and captured nucleic acid to dehybridising conditions such as heat and dimethyl formamide.

By way of example, the immobilised nucleic acid analogue may comprise sequential ligands such as thymine, hybridisable to poly A tails of mRNA to capture the mRNA.

The invention includes an affinity capture column comprising immobilised nucleic acid analogues as described above.

Thus it can be seen that the present invention also pertains to the advantageous use of PNA molecules in solid-phase biochemistry (see, e.g., "Solid-Phase Biochemistry—Analytical and Synthetic Aspects", W. H. Scouten, ed., John Wiley & Sons, New York, 1983), notably solid-phase biosystems, especially bioassays or solid-phase techniques which concern diagnostic detection/quantitation or affinity purification of complementary nucleic acids (see, e.g., "Affinity Chromatography—A Practical Approach", P. D. G. Dean, W. S. Johnson and F. A. Middle, eds., IRL Press Ltd., Oxford 1986; "Nucleic Acid Hybridization—A Practical Approach", B. D. Harnes and S. J. Higgins, IRL Press Ltd., Oxford 1987). Present day methods for performing such bioassays or purification techniques almost exclusively utilize "normal" or slightly modified oligonucleotides either physically adsorbed or bound through a substantially permanent covalent anchoring linkage to beaded solid supports such as cellulose, glass beads, including those with controlled porosity (Mizutani, et al., *J. Chromatogr.*, 1986, 356, 202), "Sephadex", "Sepharose", agarose, polyacrylamide, porous particulate alumina, hydroxyalkyl methacrylate gels, diol-bonded silica, porous ceramics, or contiguous materials such as filter discs of nylon and nitrocellulose. One example employed the chemical synthesis of oligo-dT on cellulose beads for the affinity isolation of poly A tail containing mRNA (Gilham in "*Methods in Enzymology*," L. Grossmann and K. Moldave, eds., vol. 21, part D, page 191, Academic Press, New York and London, 1971). All the above-mentioned methods are applicable within the context of the present invention. However, when possible, covalent linkage is preferred over the physical adsorption of the molecules in question, since the latter approach has the disadvantage that some of the immobilized molecules can be washed out (desorbed) during the hybridization or affinity process. There is, thus, little control of the extent to which a species adsorbed on the surface of the support material is lost during the various treatments to which the support is subjected in the course of the bioassay/purification procedure. The severity of this problem will, of course, depend to a large extent on the rate at which equilibrium between adsorbed and "free" species is established. In certain cases it may be virtually impossible to perform a quantitative assay with acceptable accuracy and/or reproducibility. Loss of adsorbed species during treatment of the support with body fluids, aqueous reagents or washing media will, in general, be expected to be most pronounced for species of relatively low molecular weight. In contrast with oligonucleotides, PNA molecules are easier to attach onto solid supports because they contain strong nucleophilic and/or electrophilic centers. In addition, the direct assembly of oligonucleotides onto solid supports suffers from an extremely low loading of the immobilized molecule, mainly due to the low surface capacity of the materials that allow the successful use of the state-of-the-art phosphoramidite chemistry for the construction of oligonucleotides. (Beaucage and Caruthers, *Tetrahedron Lett.*, 1981, 22, 1859; Caruthers, *Science*, 1985, 232, 281). It also suffers from the fact that by using the alternative phosphite triester method (Letsinger and Mahadevan, *J. Am. Chem. Soc.* 1976, 98, 3655), which is suited for solid supports with a high surface/loading capacity, only relatively short oligonucleotides can be obtained. As for conventional solid-phase peptide synthesis, however, the latter supports are excellent materials for building up immobilized PNA molecules (the side-chain protecting groups may be removed from the synthesized PNA chain without cleaving the anchoring linkage holding the chain to the solid support). Thus, PNA species benefit from the above-described solid-phase techniques with respect to the much higher (and still sequence-specific) binding affinity for complementary nucleic acids and from the additional unique sequence-specific recognition of (and strong binding to) nucleic acids present in double-stranded structures. They also can be loaded onto solid supports in large amounts, thus further increasing the sensitivity/capacity of the solid-phase technique. Further, certain types of studies concerning the use of PNA in solid-phase biochemistry can be approached, facilitated, or greatly accelerated by use of the recently-reported "light-directed, spatially addressable, parallel chemical synthesis" technology (Fodor, et al., *Science*, 1991, 251, 767), a technique that combines solid-phase chemistry and photolithography to produce thousands of highly diverse, but identifiable, permanently immobilized compounds (such as peptides) in a substantially simultaneous way.

It has been found that PNA's according to Formula I exhibit a property never before observed which is that such a nucleic acid analogue is capable of hybridising to a conventional nucleic acid presented in double-stranded form and is capable under such conditions of hybridising to the strand which has a sequence complementary to the analogue and of displacing the other strand from the initial nucleic acid duplex. Such recognition can take place to dsDNA sequences 5–60 base pairs long. Sequences between 10 and 20 bases are of interest since this is the range within which unique DNA sequences of prokaryotes and eukaryotes are found. Reagents which recognize 17–18 bases are particular interest since this is the length of unique sequences in the human genome.

It has also been observed that when such a hybridisation reaction is conducted in solution, a second strand of the nucleic acid analogue having the same sequence as the first also hybridises to the nucleic acid strand of complementary sequence so as form a triple helix structure in which two similar strands of PNA are hybridised to a single strand of conventional nucleic acid. It is believed that the first PNA strand hybridises by inter-base hydrogen bonding of the usual kind whilst the second strand of PNA is received in the major groove of the initial duplex by Hoogsteen pairing. Where the PNA is immobilised to a solid support, hybridisation to double stranded nucleic acid with displacement of one strand therefrom is observed but the formation of triple helix structures may be prevented by the immobilisation of the PNA.

The invention includes a nucleic acid analogue as defined above incorporating or conjugated to a detectable label. Generally, all those methods for labelling peptides, DNA and/or RNA which are presently known may in general terms be applied to PNA's also. Thus, methods of labelling will include the use of radio-isotope labels, enzyme labels, biotin, spin labels, fluorophores, chemiluminence labels, antigen labels or antibody labels.

Labelled PNA's as described above may be used in methods of recognition, detection or quantitation of target nucleic acids comprising hybridising said target to a labelled nucleic acid analogue as defined above of sufficiently complementary sequence to hybridise therewith under hybridising conditions and detecting or quantitating said label of the nucleic acid analogue so hybridised to said target.

Optionally, the target may be immobilised on a substrate prior to the hybridisation.

In such a method, the target may be immobilised to the substrate by the hybridisation of the first region of the target to a capture nucleic acid or nucleic acid analogue having a sequence sufficiently complementary to said first region to hybridise therewith and which is itself immobilised to said substrate and the labelled nucleic acid analogue may be hybridised to a second region of the target.

The ability of at least preferred nucleic acid analogues according to the invention to hybridise to a double-stranded target nucleic acid and to displace one strand therefrom has been described above. The invention includes a method for displacing one strand from a nucleic acid duplex comprising hybridising to said duplex a nucleic acid analogue as defined above having an affinity for the other strand of said duplex sufficient to be able to displace said one strand therefrom.

The invention includes a method of detecting, identifying or quantitating a double-stranded target nucleic acid comprising hybridising thereto a displacing nucleic acid analogue as defined above capable of displacing one strand from a double-stranded target in which the other strand is of complementary sequence to said displacing nucleic acid analogue, wherein said displacing nucleic acid analogue is of sufficiently complementary sequence to said other strand of said double-stranded target to hybridise thereto so as to displace said one strand of said target in single stranded form, and detecting or quantitating the presence of said one strand after displacement from said double-stranded target.

The displaced strand may be broken down into fragments and the presence of said fragments may be detected. The displaced strand may preferably be broken down by attack by a nuclease. Thus, one may detect the present of a specific double-stranded target nucleic acid sequence by hybridising thereto a complementary PNA to produce strand displacement so as to produce single-stranded DNA in the reaction mixture and digest the single-stranded DNA by the use of a nuclease to produce nucleotides whose presence can be detected as an indicator that specifically the target double-stranded DNA was present initially.

The invention further includes kits for use in diagnostics incorporating at least one nucleic acid analogue as defined above and preferably comprising at least one such nucleic acid analogue which is labelled, e.g. a labelled PNA, and at least one detection reagent for use in detecting said label.

Generally, the nucleic acid analogues will be provided in solution in a hybridisation buffer. Such a kit will generally also include at least one wash buffer solution.

Where the nucleic acid analogue is indirectly labelled, e.g. by biotin, the kit may include a conjugate between an enzyme label and a material such as avidin able to bind to the label of the nucleic acid analogue.

Where the nucleic acid analogue is either directly or indirectly enzyme labelled, the kit may comprise a substrate for the enzyme which is suitable to undergo a monitorable reaction mediated by the enzyme.

BRIEF DESCRIPTION OF THE DRAWINGS

The invention will be described in further detail and will be illustrated by reference to the accompanying figures, in which:

FIGS. 12a–c show chemical, photochemical and enzymatic probing of dsDNA-AcrT10-Lys-$NH_2$ complex. Complexes between AcrT10-Lys-$NH_2$ and a $^{32}$P-end labelled DNA fragment containing a $dA_{10}/dT_{10}$ target sequence were probed by affinity photocleavage (FIG. 12a, lanes 1–3; FIG. 12b, lanes 1–3), photofootprinting (FIG. 12a, lanes 5–6), potassium permanganate probing (FIG. 12b, lanes 4–6) or probing by staphylococcus nuclease (FIG. 12b, lanes 8–10) or by nuclease $S_1$ (FIG. 12c). Either the A-strand (FIG. 12a) or the T-strand (FIGS. 12b,c) was probed.

FIG. 26 is an autoradiograph showing inhibition of transcription by RNA polymerase by $T_{10}$ PNA on the transcribed strand.

In the PNA's of Formula I and monomer synthons used in their production, ligand L is primarily a naturally occurring nucleobase attached at the position found in nature, i.e., position 9 for adenine or guanine, and position 1 for thymine or cytosine. Alternatively, each of some of the ligands L may be a non-naturally occurring nucleobase (nucleobase analog), another base-binding moiety, an aromatic moiety, ($C_1$–$C_4$)alkanoyl, hydroxy or even hydrogen. Some typical nucleobase ligands and illustrative synthetic ligands are shown in FIG. 2. Furthermore, L can be a DNA intercalator, a reporter ligand such as, for example, a fluorophor, radio label, spin label, hapten, or a protein-recognizing ligand such as biotin.

Figure 4:
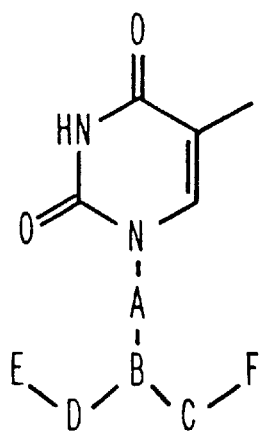
FIG. 4 provides examples of PNA monomer synthons.
Figure 4:
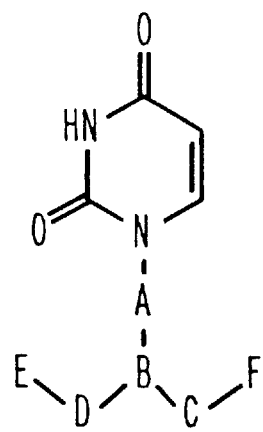
Figure 4:
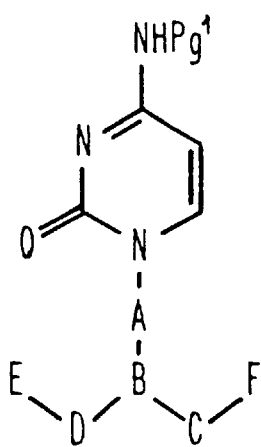
Figure 4:
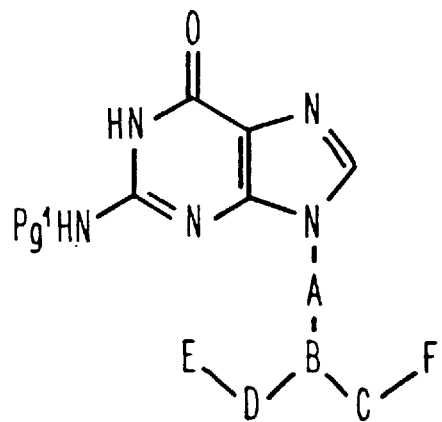
Figure 4:
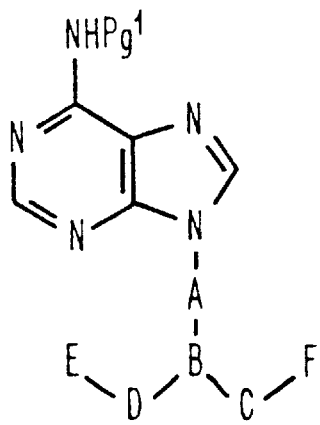
Figure 4:
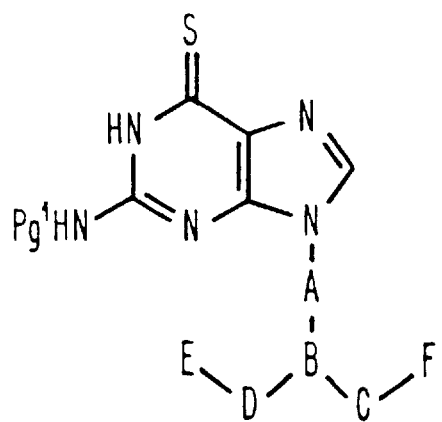

In monomer synthons, L may be equipped with protecting groups. This is illustrated in FIG. 4, where Pgl is an acid, a base or a hydrogenolytically or photochemically cleavable protecting group such as, for example, t-butoxycarbonyl (Boc), fluorenylmethyloxycarbonyl (Fmoc) or 2-nitrobenzyl (2Nb).

Linker A can be a wide variety of groups such as —$CR^1R^2CO$—, —$CR^1R^2CS$—, —$CR^1R^2CSe$—, —$CR^1R^2CNHR^3$—, —$CR^1R^2C=CH_2$— and —$CR^1R^2C=C(CH_3)_2$—, where $R^1$, $R^2$ and $R^3$ are as defined above. Preferably, A is methylenecarbonyl (—$CH_2CO$—). Also, A can be a longer chain moiety such as propanoyl, butanoyl or pentanoyl, or corresponding derivative, wherein O is replaced by another value of X or the chain is substituted with $R^1R^2$ or is heterogenous, containing Y. Further, A can be a ($C_2$–$C_6$)alkylene chain, a ($C_2$–$C_6$)alkylene chain substituted with $R^1R^2$ or can be heterogenous, containing Y. In certain cases, A can just be a single bond.

In the preferred form of the invention, B is a nitrogen atom, thereby presenting the possibility of an achiral backbone. B can also be $R^3N^+$, where $R^3$ is as defined above.

In the preferred form of the invention, C is —$CR^6R^7$—, but can also be a two carbon unit, i.e. —$CHR^6CHR^7$— or —$CR^6R^7CH_2$—, where $R^6$ and $R^7$ are as defined above. $R^6$ and $R^7$ also can be a heteroaryl group such as, for example, pyrrolyl, furyl, thionyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In the preferred form of the invention, E in the monomer synthon is COOH or an activated derivative thereof, and G in the oligomer is —$CONR^3$—. (Preferably in the orientation—$R^3NOC$ in Formula I). As defined above, E may also be CSOH, SOOH, $SO_2OH$ or an activated derivative thereof, whereby G in the oligomer becomes —$CSNR^3$—, —$SONR^3$— and —$SO_2NR^3$—, respectively. The activation may, for example, be achieved using an acid anhydride or an active ester derivative, wherein hydrogen in the groups represented by E is replaced by a leaving group suited for generating the growing backbone.

The amino acids which form the backbone may be identical or different. We have found that those based on 2-aminoethylglycine are especially well suited to the purpose of the invention.

In some cases it may be of interest to attach ligands at either terminus (Q, I) to modulate the binding characteristics of the PNAs. Representative ligands include DNA intercalators which will improve dsDNA binding or basic groups, such as lysine or polylysine, which will strengthen the binding of PNA due to electrostatic interaction. To decrease negatively charged groups such as carboxy and sulfo groups could be used. The design of the synthons further allows such other moieties to be located on non-terminal positions.

The PNA oligomers may be conjugated to low molecular effector ligands such as ligands having nuclease activity or alkylating activity or reporter ligands (fluorescent, spin labels, radioactive, protein recognition ligands, for example, biotin or haptens). In a further aspect of the invention, the PNAs are conjugated to peptides or proteins, where the peptides have signalling activity and the proteins are, for example, enzymes, transcription factors or antibodies. Also, the PNAs can be attached to water-soluble or water-insoluble polymers. In another aspect of the invention, the PNAs are conjugated to oligonucleotides or carbohydrates. When warranted, a PNA oligomer can be synthesized onto some moiety (e.g., a peptide chain, reporter, intercalator or other type of ligand-containing group) attached to a solid support.

Figure 1A:
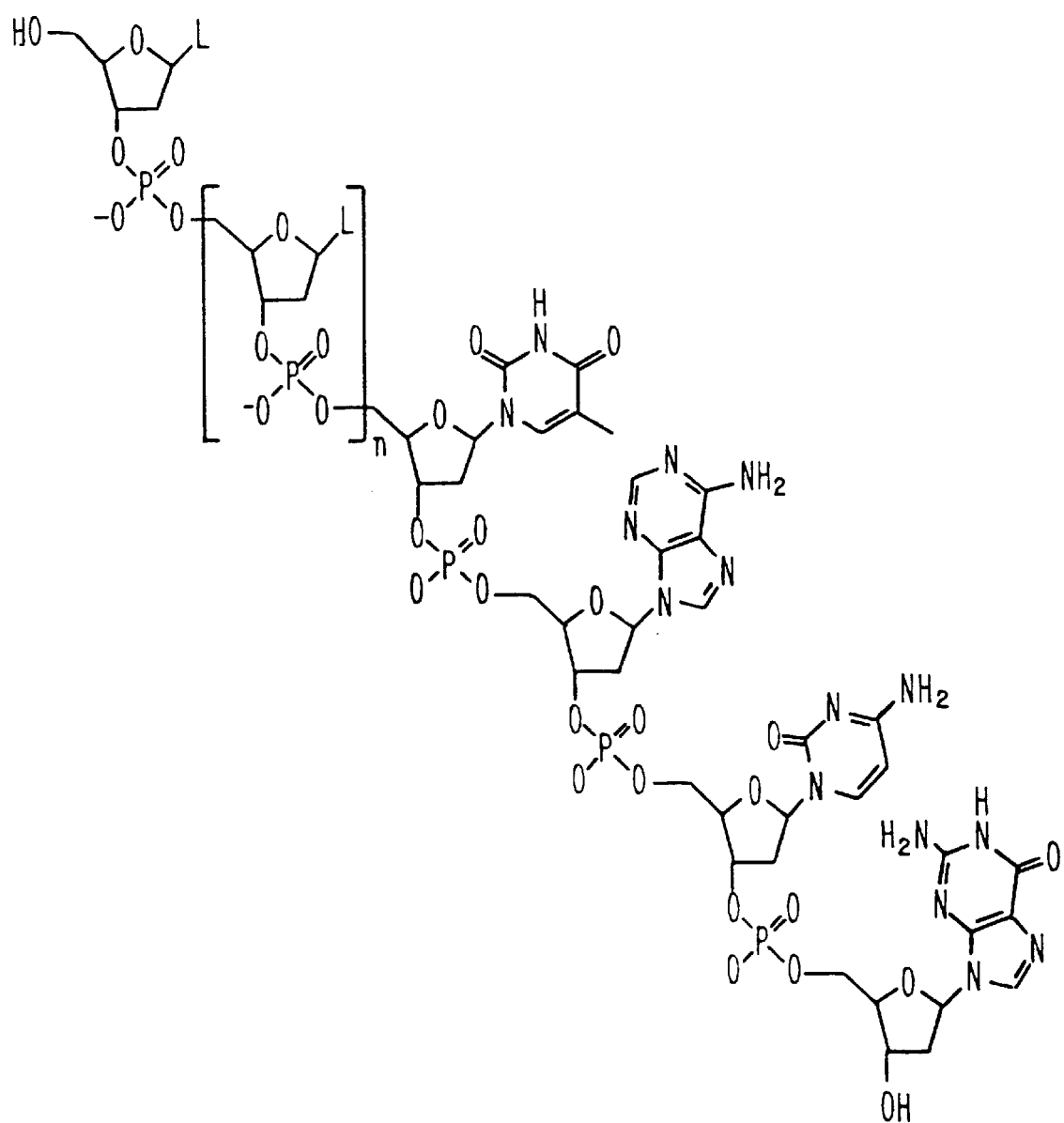
FIGS. 1(A) and 1(B) show a naturally occurring deoxyribooligonucleotide and a peptide nucleic acid (PNA of the invention, respectively.
Figure 1B:
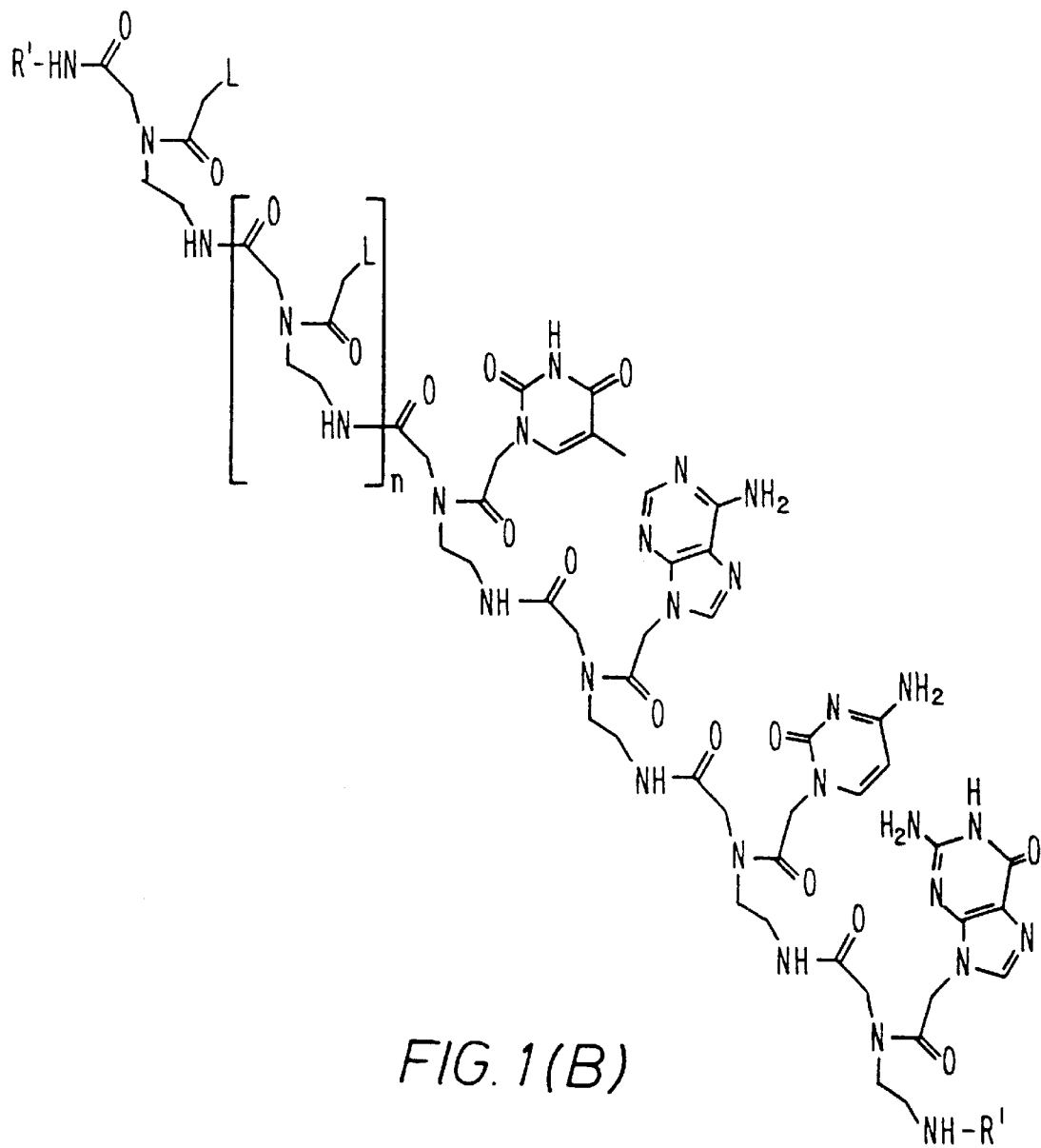
Figure 2A:
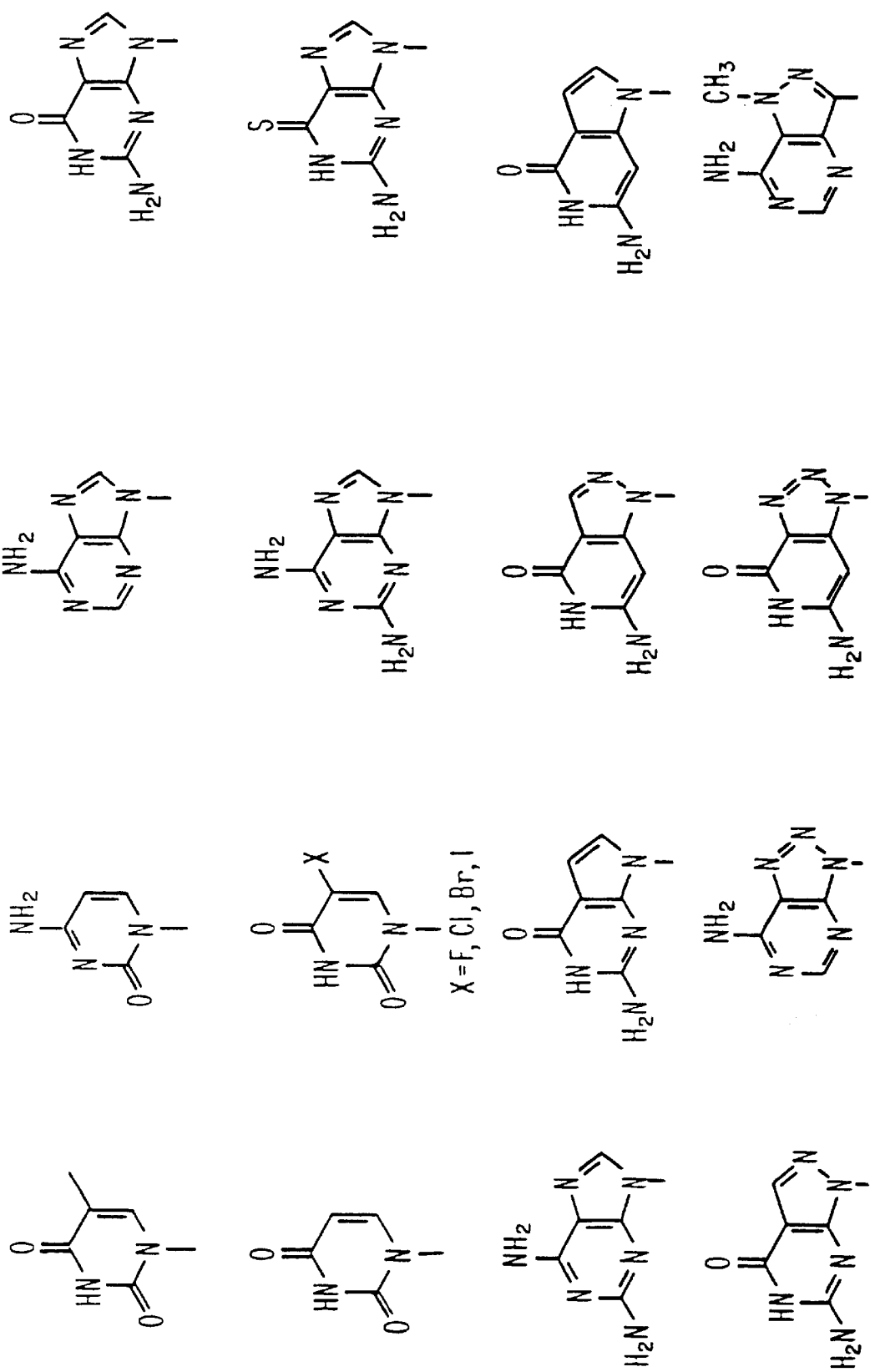
FIGS. 2(A) and 2(B) provide examples of naturally occurring and non-naturally occurring nucleobases for DNA recognition and reporter groups.
Figure 2B:
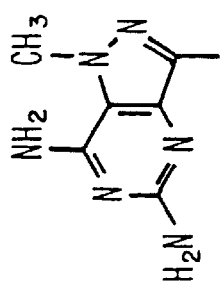
Figure 2B:
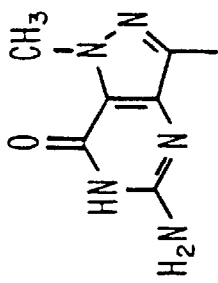
Figure 2B:
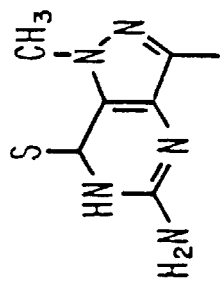
Figure 2B:
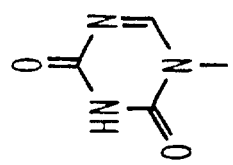
Figure 2B:
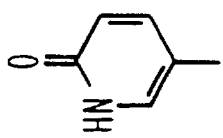
Figure 2B:
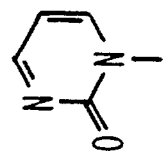
Figure 2B:
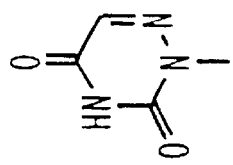
Figure 2B:
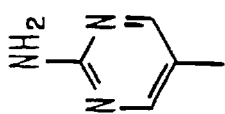
Figure 2B:
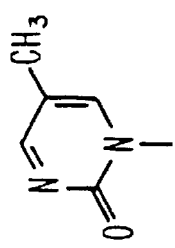
Figure 2B:
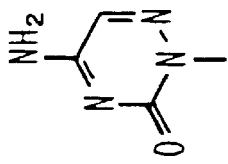
Figure 2B:
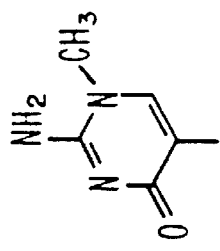
Figure 2B:
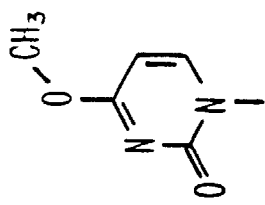
Figure 8:
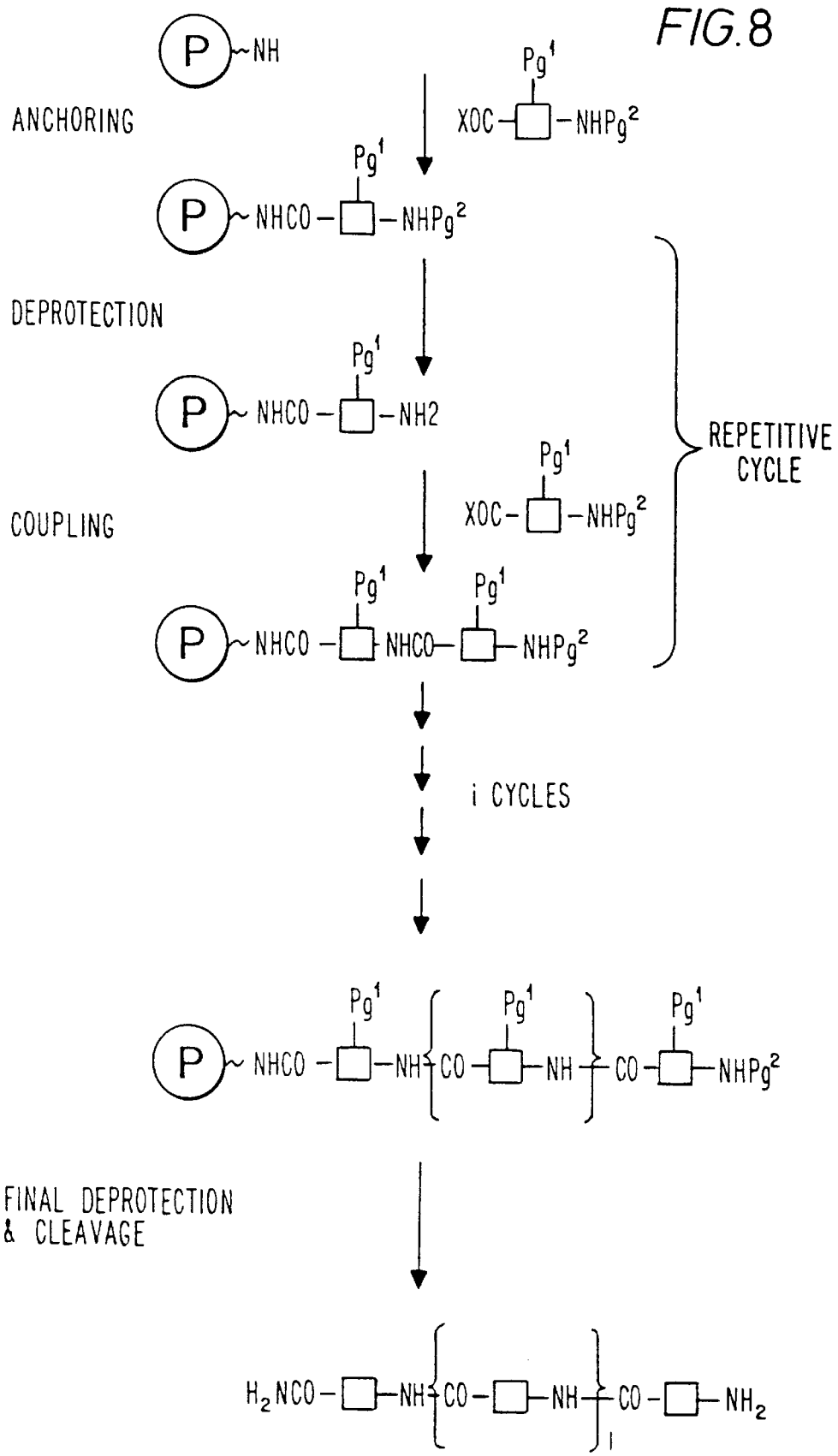
FIG. 8 provides a general scheme for solid-phase PNA synthesis illustrating the preparation of linear unprotected PNA amides.
Figure 9:
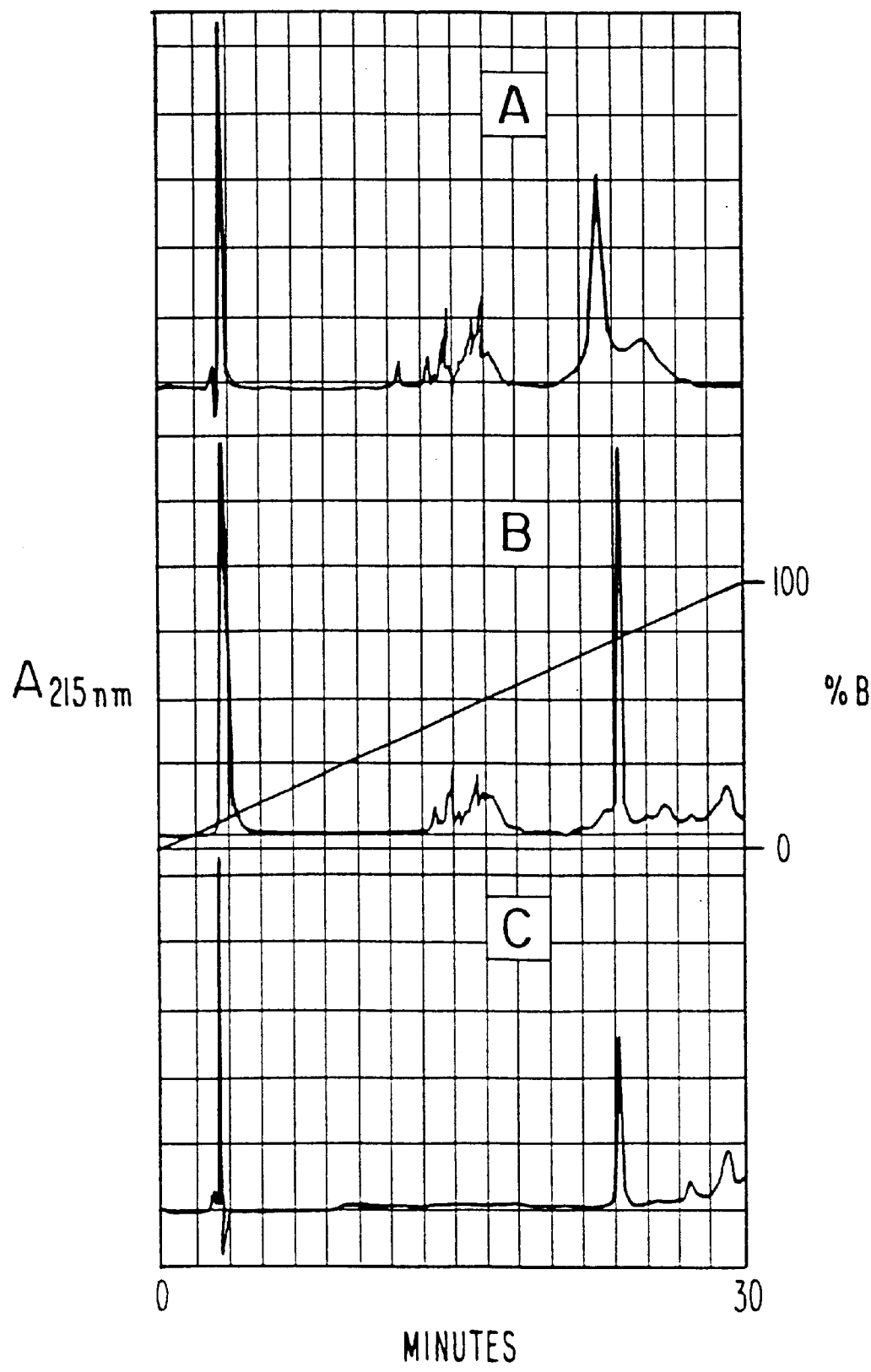
FIG. 9 shows analytical HPLC chromatograms of: (A) crude H—$[Taeg]_{15}$—$NH_2$ after HF-cleavage (before lyophilization); (B) crude $Acr^1$-$[Taeg]_{15}$—$NH_2$ after HF-cleavage (before lyophilization); and (C) purified $Acr^1$-$[Taeg]_{15}$—$NH_2$. Buffer A, 5% $CH_3CN$/95% $H_2O$/0.0445% TFA; buffer B, 60% $CH_3CN$/40% $H_2O$/0.0390% TFA; linear gradient, 0–100% of B in 30 min; flow rate, 1.2 ml/min; column, Vydac $C_{18}$ (5 μm, 0.46×25 cm).
Figure 10:
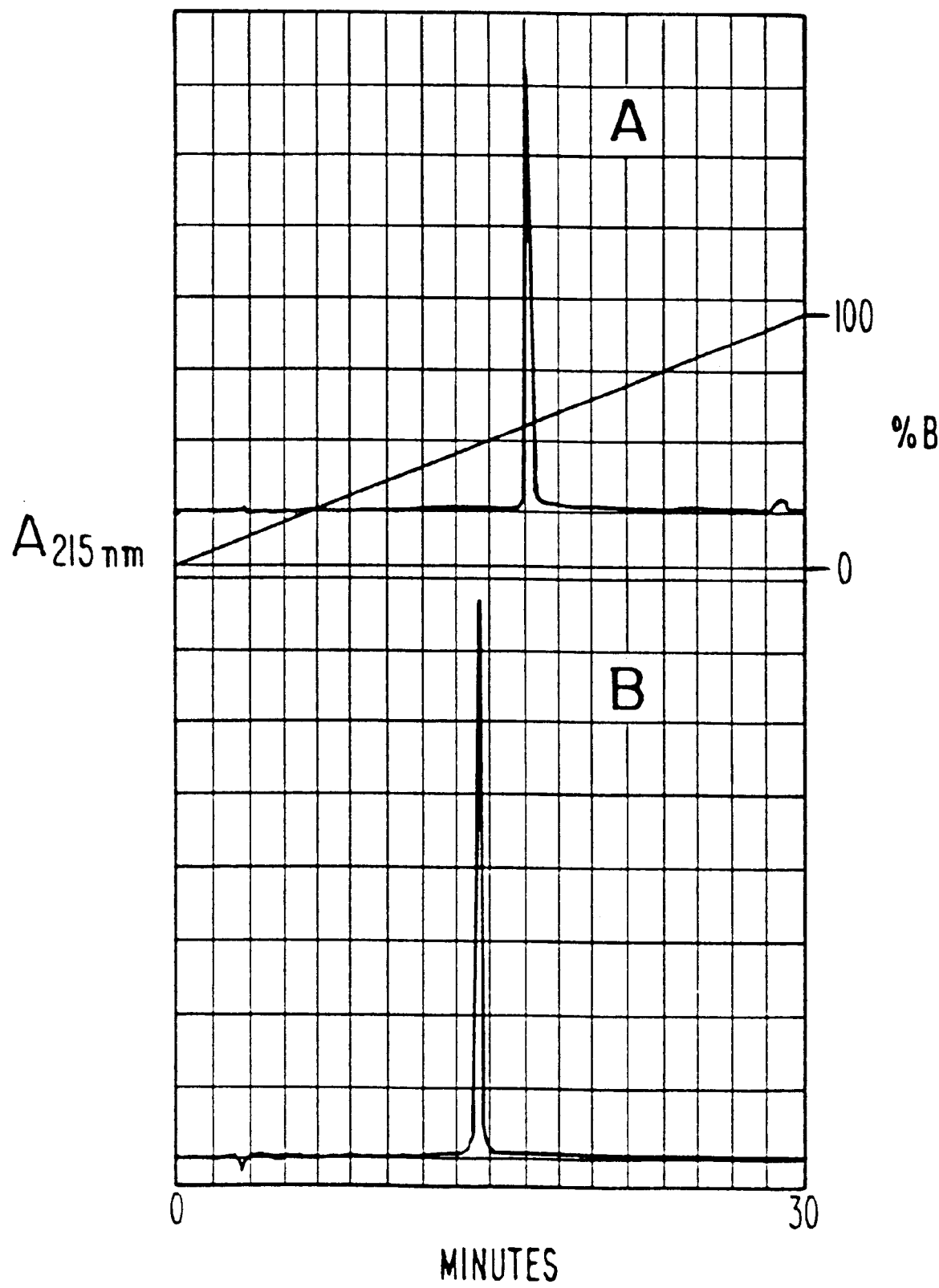
FIG. 10 shows analytical HPLC chromatograms of: (A) purified H—$[Taeg]_{10}$-Lys-$NH_2$ and (B) purified H—$[Taeg]_5$-Caeg-$[Taeg]_4$-Lys-$NH_2$ employing the same conditions as in FIG. 9.

The synthesis of the PNAs for use in to the invention is discussed in detail in the following, where FIG. 1 illustrates one of the preferred PNA examples and compares its structure to that of a complementary DNA. Synthesis of PNA Oligomers and Polymers The principle of anchoring molecules onto a solid matrix, which helps in accounting for intermediate products during chemical transformations, is known as Solid-Phase Synthesis or Merrifield Synthesis (see, e.g., Merrifield, *J. Am. Chem. Soc.*, 1963, 85, 2149 and *Science*, 1986, 232, 341). Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention (FIG. 8).

Concerning the initial functionalization of the solid phase, more than fifty methods have been described in connection with traditional solid-phase peptide synthesis (see, e.g., Barany and Merrifield in "The Peptides" Vol. 2, Academic Press, New York, 1979, pp. 1–284, and Stewart and Young, "Solid Phase Peptide Synthesis", 2nd Ed., Pierce Chemical Company, Illinois, 1984). Reactions for the introduction of chloromethyl functionality (Merrifield resin; via a chloromethyl methyl ether/$SnCl_4$ reaction), aminomethyl functionality (via an N-hydroxymethylphthalimide reaction; see, Mitchell, et al., *Tetrahedron Lett.*, 1976, 3795), and benzhydrylamino functionality (Pietta, et al., *J. Chem. Soc.*, 1970, 650) are the most widely applied. Regardless of its nature, the purpose of the functionality is normally to form an anchoring linkage between the copolymer solid support and the C-terminus of the first amino acid to be coupled to the solid support. It is generally convenient to express the "concentration" of a functional group in terms of millimoles per gram (mmol/g). Other reactive functionalities which have been initially introduced include 4-methylbenzhydrylamino and 4-methoxybenzhydrylamino. All of these established methods are in principle useful within the context of the present invention. Preferred methods for PNA synthesis employ aminomethyl as the initial functionality, in that aminomethyl is particularly advantageous with respect to the incorporation of "spacer" or "handle" groups, owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see, Barany, et al., *Int. J. Peptide Protein Res.*, 1987, 30, 705), especially reagents which are reactive towards amino groups such as found in the aminomethyl function. Representative bifunctional reagents include 4-(haloalkyl)aryl-lower alkanoic acids such as 4-(bromomethyl)phenylacetic acid, Boc-aminoacyl-4-(oxymethyl)aryl-lower alkanoic acids such as Boc-aminoacyl-4-(oxymethyl)phenylacetic acid, N-Boc-p-acylbenzhydrylamines such as N-Boc-p-glutaroylbenzhydrylamine, N-Boc-4'-lower alkyl-p-acylbenzhydrylamines such as N-Boc-4'-methyl-p-glutaroylbenzhydrylamine, N-Boc-4'-lower alkoxy-p-acylbenzhydrylamines such as N-Boc-4'-methoxy-p-glutaroyl-benzhydrylamine, and 4-hydroxymethylphenoxyacetic acid. One type of spacer group particularly relevant within the context of the present invention is the phenylacetamidomethyl (Pam) handle (Mitchell and Merrifield, *J. Org. Chem.*, 1976, 41, 2015) which, deriving from the electron withdrawing effect of the 4-phenylacetamidomethyl group, is about 100 times more stable than the classical benzyl ester linkage towards the Boc-amino deprotection reagent trifluoroacetic acid (TFA).

Certain functionalities (e.g., benzhydrylamino, 4-methylbenzhydrylamino and 4-methoxybenzhydrylamino) which may be incorporated for the purpose of cleavage of a synthesized PNA chain from the solid support such that the C-terminal of the PNA chain is in amide form, require no introduction of a spacer group. Any such functionality may advantageously be employed in the context of the present invention.

An alternative strategy concerning the introduction of spacer or handle groups is the so-called "preformed handle" strategy (see, Tam, et al., *Synthesis*, 1979, 955–957), which offers complete control over coupling of the first amino acid, and excludes the possibility of complications arising from the presence of undesired functional groups not related to the peptide or PNA synthesis. In this strategy, spacer or handle groups, of the same type as described above, are reacted with the first amino acid desired to be bound to the solid support, the amino acid being N-protected and optionally protected at the other side-chains which are not relevant with respect to the growth of the desired PNA chain. Thus, in those cases in which a spacer or handle group is desirable, the first amino acid to be coupled to the solid support can either be coupled to the free reactive end of a spacer group which has been bound to the initially introduced functionality (for example, an aminomethyl group) or can be reacted with the spacer-forming reagent. The space-forming reagent is then reacted with the initially introduced functionality. Other useful anchoring schemes include the "multidetachable" resins (Tam, et al., *Tetrahedron Lett.*, 1979, 4935 and *J. Am. Chem. Soc.*, 1980, 102, 611; Tam, *J. Org. Chem.*, 1985, 50, 5291), which provide more than one mode of release and thereby allow more flexibility in synthetic design.

Suitable choices for N-protection are the tert-butyloxycarbonyl (Boc) group (Carpino, *J. Am. Chem. Soc.*, 1957, 79, 4427; McKay, et al., *J. Am. Chem. Soc.*, 1957, 79, 4686; Anderson, et al., *J. Am. Chem. Soc.*, 1957, 79, 6180) normally in combination with benzyl-based groups for the protection of side chains, and the 9-fluorenylmethyloxycarbonyl (Fmoc) group (Carpino, et al., *J. Am. Chem. Soc.*, 1970, 92, 5748 and *J. Org. Chem.*, 1972, 37, 3404), normally in combination with tert-butyl (tBu) for the protection of any side chains, although a number of other possibilities exist which are well known in conventional solid-phase peptide synthesis. Thus, a wide range of other useful amino protecting groups exist, some of which are Adoc (Hass, et al., *J. Am. Chem. Soc.*, 1966, 88, 1988), Bpoc (Sieber, *Helv. Chem. Acta.*, 1968, 51, 614), Mcb (Brady, et al., *J. Org. Chem.*, 1977, 42, 143), Bic (Kemp, et al., *Tetrahedron*, 1975, 4624), the o-nitrophenylsulfenyl (Nps) (Zervas, et al., *J. Am. Chem. Soc.*, 1963, 85, 3660), and the dithiasuccinoyl (Dts) (Barany, et al., *J. Am. Chem. Soc.*, 1977, 99, 7363). These amino protecting groups, particularly those based on the widely-used urethane functionality, successfully prohibit racemization (mediated by tautomerization of the readily formed oxazolinone (azlactone) intermediates (Goodman, et al., *J. Am. Chem. Soc.*, 1964, 86, 2918)) during the coupling of most '-amino acids. In addition to such amino protecting groups,a whole range of otherwise "worthless" nonurethane-type of amino protecting groups are applicable when assembling PNA molecules, especially those built from achiral units. Thus, not only the above-mentioned amino protecting groups (or those derived from any of these groups) are useful within the context of the present invention, but virtually any amino protecting group which largely fulfils the following requirements: (1) stability to mild acids (not significantly attacked by carboxyl groups); (2) stability to mild bases or nucleophiles (not significantly attacked by the amino group in question); (3) resistance to acylation (not significantly attacked by activated amino acids). Additionally: (4) the protecting group must be close to quantitatively removable, without serious side reactions, and (5) the optical integrity, if any, of the incoming amino acid should preferably be highly preserved upon coupling. Finally, the choice of side-chain protecting groups, in general, depends on the choice of the amino protecting group, since the protection of side-chain functionalities must withstand the conditions of the repeated amino deprotection cycles. This is true whether the overall strategy for chemically assembling PNA molecules relies on, for example, differential acid stability of amino and side-chain protecting groups (such as is the case for the above-mentioned "Boc-benzyl" approach) or employs an orthogonal, that is, chemoselective, protection scheme (such as is the case for the above-mentioned "Fmoc-tBu" approach), Following coupling of the first amino acid, the next stage of solid-phase synthesis is the systematic elaboration of the desired PNA chain. This elaboration involves repeated deprotection/coupling cycles. The temporary protecting group, such as a Boc or Fmoc group, on the last-coupled amino acid is quantitatively removed by a suitable treatment, for example, by acidolysis, such as with trifluoroacetic acid, in the case of Boc, or by base treatment, such as with piperidine, in the case of Fmoc, so as to liberate the N-terminal amine function.

The next desired N-protected amino acid is then coupled to the N-terminal of the last-coupled amino acid. This coupling of the C-terminal of an amino acid with the N-terminal of the last-coupled amino acid can be achieved in several ways. For example, it can be bound by providing the incoming amino acid in a form with the carboxyl group activated by any of several methods, including the initial formation of an active ester derivative such as a 2,4,5-trichlorophenyl ester (Pless, et al., *Helv. Chim. Acta*, 1963, 46, 1609), a phthalimido ester (Nefkens, et al., *J. Am. Chem. Soc.*, 1961, 83, 1263), a pentachlorophenyl ester (Kupryszewski, *Rocz. Chem.*, 1961, 35, 595), a pentafluorophenyl ester (Kovacs, et al., *J. Am. Chem. Soc.*, 1963, 85, 183), an o-nitrophenyl ester (Bodanzsky, *Nature*, 1955, 175, 685), an imidazole ester (Li, et al., *J. Am. Chem. Soc.*, 1970, 92, 7608), and a 3-hydroxy-4-oxo-3,4-dihydroquinazoline (Dhbt—OH) ester (Konig, et al., *Chem. Ber.*, 1973, 103, 2024 and 2034), or the initial formation of an anhydride such as a symmetrical anhydride (Wieland, et al., *Angew. Chem., Int. Ed. Engl.*, 1971, 10, 336). Alternatively, the carboxyl group of the incoming amino acid can be reacted directly with the N-terminal of the last-coupled amino acid with the assistance of a condensation reagent such as, for example, dicyclohexylcarbodiimide (Sheehan, et al., *J. Am. Chem. Soc.*, 1955, 77, 1067) or derivatives thereof. Benzotriazolyl N-oxytris-dimethylaminophosphonium hexafluorophosphate (BOP), "Castro's reagent" (see, e.g., Rivaille, et al., *Tetrahedron*, 1980, 36, 3413) is recommended when assembling PNA molecules containing secondary amino groups. Finally, activated PNA monomers analogous to the recently-reported amino acid fluorides (Carpino, *J. Am. Chem. Soc.*, 1990, 112, 9651) hold considerable promise to be used in PNA synthesis as well.

Following assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form. Alternatively, in cases in which condensation of two separately synthesized PNA chains is to be carried out, it is possible by choosing a suitable spacer group at the start of the synthesis to cleave the desired PNA chains from their respective solid supports (both peptide chains still incorporating their side-chain protecting groups) and finally removing the side-chain protecting groups after, for example, coupling the two side-chain protected peptide chains to form a longer PNA chain.

In the above-mentioned "Boc-benzyl" protection scheme, the final deprotection of side-chains and release of the PNA molecule from the solid support is most often carried out by the use of strong acids such as anhydrous HF (Sakakibara, et al., *Bull. Chem. Soc. Jpn.*, 1965, 38, 4921), boron tris (trifluoroacetate) (Pless, et al., *Helv. Chim. Acta*, 1973, 46, 1609), and sulfonic acids such as trifluoromethanesulfonic acid and methanesulfonic acid (Yajima, et al., *J. Chem. Soc., Chem. Comm.*, 1974, 107). This conventional strong acid (e.g., anhydrous HF) deprotection method, produces very reactive carbocations that may lead to alkylation and acylation of sensitive residues in the PNA chain. Such side-reactions are only partly avoided by the presence of scavengers such as anisole, phenol, dimethyl sulphide, and mercaptoethanol and, therefore, the sulphide-assisted acidolytic $S_N2$ deprotection method (Tam, et al., *J. Am. Chem. Soc.*, 1983, 105, 6442 and *J. Am. Chem. Soc.*, 1986, 108, 5242), the so-called "low", which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the PNA-solid support bond are, for example, such methods as base-catalyzed alcoholysis (Barton, et al., *J. Am. Chem. Soc.*, 1973, 95, 4501), and ammonolysis as well as hydrazinolysis (Bodanszky, et al., *Chem. Ind.*, 1964 1423), hydrogenolysis (Jones, *Tetrahedron Lett.* 1977 2853 and Schlatter, et al., *Tetrahedron Lett.* 1977 2861)), and photolysis (Rich and Gurwara, *J. Am. Chem. Soc.*, 1975 97, 1575)).

Finally, in contrast with the chemical synthesis of "normal" peptides, stepwise chain building of achiral PNAs such as those based on aminoethylglycyl backbone units can start either from the N-terminus or the C-terminus, because the coupling reactions are free of racemization.

Based on the recognition that most operations are identical in the synthetic cycles of solid-phase peptide synthesis (as is also the case for solid-phase PNA synthesis), a new matrix, PEPS, was recently introduced (Berg, et al., *J. Am. Chem. Soc.*, 1989, 111, 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously. Thus, in a new configuration for solid-phase peptide synthesis, the PEPS film is fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. It was reasoned that the PEPS film support, comprising linker or spacer groups adapted to the particular chemistry in question, should be particularly valuable in the synthesis of multiple PNA molecules, these being conceptually simple to synthesize since only four different reaction compartments are normally required, one for each of the four "pseudo-nucleotide" units. Thus, the PEPS film support has been successfully tested in a number of PNA syntheses carried out in a parallel and substantially simultaneous fashion. The yield and quality of the products obtained from PEPS were comparable to those obtained by using the traditional polystyrene beaded support. Also, experiments with other geometries of the PEPS polymer such as, for example, non-woven felt, knitted net, sticks or microwell-plates have not indicated any limitations of the synthetic efficacy.

Two other methods proposed for the simultaneous synthesis of large numbers of peptides also apply to the preparation of multiple, different PNA molecules. The first of these methods (Geysen, et al., *Proc. Natl. Acad. Sci. USA*, 1984, 81, 3998) utilizes acrylic acid-grafted polyethylene-rods and 96-microtiter wells to immobilize the growing peptide chains and to perform the compartmentalized synthesis. While highly effective, the method is only applicable on a microgram scale. The second method (Houghten, *Proc. Natl. Acad. Sci. USA*, 1985, 82, 5131) utilizes a "tea bag" containing traditionally-used polymer beads. Other relevant proposals for multiple peptide or PNA synthesis in the context of the present invention include the simultaneous use of two different supports with different densities (Tregear, in "*Chemistry and Biology of Peptides*", J. Meienhofer, ed., Ann Arbor Sci. Publ., Ann Arbor, 1972 pp. 175–178), combining of reaction vessels via a manifold (Gorman, *Anal. Biochem.*, 1984, 136, 397), multicolumn solid-phase synthesis (e.g. Krchnak, et al., *Int. J. Peptide Protein Res.*, 1989, 33, 209), and Holm and Meldal, in "*Proceedings of the 20th European Peptide Symposium*", G. Jung and E. Bayer, eds., Walter de Gruyter & Co., Berlin, 1989 pp. 208–210), and the use of cellulose paper (Eichler, et al., *Collect. Czech. Chem. Commun.*, 1989, 54, 1746).

While the conventional cross-linked styrene/divinylbenzene copolymer matrix and the PEPS support are presently preferred in the context of solid-phase PNA synthesis, a non-limiting list of examples of solid supports which may be of relevance are: (1) Particles based upon copolymers of dimethylacrylamide cross-linked with N,N'-bisacryloylethylenediamine, including a known amount of N-tertbutoxycarbonyl-beta-alanyl-N'-acryloyl-hexamethylenediamine. Several spacer molecules are typically added via the beta alanyl group, followed thereafter by the amino acid residue subunits. Also, the beta alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethyl-acetamide, N-methylpyrrolidone and the like (see Atherton, et al., *J. Am. Chem. Soc.*, 1975, 97, 6584, *Bioorg. Chem.* 1979, 8, 351), and J. C. S. Perkin I 538 (1981)); (2) a second group of solid supports is based on silica-containing particles such as porous glass beads and silica gel. One example is the reaction product of trichloro-[3-(4-chloromethyl)phenyl] propylsilane and porous glass beads (see Parr and Grohmann, *Angew. Chem. Internal. Ed.* 1972, 11, 314) sold under the trademark "PORASIL E" by Waters Associates, Framingham, Mass, USA. Similarly, a mono ester of 1,4-dihydroxymethylbenzene and silica (sold under the trademark "BIOPAK" by Waters Associates) has been reported to be useful (see Bayer and Jung, *Tetrahedron Lett.*, 1970, 4503); (3) a third general type of useful solid supports can be termed composites in that they contain two major ingredients: a resin and another material that is also substantially inert to the organic synthesis reaction conditions employed. One exemplary composite (see Scott, et al., *J. Chrom. Sci.*, 1971, 9, 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, Israel *J. Chem.* 1978, 17, 243) and van Rietschoten in "Peptides 1974", Y. Wolman, Ed., Wiley and Sons, New York, 1975, pp. 113–116); and (4) contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345), are suited for PNA synthesis as well.

Whether manually or automatically operated, solid-phase PNA synthesis in the context of the present invention is normally performed batchwise. However, most of the syntheses may equally well be carried out in the continuous-flow mode, where the support is packed into columns (Bayer, et al., *Tetrahedron Lett.*, 1970, 4503 and Scott, et al., *J. Chromatogr. Sci.*, 1971, 9, 577). With respect to continuous-flow solid-phase synthesis, the rigid poly (dimethylacrylamide)-Kieselguhr support (Atherton, et al., *J. Chem. Soc. Chem. Commun.*, 1981, 1151) appears to be particularly successful, but another valuable configuration concerns the one worked out for the standard copoly (styrene-1%-divinylbenzene) support (Krchnak, et al., *Tetrahedron Lett.*, 1987, 4469).

While the solid-phase technique is presently preferred in the context of PNA synthesis, other methodologies or combinations thereof, for example, in combination with the solid-phase technique, apply as well: (1) the classical solution-phase methods for peptide synthesis (e.g., Bodanszky, "*Principles of Peptide Synthesis*", Springer-Verlag, Berlin-New York 1984), either by stepwise assembly or by segment/fragment condensation, are of particular relevance when considering especially large scale productions (gram, kilogram, and even tons) of PNA compounds; (2) the so-called "liquid-phase" strategy, which utilizes soluble polymeric supports such as linear polystyrene (Shemyakin, et al., *Tetrahedron Lett.*, 1965, 2323) and polyethylene glycol (PEG) (Mutter and Bayer, *Angew. Chem., Int. Ed. Engl.*, 1974, 13, 88), is useful; (3) random polymerization (see, e.g., Odian, "*Principles of Polymerization*", McGraw-Hill, New York (1970)) yielding mixtures of many molecular weights ("polydisperse") peptide or PNA molecules are particularly relevant for purposes such as screening for antiviral effects; (4) a technique based on the use of polymer-supported amino acid active esters (Fridkin, et al., *J. Am. Chem. Soc.*, 1965, 87, 4646), sometimes referred to as "inverse Merrifield synthesis" or "polymeric reagent synthesis", offers the advantage of isolation and purification of intermediate products, and may thus provide a particularly suitable method for the synthesis of medium-sized, optionally protected, PNA molecules, that can subsequently be used for fragment condensation into larger PNA molecules; (5) it is envisaged that PNA molecules may be assembled enzymatically by enzymes such as proteases or derivatives thereof with novel specificities (obtained, for example, by artificial means such as protein engineering). Also, one can envision the development of "PNA ligases" for the condensation of a number of PNA fragments into very large PNA molecules; (6) since antibodies can be generated to virtually any molecule of interest, the recently developed catalytic antibodies (abzymes), discovered simultaneously by the groups of Lerner (Tramantano, et al., *Science*, 1986, 234, 1566) and of Schultz (Pollack, et al., *Science*, 1986, 234, 1570), should also be considered as potential candidates for assembling PNA molecules. Thus, there has been considerable success in producing abzymes catalyzing acyl-transfer reactions (see for example Shokat, et al., *Nature*, 1989, 338, 269) and references therein). Finally, completely artificial enzymes, very recently pioneered by Stewart's group (Hahn, et al., *Science*, 1990, 248, 1544), may be developed to suit PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases) as compared to the twenty natural by occurring (proteinogenic) amino acids constituting peptides. In conclusion, no single strategy may be wholly suitable for the synthesis of a specific PNA molecule, and therefore, sometimes a combination of methods may work best.

(a) Experimental for the Synthesis of Monomeric Building Blocks

The monomers preferably are synthesized by the general scheme outlined in FIG. 8. This involves preparation of either the methyl or ethyl ester of (Bocaminoethyl)glycine, by a protection/deprotection procedure as described in Examples 21–23. The synthesis of thymine monomer is described in Examples 24–25, and that of the protected cytosine monomer is described in Example 26.

Figure 14:
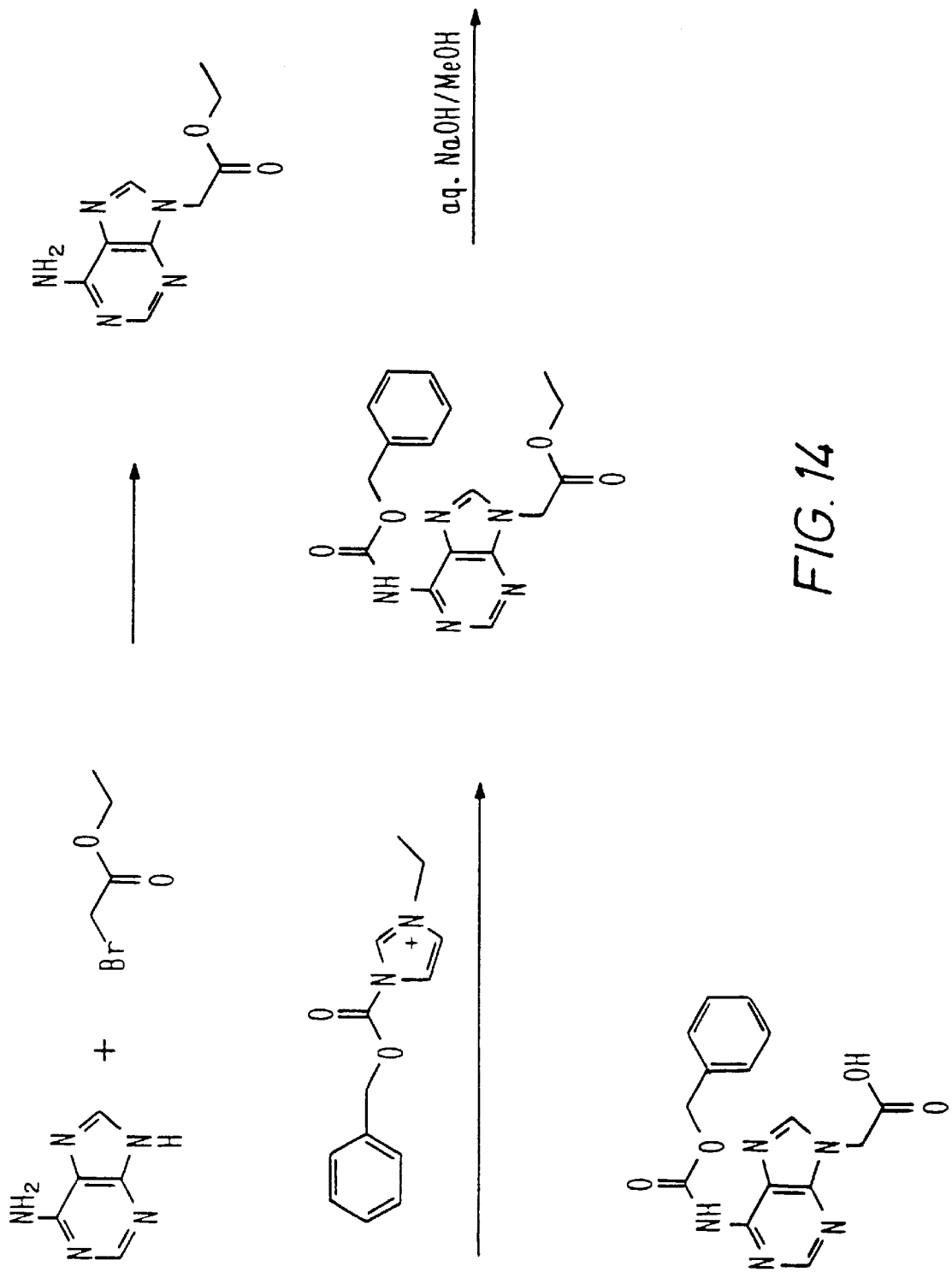
FIG. 14 provides a procedure for the synthesis of a protected adenine monomer synthon.

The synthesis of the protected adenine monomer (FIG. 14) involved alkylation with ethyl bromoacetate (Example 27) and verification of the position of substitution by X-ray crystallography, as being the wanted 9-position. The $N^6$-amino group then was protected with the benzyloxycarbonyl group by the use of the reagent N-ethyl-benzyloxycarbonylimidazole tetrafluoroborate (Example 28). Simple hydrolysis of the product ester (Example 29) gave $N^6$-benzyloxycarbonyl-9-carboxymethyl adenine, which then was used in the standard procedure (Examples 10–11, FIG. 8). The adenine monomer has been built into two different PNA-oligomers (Examples 30 and 31).

Figure 15:
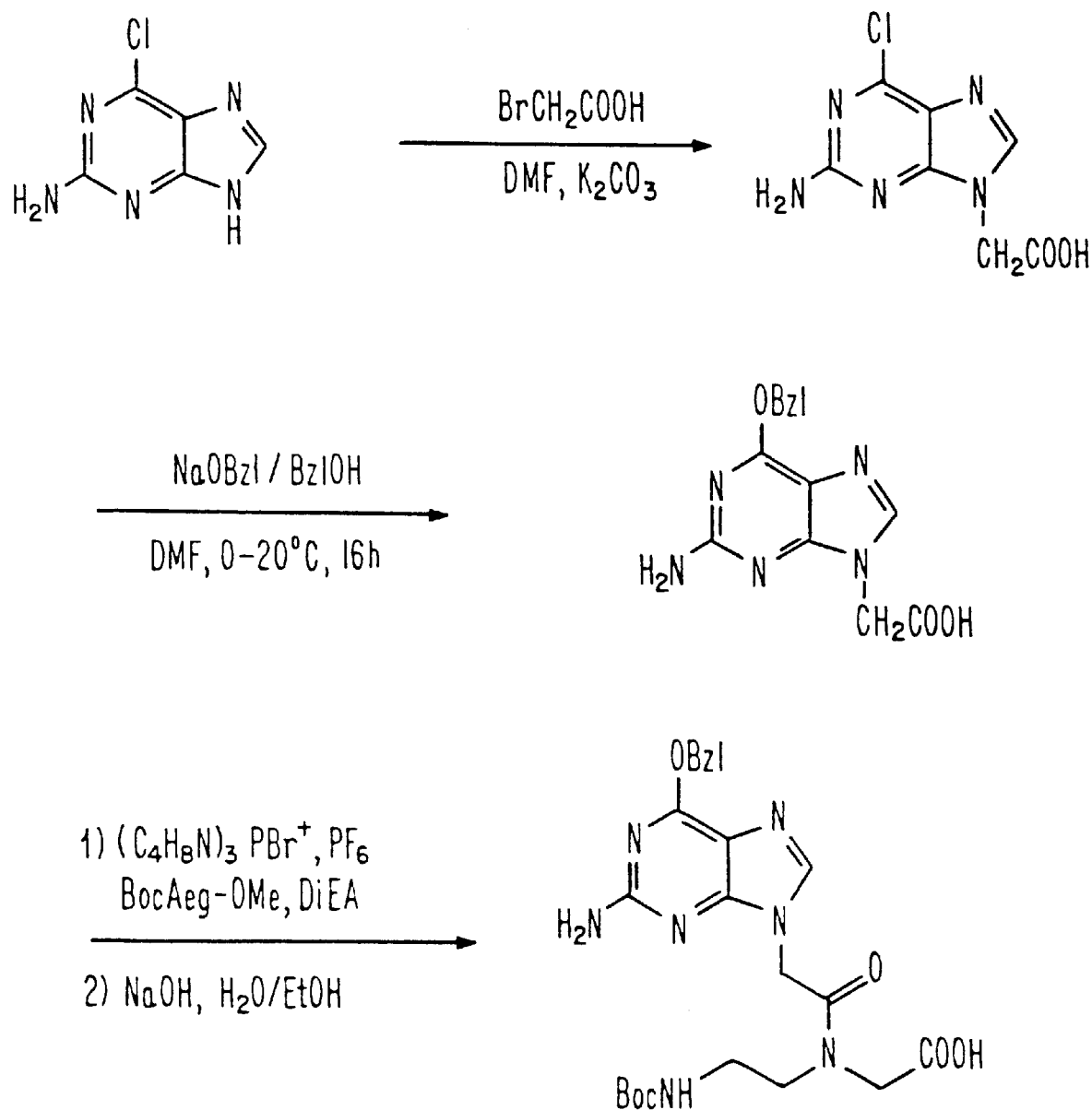
FIG. 15 provides a procedure for the synthesis of a protected guanine monomer synthon.

The synthesis of the protected G-monomer is outlined in FIG. 15. The starting material, 2-amino-6-chloropurine, was alkylated with bromoacetic acid (Example 32) and the chlorine atom was then substituted with a benzyloxy group (Example 36). The resulting acid was coupled to the (bocaminoethyl) glycine methyl ester (Example 33) with agent PyBrop™, and the resulting ester was hydrolysed (Example 23). The $O^6$-benzyl group was removed in the final HF-cleavage step in the synthesis of the PNA-oligomer. Cleavage was verified by finding the expected mass of the final PNA-oligomer, upon incorporation into an PNA-oligomer using diisopropyl carbodiimide as the condensation agent (Example 52).

The following abbreviations are used in the experimental examples: DMF, N,N-dimethylformamide; DCC, N,N-dicyclohexyl carbodiimide; DCU, N,N-dicyclohexyl urea; THF, tetrahydrofuran; aeg, N-acetyl (2'-aminoethyl)glycine; pfp, pentafluorophenyl; Boc, tert-butoxycarbonyl; Z, benzyloxycarbonyl; NMR, nuclear magnetic resonance; s, singlet; d, doublet; dd, doublet of doublets; t; triplet; q, quartet; m, multiplet; b, broad; δ, chemical shift;

NMR spectra were recorded on either a JEOL FX 90Q spectrometer, or a Bruker 250 MHz with tetramethylsilane as internal standard. Mass spectrometry was performed on a MassLab VG 12–250 quadropole instrument fitted with a VG FAB source and probe. Melting points were recorded on Buchi melting point apparatus and are uncorrected. N,N-Dimethylformamide was dried over 4 Å molecular sieves, distilled and stored over 4 Å molecular sieves. Pyridine (HPLC quality) was dried and stored over 4 Å molecular sieves. Other solvents used were either the highest quality obtainable or were distilled before use. Dioxane was passed through basic alumina prior to use. Bocanhydride, 4-nitrophenol, methyl bromoacetate, benzyloxycarbonyl chloride, pentafluorophenol were all obtained through Aldrich Chemical Company. Thymine, cytosine, adenine were all obtained through Sigma.

Thin layer chromatography (Tlc) was performed using the following solvent systems: (1) chloroform:triethyl amine:methanol, 7:1:2; (2) methylene chloride:methanol, 9:1; (3) chloroform:methanol:acetic acid 85:10:5. Spots were visualized by UV (254 nm) or/and spraying with a ninhydrin solution (3 g ninhydrin in 1000 ml 1-butanol and 30 ml acetic acid), after heating at 120° C. for 5 min and, after spraying, heating again.

Extended Backbones

Figure 16:
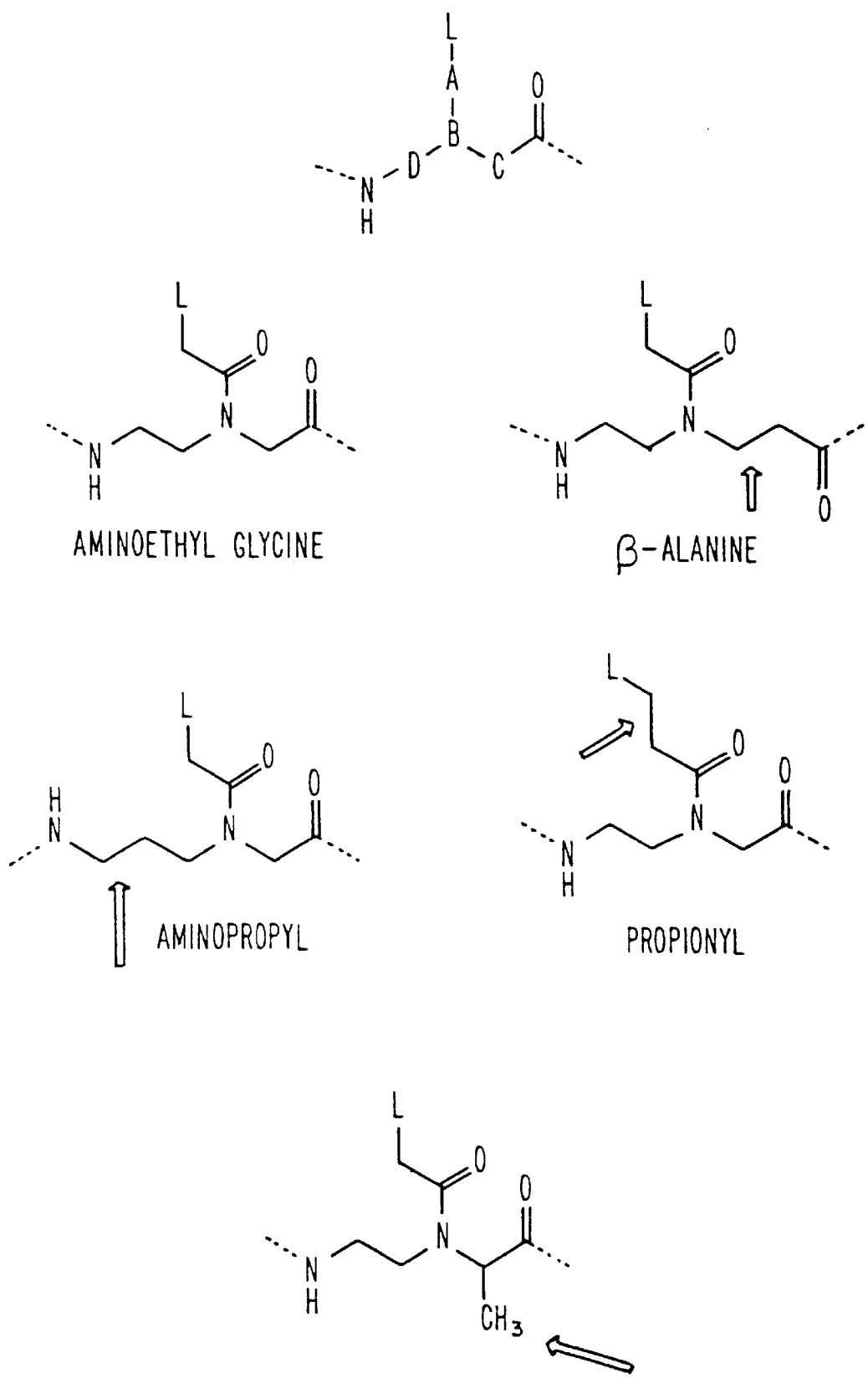
FIG. 16 provides examples of PNA backbone alterations.

Variations of the groups A, C and D (FIG. 16) are demonstrated by the synthesis of monomeric building blocks and incorporation into PNA-oligomers.

Figure 17:
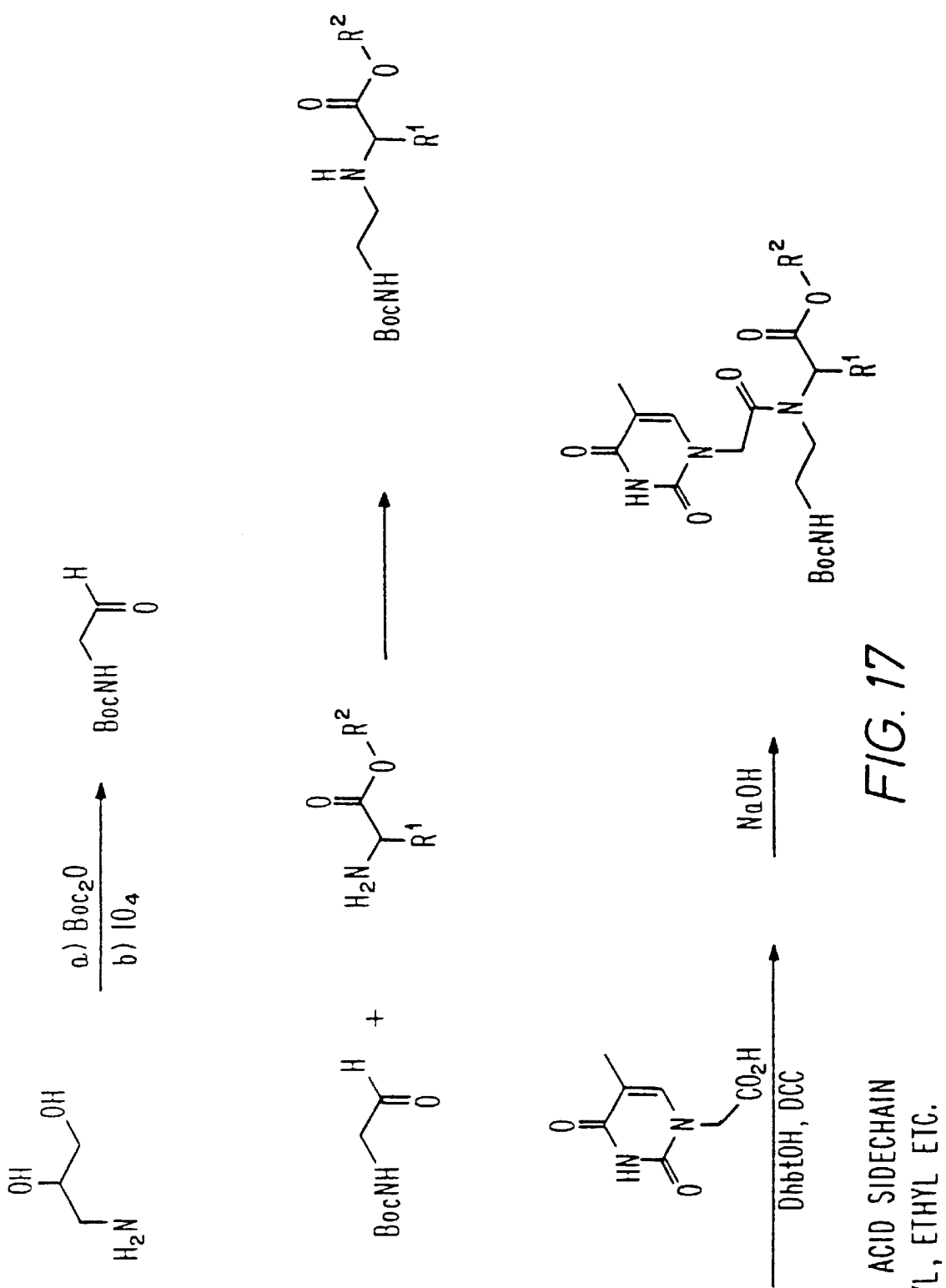
FIG. 17 provides a procedure for synthesis of thymine monomer synthons with side chains corresponding to the normal amino acids.

In one example, the C group was a $CH(CH_3)$ group. The synthesis of the corresponding monomer is outlined in FIG. 17. It involves preparation of Boc-protected 1-amino-2,3-propanediol (Example 35), which is cleaved by periodate to give bocaminoacetaldehyde, which is used directly in the next reaction. The bocaminoacetaldehyde can be condensed with a variety of amines; in Example 36, alanine ethyl ester was used. In Examples 17–19, the corresponding thymine monomers were prepared. The monomer has been incorporated into an 8-mer by the DCC-coupling protocol (Examples 30 and 31).

Figure 18A:
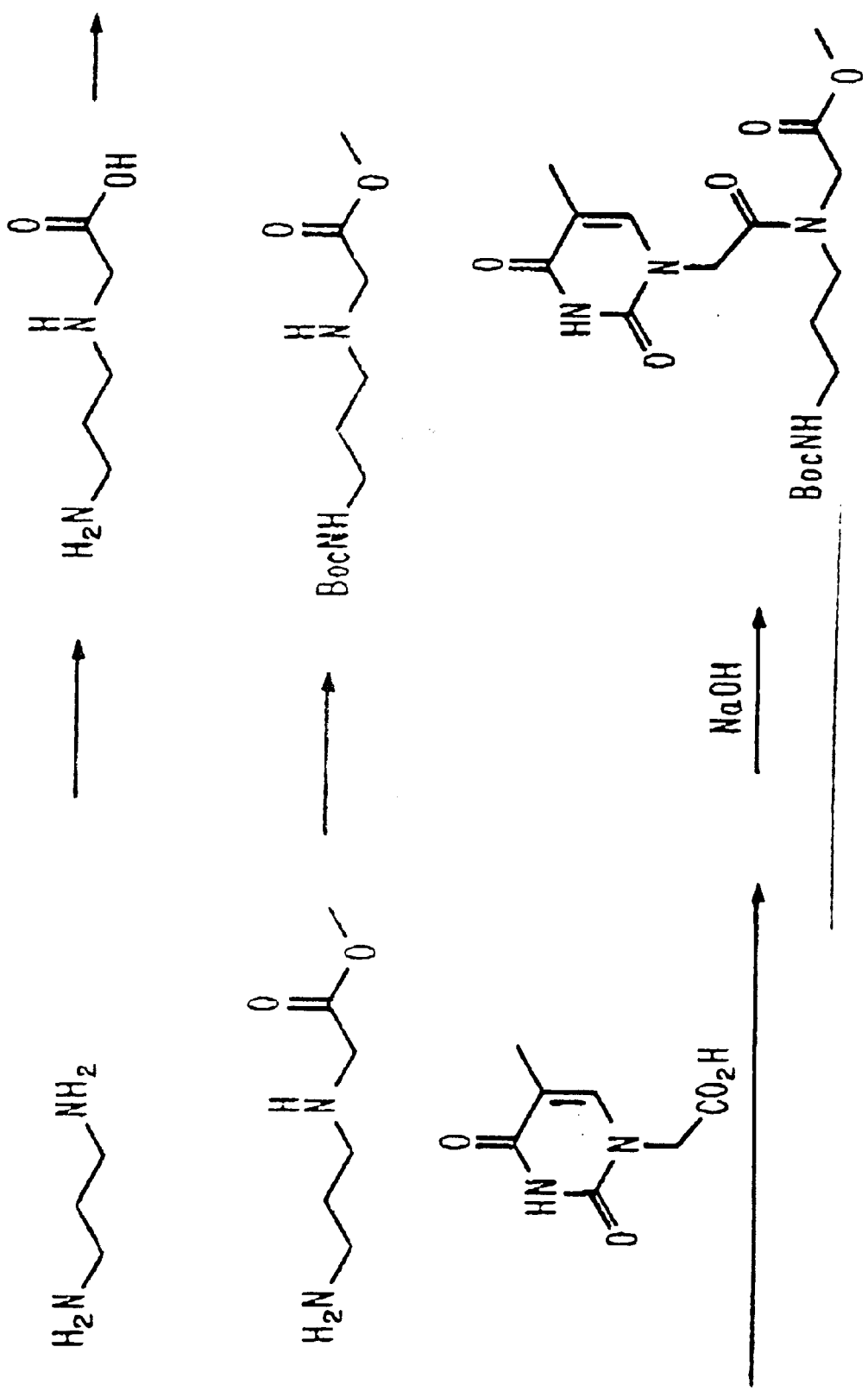
FIGS. 18a and 18b provide procedures for synthesis of an aminopropyl analogue and a propionyl analogue, respectively, of a thymine monomer synthon.
Figure 18B:
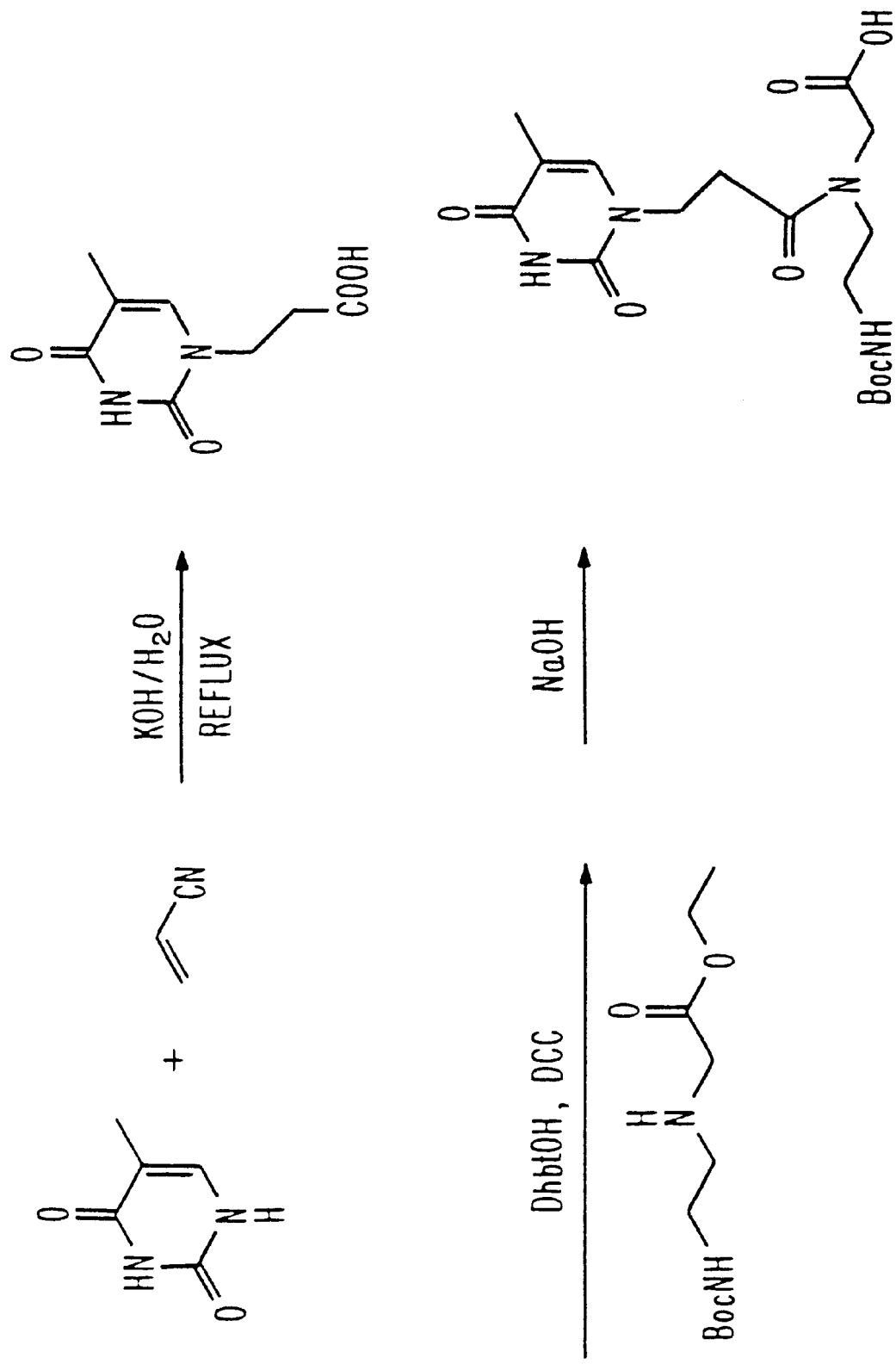

In another example, the D-group is a $(CH_2)_3$ group. The synthesis of the corresponding monomer is outlined in FIG. 18.A and described in Examples 40 and 46.

In another example, the A-group is a $(CH_2)_2CO$ group. The synthesis of the corresponding thymine monomer is outlined FIG. 18.B and Examples 42 through 45.

Figure 19:
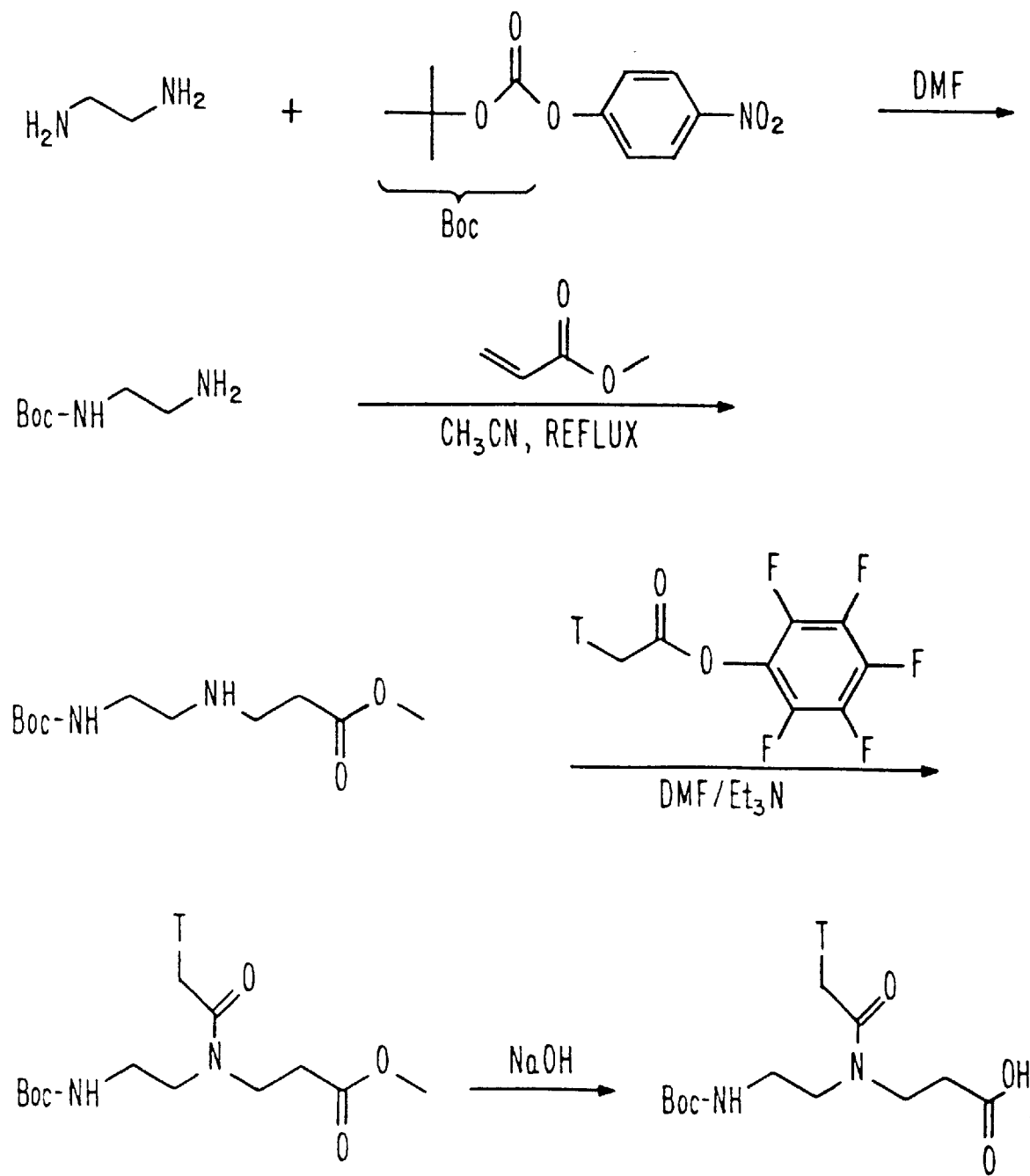
FIG. 19 provides a procedure for synthesis of an aminoethyl-β-alanine analogue of thymine monomer synthon.

In yet another example, the C-group is a $(CH_2)_2$ group. The synthesis of the thymine and protected cytosine monomer is outlined in FIG. 19 and Examples 46 through 51. Hybridization experiments with a PNA-oligomer containing one unit are described in Example 61, which shows a significant lowering of affinity but a retention of specificity.

EXAMPLE 1 tert-Butyl 4-nitrophenyl carbonate

Sodium carbonate (29.14 g; 0.275 mol) and 4-nitrophenol (12.75 g; 91.6 mmol) were mixed with dioxane (250 ml). Boc-anhydride (20.0 g; 91.6 mmol) was transferred to the mixture with dioxane (50 ml). The mixture was refluxed for 1 h, cooled to 0° C., filtered and concentrated to ⅓, and then poured into water (350 ml) at 0° C. After stirring for ½ h., the product was collected by filtration, washed with water, and then dried over sicapent, in vacuo. Yield 21.3 g (97%). M.p. 73.0–74.5° C. (litt. 78.5–79.5° C.). Anal. for $C_{11}H_{13}NO_5$ found(calc.) C: 55.20(55.23) H: 5.61(5.48) N: 5.82(5.85).

EXAMPLE 2

(N'-Boc-2'-aminoethyl)glycine (2)

The title compound was prepared by a modification of the procedure by Heimer, et al. N-(2-Aminoethyl)glycine (1, 3.00 g; 25.4 mmol) was dissolved in water (50 ml), dioxane (50 ml) was added, and the pH was adjusted to 11.2 with 2 N sodium hydroxide. tert-Butyl-4-nitrophenyl carbonate (7.29 g; 30.5 mmol) was dissolved in dioxane (40 ml) and added dropwise over a period of 2 h, during which time the pH was maintained at 11.2 with 2 N sodium hydroxide. The pH was adjusted periodically to 11.2 for three more hours and then the solution was left overnight. The solution was cooled to 0° C. and the pH was carefully adjusted to 3.5 with 0.5 M hydrochloric acid. The aqueous solution was washed with chloroform (3×200 ml), the pH adjusted to 9.5 with 2N sodium hydroxide and the solution was evaporated to dryness, in vacuo (14 mmHg). The residue was extracted with DMF (25+2×10 ml) and the extracts filtered to remove excess salt. This results in a solution of the title compound in about 60% yield and greater than 95% purity by tlc (system 1 and visualised with ninhydrin, Rf=0.3). The solution was used in the following preparations of Boc-aeg derivates without further purification.

EXAMPLE 3

N-1-Carboxymethylthymine (4)

This procedure is different from the literature synthesis, but is easier, gives higher yields, and leaves no unreacted thymine in the product. To a suspension of thymine (3, 40.0 g; 0.317 mol) and potassium carbonate (87.7 g; 0.634 mmol) in DMF (900 ml) was added methyl bromoacetate (30.00 ml; 0.317 mmol). The mixture was stirred vigorously overnight under nitrogen. The mixture was filtered and evaporated to dryness, in vacuo. The solid residue was treated with water (300 ml) and 4 N hydrochloric acid (12 ml), stirred for 15 min at 0° C., filtered, and washed with water (2×75 ml). The precipitate was treated with water (120 ml) and 2N sodium hydroxide (60 ml), and was boiled for 10 minutes. The mixture was cooled to 0° C., filtered, and the pure title compound was precipitated by the addition of 4 N hydrochloric acid (70 ml). Yield after drying, in vacuo over sicapent: 37.1 g (64%). $^1$H-NMR: (90 MHz; DMSO-d$_6$): 11.33 ppm (s,1H, N$\underline{H}$); 7.49(d, J=0.92 Hz, 1H, Ar$\underline{H}$); 4.38 (s, 2H, C$\underline{H}_2$); 1.76 (d, J=0.92 Hz, T—C$\underline{H}_3$)

EXAMPLE 4

N-1-Carboxymethylthymine pentafluorophenyl ester (5)

N-1-Carboxymethylthymine (4, 10.0 g; 54.3 mmol) and pentafluorophenol (10.0 g; 54.3 mmol) were dissolved in DMF (100 ml) and cooled to 5° C. in ice water. DCC (13.45 g; 65.2 mmol) then was added. When the temperature passed below 5° C., the ice bath was removed and the mixture was stirred for 3 h at ambient temperature. The precipitated DCU was removed by filtration and washed twice with DMF (2×10 ml). The combined filtrate was poured into ether (1400 ml) and cooled to 0° C. Petroleum ether (1400 ml) was added and the mixture was left overnight. The title compound was isolated by filtration and was washed thoroughly with petroleum ether. Yield: 14.8 g(78%). The product was pure enough to carry out the next reaction, but an analytical sample was obtained by recrystallization from 2-propanol. M.p. 200.5–206° C. Anal. for $C_{13}H_7F_5N_2O_4$. Found(calc.) C: 44.79(44.59); H: 2.14(2.01) N: 8.13(8.00). FAB-MS: 443 (M+1+glycerol), 351 (M+1). $^1$H-NMR (90 MHz; DMSO-d$_6$): 11.52 ppm (s, 1H, N$\underline{H}$); 7.64 (s, 1H, Ar$\underline{H}$); 4.99 (s, 2H, C$\underline{H}_2$); 1.76 (s, 3H, C$\underline{H}_3$).

EXAMPLE 5

1-(Boc-aeg)thymine (6)

To the DMF-solution from above was added triethyl amine (7.08 ml; 50.8 mmol) followed by N-1-carboxymethylthymine pentafluorophenyl ester (5, 4.45 g; 12.7 mmol). The resultant solution was stirred for 1 h. The solution was cooled to 0° C. and treated with cation exchange material ("Dowex 50W X-8", 40 g) for 20 min. The cation exchange material was removed by filtration, washed with dichloromethane (2×15 ml), and dichloromethane (150 ml) was added. The resulting solution was washed with saturated sodium chloride, dried over magnesium sulfate, and evaporated to dryness, in vacuo, first by a water aspirator and then by an oil pump. The residue was shaken with water (50 ml) and evaporated to dryness. This procedure was repeated once. The residue then was dissolved in methanol (75 ml) and poured into ether (600 ml) and petroleum ether (1.4 L). After stirring overnight, the white solid was isolated by filtration and was washed with petroleum ether. Drying over sicapent, in vacuo, gave 3.50 g (71.7%). M.p. 142–147° C. Anal. for $C_{16}H_{24}N_4O_7$. Found (calc.) C: 49.59(50.00) H: 6.34(6.29) N: 14.58(14.58). $^1$H-NMR (250 MHz, DMSO-d$_6$): Due to the limited rotation around the secondary amide bond several of the signals were doubled in the ratio 2:1,(indicated in the list by mj. for major and mi. for minor). 12.73 ppm (b, 1H, —CO$_2$H); 11.27 ppm (s, mj., imide); 11.25 ppm (s, mi., imide); 7.30 ppm (s, mj., ArH); 7.26 ppm (s, mi., ArH); 6.92 ppm (unres. t, mj., BocNH); 6.73 ppm (unres. t; mi., BocNH); 4.64 ppm (s, mj., T—CH$_2$—CO—); 4.47 ppm (s, mi., T—CH$_2$—CO—); 4.19 ppm (s, mi., CONRC$\underline{H}_2$CO$_2$H); 3.97 ppm (s, mj., CONRC$\underline{H}_2$CO$_2$H); 3.41–2.89 ppm (unres. m, —CH$_2$CH$_2$— and water); 1.75 ppm (s, 3H, T—CH$_3$); 1.38 ppm (s, 9H, t-Bu). $^{13}$C-NMR: 170.68 ppm (CO); 170.34 (CO); 167.47 (CO); 167.08 (CO); 164.29 (CO); 150.9 (C5"); 141.92 (C6"); 108.04 (C2'); 77.95 and 77.68 (Thy-C$\underline{H}_2$CO); 48.96, 47.45 and 46.70 (—$\underline{C}$H$_2$$\underline{C}$H$_2$— and NC$\underline{H}_2$CO$_2$H); 37.98 (Thy-C$\underline{H}_3$); 28.07 (t-Bu). FAB-MS: 407 (M+Na$^+$); 385 (M+H$^+$).

EXAMPLE 6

1-(Boc-aeg)thymine pentafluorophenyl ester (7, Boc-Taeg.OPfp)

1-(Boc-aeg)thymine (6) (2.00 g; 5.20 mmol) was dissolved in DMF (5 ml) and methylene chloride (15 ml) was added. Pentafluorophenol (1.05 g; 5.72 mmol) was added and the solution was cooled to 0° C. in an ice bath. DDC then was added (1.29 g; 6.24 mmol) and the ice bath was removed after 2 min. After 3 h with stirring at ambient temperature, the precipitated DCU was removed by filtration and washed with methylene chloride. The combined filtrate was washed twice with aqueous sodium hydrogen carbonate and once with saturated sodium chloride, dried over magnesium sulfate, and evaporated to dryness, in vacuo. The solid residue was dissolved in dioxane (150 ml) and poured into water (200 ml) at 0° C. The title compound was isolated by filtration, washed with water, and dried over sicapent, in vacuo. Yield: 2.20 g (77%). An analytical sample was obtained by recrystallisation from 2-propanol. M.p. 174–175.5° C. Analysis for $C_{22}H_{23}N_4O_7F_5$, found(calc.): C: 48.22(48.01); H: 4.64(4.21); N: 9.67(10.18). $^1$H-NMR (250 MHz, CDCl$_3$): Due to the limited rotation around the secondary amide bond several of the signals were doubled in the ratio 6:1 (indicated in the list by mj. for major and mi. for minor). 7.01 ppm (s, mi., ArH); 6.99 ppm (s, mj., ArH); 5.27 ppm (unres. t, BocN$\underline{H}$); 4.67 ppm (s, mj., T—CH$_2$—CO—); 4.60 ppm (s, mi., T—CH$_2$—CO—); 4.45 ppm (s, mj., CONRC$\underline{H}_2$CO$_2$Pfp); 4.42 ppm (s, mi., CONRC$\underline{H}_2$CO$_2$Pfp); 3.64 ppm (t,2H, BocNHCH$_2$C$\underline{H}_2$—); 3.87 ppm ("q",2H, BocNHC$\underline{H}_2$CH$_2$—); 1.44(s, 9H, t-Bu). FAB-MS: 551 (10; M+1); 495 (10; M+1-tBu); 451 (80; -Boc).

EXAMPLE 7

N$^4$-Benzyloxycarbonyl cytosine (9)

Over a period of about 1 h, benzyloxycarbonyl chloride (52 ml; 0.36 mol) was added dropwise to a suspension of cytosine (8, 20.0 g; 0.18 mol) in dry pyridine (1000 ml) at 0° C. under nitrogen in oven-dried equipment. The solution then was stirred overnight, after which the pyridine suspension was evaporated to dryness, in vacuo. Water (200 ml) and 4 N hydrochloric acid were added to reach pH ~1. The resulting white precipitate was filtered off, washed with water and partially dried by air suction. The still-wet precipitate was boiled with absolute ethanol (500 ml) for 10 min, cooled to 0° C., filtered, washed thoroughly with ether, and dried, in vacuo. Yield 24.7 g (54%). M.p.>250° C. Anal. for $C_{12}H_{11}N_3O_3$. Found(calc.); C: 58.59(58.77); H: 4.55 (4.52); N: 17.17(17.13). No NMR spectra were recorded since it was not possible to get the product dissolved.

EXAMPLE 8

$N^4$-Benzyloxycarbonyl-$N^1$-carboxymethyl cytosine (10)

In a three necked round bottomed flask equipped with mechanical stirring and nitrogen coverage was placed methyl bromacetate (7.82 ml; 82.6 mmol) and a suspension of $N^4$-benzyloxycarbonyl-cytosine (9, 21.0 g; 82.6 mmol) and potassium carbonate (11.4 g; 82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish colour. M.p. 266–274° C. Anal. for $C_{14}H_{13}N_3O_5$. Found(calc.); C: 55.41 (55.45); H: 4.23(4.32); N: 14.04(13.86). $^1$H-NMR (90 MHz; DMSO-$d_6$): 8.02 ppm (d, J=7.32 Hz, 1H, H-6); 7.39(s, 5H, Ph); 7.01(d, J=7.32 Hz, 1H, H-5); 5.19 (s, 2H, PhC$\underline{H}_2$—); 4.52 (s, 2H).

EXAMPLE 9

$N^4$-Benzyloxycarbonyl-$N^1$-carboxymethyl-cytosine pentafluorophenyl ester (11)

$N^4$-Benzyloxycarbonyl-$N^1$-carboxymethyl-cytosine (10, 4.00 g; 13.2 mmol) and pentafluorophenol (2.67 g; 14.5 mmol) were mixed with DMF (70 ml), cooled to 0° C. with ice-water, and DCC (3.27 g; 15.8 mmol) was added. The ice bath was removed after 3 min and the mixture was stirred for 3 h at room temperature. The precipitated DCU was removed by filtration, washed with DMF, and the filtrate was evaporated to dryness, in vacuo (0.2 mmHg). The solid residue was treated with methylene chloride (250 ml), stirred vigorously for 15 min, filtered, washed twice with diluted sodium hydrogen carbonate and once with saturated sodium chloride, dried over magnesium sulfate, and evaporated to dryness, in vacuo. The solid residue was recrystallized from 2-propanol (150 ml) and the crystals were washed thoroughly with ether. Yield 3.40 g (55%). M.p. 241–245° C. Anal. for $C_{20}H_{12}N_3F_5O_5$. Found(calc.); H: 2.77(2.58); N: 9.24(8.95). $^1$H-NMR (90 MHz; CDCl$_3$): 7.66 ppm (d, J=7.63 Hz, 1H, H-6); 7.37(s, 5H, Ph); 7.31(d, J=7.63 Hz, 1H, H-5); 5.21 (s, 2H, PhC$\underline{H}_2$—); 4.97 (s, 2H, NC$\underline{H}_2$—). FAB-MS: 470 (M+1)

EXAMPLE 10

$N^4$-Benzyloxycarbonyl-1-Boc-aeg-cytosine (12)

To a solution of (N-Boc-2-aminoethyl)glycine (2) in DMF, prepared as described above, was added triethyl amine (7.00 ml; 50.8 mmol) and $N^4$-benzyloxycarbonyl-$N^1$-carboxymethylcytosine pentafluorophenyl ester (11, 2.70 g; 5.75 mmol). After stirring the solution for 1 h at room temperature, methylene chloride (150 ml), saturated sodium chloride (250 ml), and 4 N hydrochloric acid to pH ~1 were added. The organic layer was separated and washed twice with saturated sodium chloride, dried over magnesium sulfate, and evaporated to dryness, in vacuo, first with a water aspirator and then with an oil pump. The oily residue was treated with water (25 ml) and was again evaporated to dryness, in vacuo. This procedure then was repeated. The oily residue (2.80 g) was then dissolved in methylene chloride (100 ml), petroleum ether (250 ml) was added, and the mixture was stirred overnight. The title compound was isolated by filtration and washed with petroleum ether. Tlc (system 1) indicated substantial quantities of pentafluorophenol, but no attempt was made to remove it. Yield: 1.72 g (59%). M.p. 156° C.(decomp.). $^1$H-NMR (250 MHz, CDCl$_3$): Due to the limited rotation around the secondary amide bond several of the signals were doubled in the ratio 2:1,(indicated in the list by mj. for major and mi. for minor). 7.88 ppm (dd, 1H, H-6); 7.39 (m, 5H, Ph); 7.00 (dd, 1H, H-5); 6.92 (b, 1H, BocN$\underline{H}$); 6.74 (b, 1H, ZN$\underline{H}$)-?; 5.19 (s, 2H, Ph—C$\underline{H}_3$); 4.81 ppm (s, mj., Cyt-CH$_2$—CO—); 4.62 ppm (s, mi., Cyt-CH$_2$—CO—); 4.23 (s, mi., CONRC$\underline{H}_2$CO$_2$H); 3.98 ppm (s, mj., CONRC$\underline{H}_2$CO$_2$H); 3.42–3.02 (unres. m, —CH$_2$CH$_2$— and water); 1.37 (s, 9H, tBu). FAB-MS: 504 (M+1); 448 (M+1-tBu).

EXAMPLE 11

$N^4$-Benzyloxycarbonyl-1-Boc-aeg-cytosine pentafluorophenyl ester (13)

$N^4$-Benzyloxycarbonyl-1-Boc-aeg-cytosine (12, 1.50 g; 2.98 mmol) and pentafluorophenol (548 mg; 2.98 mmol) was dissolved in DMF (10 ml) Methylene chloride (10 ml) was added, the reaction mixture was cooled to 0° C. in an ice bath, and DCC (676 mg; 3.28 mmol) was added. The ice bath was removed after 3 min and the mixture was stirred for 3 h at ambient temperature. The precipitate was isolated by filtration and washed once with methylene chloride. The precipitate was dissolved in boiling dioxane (150 ml) and the solution was cooled to 15° C., whereby DCU precipitated. The DCU was removed by filtration and the resulting filtrate was poured into water (250 ml) at 0° C. The title compound was isolated by filtration, was washed with water, and dried over sicapent, in vacuo. Yield 1.30 g (65%). Analysis for $C_{29}H_{28}N_5O_8F_5$. Found(calc.); C: 52.63(52.02); H: 4.41(4.22); N: 10.55(10.46). $^1$H-NMR (250 MHz; DMSO-$d_6$): showed essentially the spectrum of the above acid, most probably due to hydrolysis of the ester. FAB-MS: 670 (M+1); 614 (M+1-tBu)

EXAMPLE 12

4-Chlorocarboxy-9-chloroacridine

4-Carboxyacridone (6.25 g; 26.1 mmol), thionyl chloride (25 ml), and 4 drops af DMF were heated gently under a flow of nitrogen until all solid material had dissolved. The solution then was refluxed for 40 min. The solution was cooled and excess thionyl chloride was removed in vacuo.

The last traces of thionyl chloride were removed by coevaporation with dry benzene (dried over Na—Pb) twice. The remaining yellow powder was used directly in the next reaction.

EXAMPLE 13

4-(5-Methoxycarbonylpentylamidocarbonyl)-9-chloroacridine

Methyl 6-aminohexanoate hydrochloride (4.70 g; 25.9 mmol) was dissolved in methylene chloride (90 ml), cooled to 0° C., triethyl amine (15 ml) was added, and the resulting solution then was immediately added to the acid chloride from above. The round bottomed flask containing the acid chloride was cooled to 0° C. in an ice bath. The mixture was stirred vigorously for 30 min at 0° C. and 3 h at room temperature. The resulting mixture was filtered to remove the remaining solids, which were washed with methylene chloride (20 ml). The red-brown methylene chloride filtrate was subsequently washed twice with saturated sodium hydrogen carbonate, once with saturated sodium chloride, dried over magnesium sulfate, and evaporated to dryness, in vacuo. To the resulting oily substance was added dry benzene (35 ml) and ligroin (60–80° C., dried over Na—Pb). The mixture was heated to reflux. Activated carbon and celite were added and mixture was refluxed for 3 min. After filtration, the title compound crystallised upon cooling with magnetic stirring. It was isolated by filtration and washed with petroleum ether. The product was stored over solid potassium hydroxide. Yield 5.0 g (50%).

EXAMPLE 14

4-(5-Methoxycarbonylpentyl)amidocarbonyl-9-[6'-(4"-nitrobenzamido)hexylamino]-aminoacridine 4-(5-Methoxycarbonylpentylamidocarbonyl)-9-chloroacridine (1.30 g; 3.38 mmol) and phenol (5 g) were heated to 80° C. for 30 min under a flow of nitrogen, after which 6-(4'-nitrobenzamido)-1-hexylamine (897 mg; 3.38 mmol) was added. The temperature raised to 120° C. for 2 h. The reaction mixture was cooled and methylene chloride (80 ml) was added. The resulting solution was washed three times with 2N sodium hydroxide (60 ml portions) and once with water, dried over magnesium sulfate, and evaporated to dryness, in vacuo. The resulting red oil (1.8 g) was dissolved in methylene chloride (40 ml), cooled to 0° C. Ether (120 ml) was added and the resultant solution was stirred overnight. This results in a mixture of solid material and an oil. The solid was isolated by filtration. The solid and the oil were re-dissolved in methylene chloride (80 ml) and added dropwise to cold ether (150 ml). After 20 minutes of stirring, the title compound was isolated by filtration in the form of orange crystals. The product was washed with ether and dried in vacuo over potassium hydroxide. Yield 1.60 g (77%). M.p. 145–147° C.

EXAMPLE 15

4-(5-Carboxypentyl)amidocarbonyl-9-[6'-(4"-nitrobenzamido)-hexylamino]-aminoacridine 4-(5-Methoxycarbonylpentyl)amidocarbonyl-9-[6'-(4"-nitrobenzamido)hexylamino]aminoacridine (503 mg; 0.82 mmol) was dissolved in DMF (30 ml), and 2 N sodium hydroxide (30 ml) was added. After stirring for 15 min, 2 N hydrochloric acid (35 ml) and water (50 ml) were added at 0° C. After stirring for 30 min, the solution was decanted, leaving an oily substance which was dissolved in boiling methanol (150 ml), filtered and concentrated to ⅓ volume. To the methanol solution were added ether (125 ml) and 5–6 drops of HCl in ethanol. The solution was decanted after 1 h of stirring at 0° C. The oily substance was redissolved in methanol (25 ml) and precipitated with ether (150 ml). The title compound was isolated as yellow crystals after stirring overnight. Yield 417 mg (80%). M.p. 173° C. (decomp.).

EXAMPLE 16

(a) 4-(5-pentafluorophenyloxycarbonylpentyl) amidocarbonyl-9-[6'-(4"-nitrobenzamido) hexylamino]-aminoacridine(Acr$^1$Opfp)

The acid from above (300 mg; 0.480 mmol) was dissolved in DMF (2 ml) and methylene chloride (8 ml) was added. Pentafluorophenol (97 mg; 0.53 mmol), transferred with 2×2 ml of the methylene chloride, was added. The resulting solution was cooled to 0° C. after which DCC (124 mg; 0.60 mmol) was subsequently added. The ice bath was removed after 5 minutes and the mixture was left with stirring overnight. The precipitated DCU was removed by centrifugation and the centrifugate was evaporated to dryness, in vacuo, first by a water aspirator and then by an oil pump. The residue was dissolved in methylene chloride (20 ml), filtered, and evaporated to dryness, in vacuo. The residue was again dissolved in methylene chloride and petroleum ether (150 ml). A 1 ml portion of 5M HCl in ether was added. The solvent was removed by decanting after 30 min of stirring at 0° C. The residual oily substance was dissolved in methylene chloride (100 ml). Petroleum ether (150 ml) was added and the mixture was left with stirring overnight. The next day the yellow precipitated crystalline material was isolated by filtration and was washed with copious amounts of petroleum ether. Yield, after drying, 300 mg (78%). M.p. 97.50° C. (decomp.) All samples showed satisfactory elemental analysis, $^1$H- and $^{13}$C-NMR and mass spectra.

(b) Experimental for the synthesis of PNA compounds, cf. FIG. 8

Materials: Boc-Lys (ClZ), benzhydrylamine-copoly (styrene-1%-divinylbenzene) resin (BHA resin), and p-methylbenzhydrylamine-copoly(styrene-1%-divinylbenzene) resin (MBHA resin) were purchased from Peninsula Laboratories. Other reagents and solvents were: Biograde trifluoroacetic acid from Halocarbon Products; diisopropylethylamine (99%; was not further distilled) and N-acetylimidazole (98%) from Aldrich; H$_2$O was distilled twice; anhydrous HF from Union Carbide; synthesis grade N,N-dimethylformamide and analytical grade methylene chloride (was not further distilled) from Merck; HPLC grade acetonitrile from Lab-Scan; purum grade anisole, N,N'-dicyclohexylcarbodiimide, and puriss. grade 2,2,2-trifluoroethanol from Fluka.

(b) General Methods and Remarks

Except where otherwise stated, the following applies. The PNA compounds were synthezised by the stepwise solid-phase approach (Merrifield, *J. Am. Chem. Soc.*, 1963, 85, 2149) employing conventional peptide chemistry utilizing the TFA-labile tert-butyloxycarbonyl (Boc) group for "temporary" N-protection (Merrifield, *J. Am. Chem. Soc.*, 1964, 86, 304) and the more acid-stable benzyloxycarbonyl (Z) and 2-chlorobenzyloxycarbonyl (ClZ) groups for "permanent" side chain protection. To obtain C-terminal amides, the PNAs were assembled onto the HF-labile BHA or MBHA resins (the MBHA resin has increased susceptibility to the final HF cleavage relative to the unsubstituted BHA resin (Matsueda, et al., *Peptides*, 1981, 2, 45). All reactions (except HF reactions) were carried out in manually operated standard solid-phase reaction vessels fitted with a coarse glass frit (Merrifield, et al., *Biochemistry*, 1982, 21, 5020). The quantitative ninhydrin reaction (Kaiser test), originally developed by Merrifield and co-workers (Sarin, et al., *Anal. Biochem.*, 1981, 117, 147) for peptides containing "normal" amino acids, was successfully applied (see Table I–III) using the "normally" employed effective extinction coefficient $\in = 15000$ M$^{-1}$cm$^{-1}$ for all residues to determine the completeness of the individual couplings as well as to measure the number of growing peptide chains. The theoretical substitution $S_{n-1}$ upon coupling of residue number n (assuming both complete deprotection and coupling as well as neither chain termination nor loss of PNA chains during the synthetic cycle) is calculated from the equation:

$$S_n = S_{n-1} \times (1 + (S_{n-1} \times \Delta MW \times 10^{-3} \text{ mmol/mol}))^{-1}$$

where $\Delta MW$ is the gain in molecular weight ($[\Delta MW] = g/mol$) and $S_{n-1}$ is the theoretical substitution upon coupling of the preceding residue n−1 ($[S] = mmol/g$). The estimated value (%) on the extent of an individual coupling is calculated relative to the measured substitution (unless S was not determined) and include correction for the number of remaining free amino groups following the previous cycle. HF reactions were carried out in a Diaflon HF apparatus from Toho Kasei (Osaka, Japan). Vydac $C_{18}$ (5 μm, 0.46×25 cm and 5 μm, 1.0×25 cm) reverse-phase columns, respectively were used for analytical and semi-preparative HPLC on an SP8000 instrument. Buffer A was 5 vol % acetonitrile in water containing 445 μl trifluoroacetic acid per litre, and buffer B was 60 vol % acetonitrile in water containing 390 μl trifluoroacetic acid per litre. The linear gradient was 0–100% of buffer B in 30 min, flow rates 1.2 ml/min (analytical) and 5 ml/min (semi-preparative). The eluents were monitored at 215 nm (analytical) and 230 nm (semi-preparative). Molecular weights of the PNAs were determined by $^{252}$Cf plasma desorption time-of-flight mass spectrometry from the mean of the most abundant isotopes.

EXAMPLE 17

Solid-Phase Synthesis of Acr$^1$-[Taeg]$_{15}$—NH$_2$ and Shorter Derivatives (a) Stepwise Assembly of Boc-[Taeg]$_{15}$-BHA Resin The synthesis was initiated on 100 mg of preswollen and neutralized BHA resin (determined by the quantitative ninhydrin reaction to contain 0.57 mmol NH$_2$/g) employing single couplings ("Synthetic Protocol 1") using 3.2 equivalents of BocTaeg-OPfp in about 33% DMF/CH$_2$Cl$_2$. The individual coupling reactions were carried out by shaking for at least 12 h in a manually operated 6 ml standard solid-phase reaction vessel and unreacted amino groups were blocked by acetylation at selected stages of the synthesis. The progress of chain elongation was monitored at several stages by the quantitative ninhydrin reaction (see Table I). Portions of protected Boc-[Taeg]$_5$-BHA, Boc-[Taeg]$_{10}$-BHA, and Boc-[Taeg]$_{15}$-BHA resins were taken out after assembling 5, 10, and 15 residues, respectively.

| Syn- thetic Step | Residue Coupled | Substitution After Deprotection (mmol/g) | | Remaining Free Amino Groups After (μmol/g) | | Estimated Extent of Coupling (%) |
|---|---|---|---|---|---|---|
| | | Measd | Theo- retol | Single Coupling | Acetyl- ation | |
| "0" | | 0.57 | | | | |
| 1 | BocTaeg | ND | 0.50 | 1.30 | | <99.7 |
| 2 | BocTaeg | ND | 0.44 | 1.43 | | <99.9 |
| 3 | BocTaeg | 0.29 | 0.39 | 3.33 | | 99.3 |
| 4 | BocTaeg | 0.27 | 0.35 | 13.30 | | 96.3 |
| 5 | BocTaeg | 0.26 | 0.32 | 8.33 | | >99.9 |
| 6 | BocTaeg | ND | 0.30 | 7.78 | | >99.9 |
| 7 | BocaTeg | ND | 0.28 | 13.81 | 7.22 | <97.8 |
| 8 | BocTaeg | ND | 0.26 | 14.00 | | <99.9 |
| 9 | BocTaeg | ND | 0.24 | 30.33 | | 93.2 |
| 10 | BocTaeg | 0.16 | 0.23 | 11.67 | 2.67 | >99.9 |
| 11 | BocTaeg | ND | 0.21 | 4.58 | | >99.9 |
| 12 | BocTaeg | ND | 0.20 | 5.87 | | <99.4 |
| 13 | BocTaeg | ND | 0.19 | 1.67 | | >99.9 |
| 14 | BocTaeg | ND | 0.18 | 14.02 | | <93.1 |
| 15 | BocTaeg | 0.07 | 0.17 | 4.20 | 3.33 | >99.9 |

(b) Synthesis of Acr$^1$-[Taeg]$_{15}$-BHA Resin

Following deprotection of the residual Boc-[Taeg]$_{15}$-BHA resin (estimated dry weight is about 30 mg; ~0.002 mmol growing chains), the H—[Taeg]$_{15}$-BHA resin was reacted with about 50 equivalents (80 mg; 0.11 mmol) of Acr$^1$-OPfp in 1 ml of about 66% DMF/CH$_2$Cl$_2$ (i.e., a 0.11 M solution of the pentafluorophenylester) in a 3 ml solid-phase reaction vessel. As judged by a qualitative ninhydrin reaction, coupling of the acridine moiety was close to quantitative.

(c) Cleavage, Purification, and Identification of H—[Taeg] 5—NH$_2$

A portion of protected Boc-[Taeg]$_5$-BHA resin was treated with 50% trifluoroacetic acid in methylene chloride to remove the N-terminal Boc group (which is a precursor of the potentially harmful tert-butyl cation) prior to the HF cleavage. Following neutralization and washing (performed in a way similar to those of steps 2–4 in "Synthetic Protocol 1"), and drying for 2 h in vacuum, the resulting 67.1 mg (dry weight) of H—[Taeg]$_5$-BHA resin was cleaved with 5 ml of HF:anisole (9:1, v/v) stirring at 0° C. for 60 min. After removal of HF, the residue was stirred with dry diethyl ether (4×15 ml, 15 min each) to remove anisole, filtered under gravity through a fritted glass funnel, and dried. The PNA was then extracted into a 60 ml (4×15 ml, stirring 15 min each) 10% aqueous acetic acid solution. Aliquots of this solution were analyzed by analytical reverse-phase HPLC to establish the purity of the crude PNA. The main peak at 13.0 min accounted for about 93% of the total absorbance. The remaining solution was frozen and lyophilized to afford about 22.9 mg of crude material. Finally, 19.0 mg of the crude product was purified from five batches, each containing 3.8 mg in 1 ml of H$_2$O. The main peak was collected by use of a semi-preparative reverse-phase column. Acetonitrile was removed on a speed vac and the residual solution was frozen (dry ice) and subsequently lyophilized to give 13.1 mg of >99% pure H—[Taeg]$_5$—NH$_2$. The PNA molecule readily dissolved in water and had the correct molecular weight based on mass spectral determination. For (M+H)$^+$ the calculated m/z value was 1349.3 and the measured m/z value was 1347.8.

(d) Cleavage, Purification, and Identification of H—[Taeg]$_{10}$ —NH$_2$

A portion of protected Boc-[Taeg]$_{10}$-BHA resin was treated as described in section (c) to yield 11.0 mg of crude material upon HF cleavage of 18.9 mg dry H—[Taeg]$_{10}$-BHA resin. The main peak at 15.5 min accounted for about 53% of the total absorbance. About 1 mg of the crude product was purified repeatedly (for reasons described below) to give approximately 0.1 mg of at least 80% but presumably >99% pure H—[Taeg]$_{10}$-NH$_2$. A rather broad tail eluting after the target peak and accounting for about 20% of the total absorbance could not be removed (only slightly reduced) upon the repeated purification. Judged by the mass spectrum, which only confirms the presence of the correct molecular weight H—[Taeg]$_{10}$—NH$_2$, the tail phenomonen is ascribed to more or less well-defined aggregational/conformational states of the target molecule. Therefore, the crude product is likely to contain more than the above-mentioned 53% of the target molecule. H—[Taeg]$_{10}$—NH$_2$ is readily dissolved in water. For (M+H)$^+$ the calculated m/z value was 2679.6 and the measured m/z value was 2681.5.

(e) Cleavage, Purification, and Identification of H—[Taeg]$_{15}$—NH$_2$

A portion of protected Boc-[Taeg]$_{15}$-BHA resin was treated as described in section (c) to yield 3.2 mg of crude material upon HF cleavage of 13.9 mg dry H—[Taeg]$_{15}$-BHA resin. The main peak at 22.6 min was located in a broad bulge accounting for about 60% of the total absorbance (FIG. 12a). Again (see the preceding section), this bulge is ascribed to aggregational/conformational states of the target molecule H—[Taeg]$_{15}$—NH$_2$ since mass spectral analysis of the collected "bulge" did not significantly reveal the presence of other molecules. All of the crude product was purified collecting the "bulge" to give approximately 2.8 mg material. For (M+Na)$^+$ the calculated m/z value was 4033.9 and the measured m/z value was 4032.9.

(f) Cleavage, Purification, and Identification of Acr$^1$-[Taeg]$_{15}$—NH$_2$.

Figure 12B:
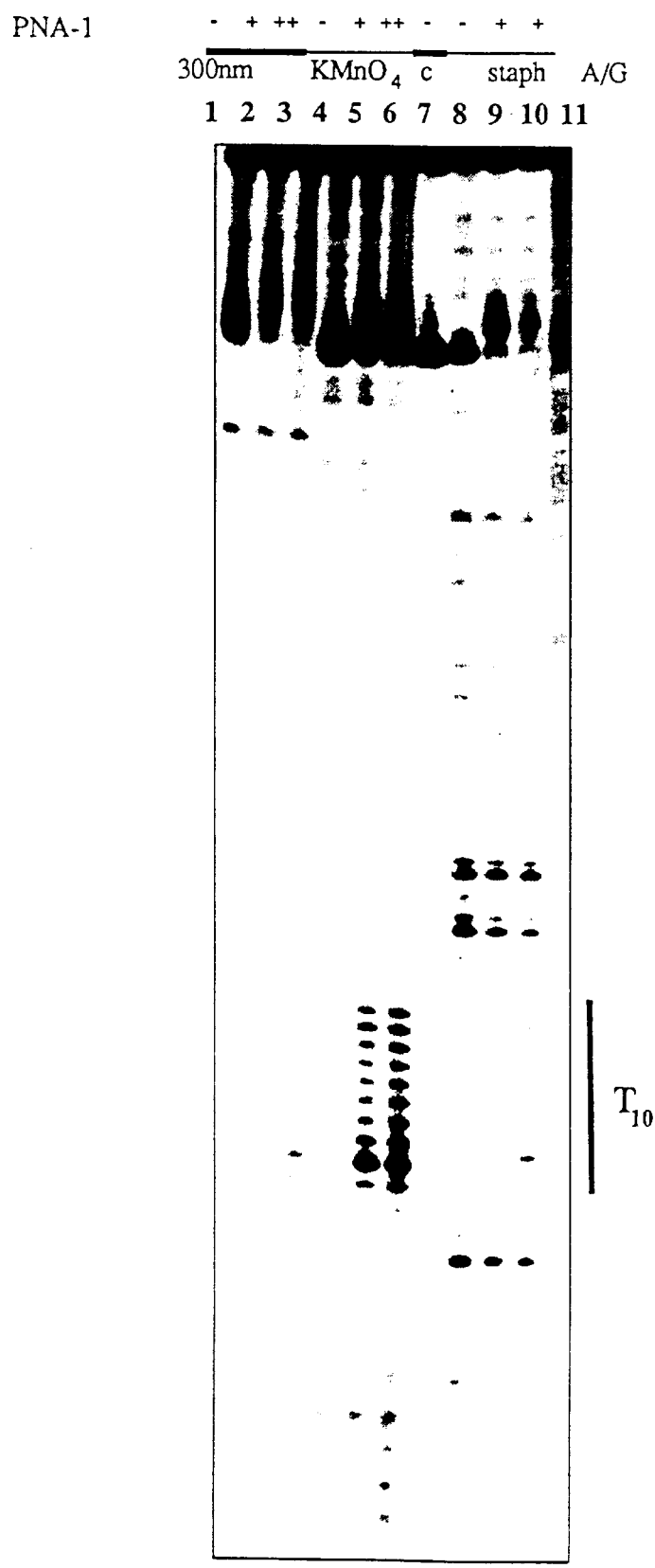
Figure 12C:
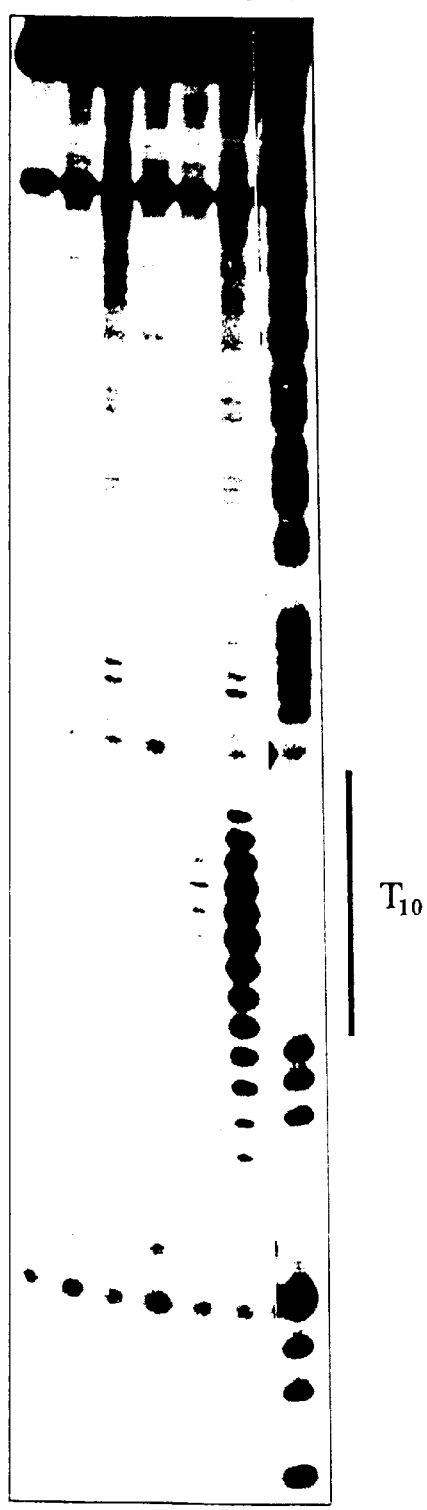

A portion of protected Acr$^1$-[Taeg]$_5$-BHA resin was treated as described in section (b) to yield 14.3 mg of crude material upon HF cleavage of 29.7 mg dry Acr$^1$-[Taeg]$_{15}$-BHA resin. Taken together, the main peak at 23.7 min and a "dimer" (see below) at 29.2 min accounted for about 40% of the total absorbance (FIG. 12b). The crude product was purified repeatedly to give approximately 1 mg of presumably >99% pure Acr$^1$-[Taeg]$_{15}$—NH$_2$ "contaminated" with self-aggregated molecules eluting at 27.4 min, 29.2 min, and finally as a huge broad bulge eluting with 100% buffer B (FIG. 12c). This interpretation is in agreement with the observation that those peaks grow upon standing (for hours) in aqueous acetic acid solution, and finally precipitate out quantitatively. For (M+H)$^+$ the calculated m/z value was 4593.6 and the measured m/z value was 4588.7.

(g) Synthetic Protocol 1

(1) Boc-deprotection with TFA/CH$_2$Cl$_2$ (1:1, v/v), 3 ml, 3×1 min and 1×30 min; (2) washing with CH$_2$Cl$_2$, 3 ml, 6×1 min; (3) neutralization with DIEA/CH$_2$Cl$_2$ (1:19, v/v.), 3 ml, 3×2 min; (4) washing with CH$_2$Cl$_2$, 3 ml, 6×1 min, and drain for 1 min; (5) 2–5 mg sample of PNA-resin may be taken out and dried thoroughly for a quantitative ninhydrin analysis to determine the substitution; (6) addition of 3.2 equiv. (0.18 mmol; 100 mg) BocTaeg-OPfp dissolved in 1 ml CH$_2$Cl$_2$ followed by addition of 0.5 ml DMF (final concentration of pentafluorophenylester ~0.12 M); the coupling reaction was allowed to proceed for a total of 12–24 h shaking at room temperature; (7) washing with DMF, 3 ml, 1×2 min; (8) washing with CH$_2$Cl$_2$, 3 ml, 4×1 min; (9) neutralization with DIEA/CH$_2$Cl$_2$ (1:19, v/v), 3 ml, 2×2 min; (10) washing with CH$_2$Cl$_2$, 3 ml, 6×1 min; (11) 2–5 mg sample of protected PNA-resin is taken out for a rapid qualitative ninhydrin test and further 2–5 mg is dried thoroughly for a quantitative ninhydrin analysis to determine the extent of coupling (after cycles 7, 10, and 15 unreacted amino groups were blocked by acetylation with N-acetylimidazol in methylene chloride).

EXAMPLE 18

Solid-Phase Synthesis of Acr$^1$-[Taeg]$_{15}$-Lys-NH$_2$ and Shorter Derivatives (a) Stepwise Assembly of Boc-[Taeg]$_{15}$-Lys(ClZ)-BHA Resin The synthesis was initiated by a quantitative loading (standard DCC in situ coupling in neat CH$_2$Cl$_2$) of Boc-Lys (ClZ) onto 100 mg of preswollen and neutralized BHA resin (0.57 mmol NH$_2$/g). Further extension of the protected PNA chain employed single couplings ("Synthetic Protocol 2") for cycles 1 to 5 and cycles 10 to 15 using 3.2 equivalents of BocTaeg-OPfp in about 33% DMF/CH$_2$Cl$_2$. Cycles 5 to 10 employed an extra straight DCC (i.e., in situ) coupling of the free acid BocTaeg-OH in about 33% DMF/CH$_2$Cl$_2$. All coupling reactions were carried out by shaking for at least 12 h in a manually operated 6 ml standard solid-phase reaction vessel. Unreacted amino groups were blocked by acetylation at the same stages of the synthesis, as was done in Example 17. Portions of protected Boc-[Taeg]$_5$-Lys(ClZ)-BHA and Boc-[Taeg]$_{10}$-Lys(ClZ)-BHA resins were taken out after assembling 5 and 10 PNA residues, respectively. As judged by the analytical HPLC chromatogram of the crude cleavage product from the Boc-[Taeg]$_{10}$-Lys(ClZ)-BHA resin (see section (e)), an additional "free acid" coupling of PNA residues 5 to 10 gave no significant improvement of the synthetic yield as compared to the throughout single-coupled residues in Example 17.

(b) Synthesis of Acr$^1$-[Taeg]$_{10}$-Lys(ClZ)-BHA Resin

Following deprotection of a portion of Boc-[Taeg]$_{10}$-Lys (ClZ)-BHA resin (estimated dry weight is about 90 mg; ~0.01 mmol growing chains), the H—[Taeg]$_{15}$-BHA resin was reacted with about 20 equivalents (141 mg; 0.19 mmol) of Acr$^1$-OPfp in 1 ml of about 66% DMF/CH$_2$Cl$_2$ in a 3 ml solid-phase reaction vessel. As judged by a qualitative ninhydrin reaction, coupling of the acridine moiety was close to quantitative.

(c) Synthesis of Acr$^1$-[Taeg]$_{15}$-Lys(ClZ)-BHA Resin

Following deprotection of the residual Boc-[Taeg]$_{15}$-Lys (ClZ)-BHA resin (estimated dry weight about 70 mg; ~0.005 mmol growing chains), the H—[Taeg]$_{15}$-Lys(ClZ)-BHA resin was reacted with about 25 equivalents (91 mg; 0.12 mmol) of Acr$^1$-OPfp in 1 ml of about 66% DMF/CH$_2$Cl$_2$ in a 3 ml solid-phase reaction vessel. As judged by a qualitative ninhydrin reaction, coupling of the acridine moiety was close to quantitative.

(d) Cleavage, Purification, and Identification of H—[Taeg]$_5$-Lys-NH$_2$

A portion of protected Boc-[Taeg]$_5$-Lys(ClZ)-BHA resin was treated as described in Example 17c to yield 8.9 mg of crude material upon HF cleavage of 19.0 mg dry H—[Taeg]$_5$-Lys(ClZ)-BHA resin. The main peak at 12.2 min (eluted at 14.2 min if injected from an aqueous solution instead of the 10% aqueous acetic acid solution) accounted for about 90% of the total absorbance. About 2.2 mg of the crude product was purified to give approximately 1.5 mg of 99% pure H—[Taeg]$_5$-Lys-NH$_2$.

(e) Cleavage, Purification, and Identification of H—[Taeg]$^{10}$-Lys-NH$_2$

Figure 13:
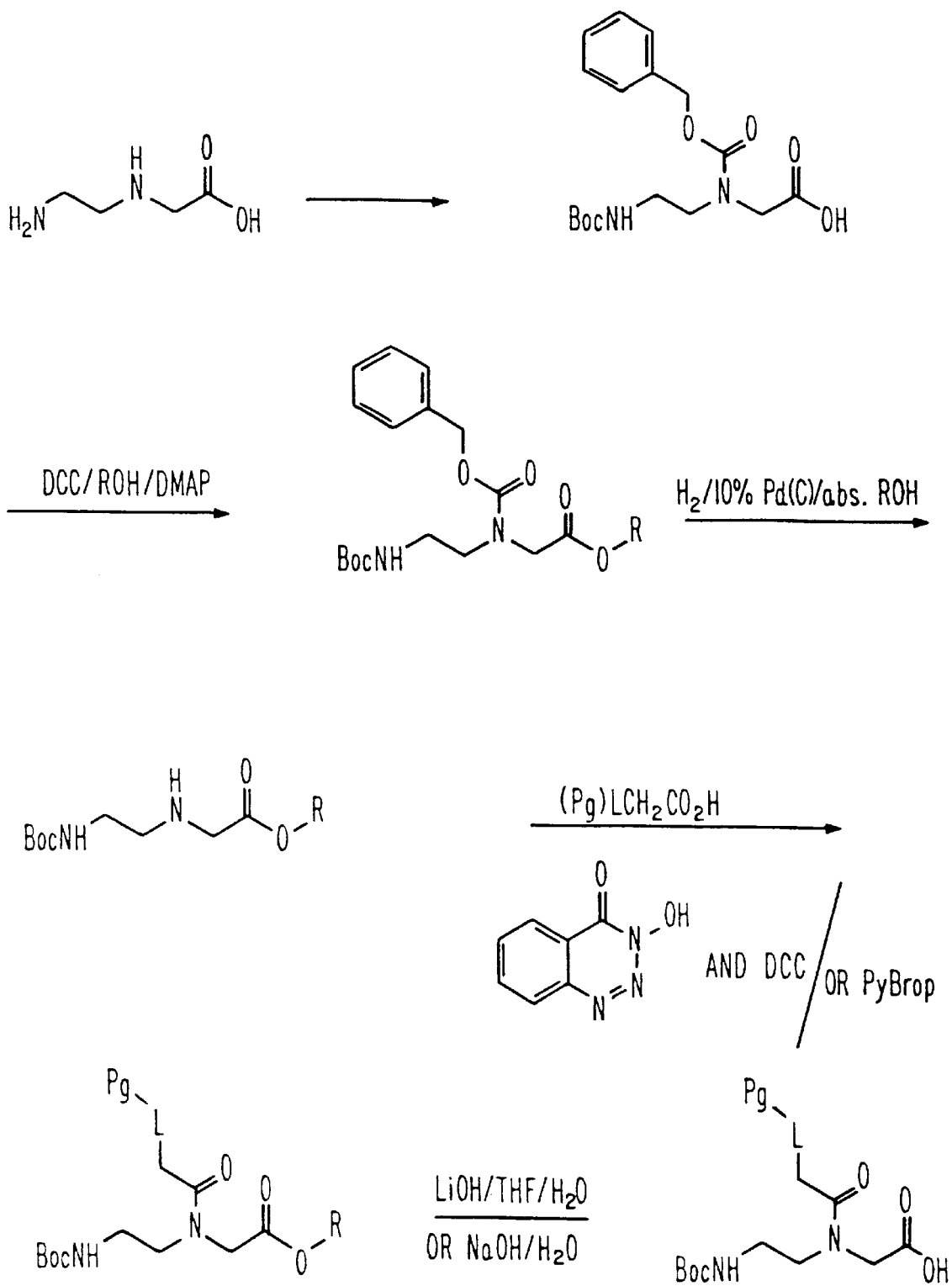
FIG. 13 provides a procedure for the synthesis of protected PNA synthons.

A portion of protected Boc-[Taeg]$_{10}$-Lys(ClZ)-BHA resin was treated as described in Example 17c to yield 1.7 mg of crude material upon HF cleavage of 7.0 mg dry H—[Taeg]$_{10}$-Lys(ClZ)-BHA resin. The main peak at 15.1 min (eluted at 17.0 min if injected from an aqueous solution instead of the 10% aqueous acetic acid solution) accounted for about 50% of the total absorbance. About 1.2 mg of the crude product was purified to give approximately 0.2 mg of >95% pure H—[Taeg]$_{10}$-Lys-NH$_2$. FIG. 13a. For (M+H)$^+$ the calculated m/z value was 2807.8 and the measured m/z value was 2808.2.

(f) Cleavage, Purification, and Identification of Acr[1]-[Taeg]$_{10}$-Lys-NH$_2$ 99.1 mg protected Acr[1]-[Taeg]$_{10}$-Lys(ClZ)-BHA resin (dry weight) was cleaved as described in Example 17c to yield 42.2 mg of crude material. The main peak at 25.3 min (eluted at 23.5 min if injected from an aqueous solution instead of the 10% aqueous acetic acid solution) accounted for about 45% of the total absorbance. An 8.87 mg portion of the crude product was purified to give approximately 5.3 mg of >97% pure H—[Taeg]$_{10}$-Lys-NH$_2$. For (M+H)$^+$ the calculated m/z value was 2850.8 and the measured m/z value was 2849.8.

(g) Cleavage and Purification of Acr[1]-[Taeg]$_{15}$-Lys-NH$_2$

A 78.7 mg portion of protected Acr[1]-[Taeg]$_{15}$-Lys(ClZ)-BHA resin (dry weight) was cleaved as described in Example I section (c) to yield 34.8 mg of crude material. The main peak at 23.5 min (about the same elution time if injected from an aqueous solution instead of the 10% aqueous acetic acid solution) and a "dimer" at 28.2 min accounted for about 35% of the total absorbance. About 4.5 mg of the crude product was purified to give approximately 1.6 mg of presumably >95% pure H—[Taeg]$_{10}$-Lys-NH$_2$. This compound could not be free of the "dimer" peak, which grew upon standing in aqueous acetic acid solution.

(h) Synthetic Protocol 2

(1) Boc-deprotection with TFA/CH$_2$Cl$_2$ (1:1, v/v), 3 ml, 3×1 min and 1×30 min; (2) washing with CH$_2$Cl$_2$, 3 ml, 6×1 min; (3) neutralization with DIEA/CH$_2$Cl$_2$ (1:19, v/v), 3 ml, 3×2 min; (4) washing with CH$_2$Cl$_2$, 3 ml, 6×1 min, and drain for 1 min; (5) 2–5 mg sample of PNA-resin can be taken out and dried thoroughly for a qualitative ninhydrin analysis; (6) for cycles 1 to 5 and cycles 10 to 15 the coupling reaction was carried out by addition of 3.2 equiv. (0.18 mmol; 100 mg) BocTaeg-OPfp dissolved in 1 ml CH$_2$Cl$_2$ followed by addition of 0.5 ml DMF (final concentration of pentafluorophenylester ~0.12 M); the coupling reaction was allowed to proceed for a total of 12–24 h with shaking; cycles 5 to 10 employed an additional 0.12 M DCC coupling of 0.12 M BocTaeg-OH in 1.5 ml DMF/CH$_2$Cl$_2$ (1:2, v/v); (7) washing with DMF, 3 ml, 1×2 min; (8) washing with CH$_2$Cl$_2$, 3 ml, 4×1 min; (9) neutralization with DIEA/CH$_2$Cl$_2$ (1:19, v/v), 3 ml, 2×2 min; (10) washing with CH$_2$Cl$_2$, 3 ml, 6×1 min; (11) 2–5 mg sample of protected PNA-resin is taken out for a qualitative ninhydrin test (after cycles 7, 10, and 15 unreacted amino groups were blocked by acetylation with N-acetylimidazol in methylene chloride).

EXAMPLE 19

Improved Solid-Phase Synthesis of H—[Taeg]$_{10}$-Lys-NH$_2$

The protected PNA was assembled onto an MBHA resin, using approximately half the loading of the BHA resin used in the previous examples. Furthermore, all cycles except one was followed by acetylation of uncoupled amino groups. The following describes the synthesis in full detail:

(a) Preparation of Boc-Lys(ClZ)—NH—CH(p—CH$_3$—C$_6$H$_4$)—C$_6$H$_4$ Resin (MBHA Resin) with an Initial Substitution of 0.3 mmol/g The desired substitution of Boc-Lys(ClZ)-MBHA resin was 0.25–0.30 mmol/g. In order to get this value, 1.5 mmol of Boc-Lys(ClZ) was coupled to 5.0 g of neutralized and preswollen MBHA resin (determined by the quantitative ninhydrin reaction to contain 0.64 mmol NH$_2$/g) using a single "in situ" coupling (1.5 mmol of DCC) in 60 ml of CH$_2$Cl$_2$. The reaction was carried out by shaking for 3 h in a manually operated, 225 ml, standard, solid-phase reaction vessel. Unreacted amino groups were then blocked by acetylation with a mixture of acetic anhydride/pyridine/CH$_2$Cl$_2$ (1:1:2, v/v/v) for 18 h. A quantitative ninhydrin reaction on the neutralized resin showed that only 0.00093 mmol/g free amine remained (see Table I), i.e. 0.15% of the original amino groups. The degree of substitution was estimated by deprotection and ninhydrin analysis, and was found to be 0.32 mmol/g for the neutralized H-Lys(ClZ)-MBHA resin. This compares well with the maximum value of 0.28 mmol/g for a quantitative coupling of 0.30 mmol Boc-Lys(ClZ)/g resin (see Table II).

(b) Stepwise Assembly of Boc-[Taeg]$_3$-Lys(ClZ)-MBHA Resin

The entire batch of H-Lys(ClZ)-MBHA resin prepared in section (a) was used directly (in the same reaction vessel) to assemble Boc-[Taeg]$_3$-Lys(ClZ)-MBHA resin by single couplings ("Synthetic Protocol 3") utilizing 2.5 equivalents of BocTaeg-OPfp in neat CH$_2$Cl$_2$. The quantitative ninhydrin reaction was applied throughout the synthesis (see Table II).

(c) Stepwise Assembly of Boc-[Taeg]$_8$-Lys(ClZ)-MBHA Resin

About 4.5 g of wet Boc-[Taeg]$_3$-Lys(ClZ)-MBHA resin (~0.36 mmol growing chains; taken out of totally ~19 g wet resin prepared in section (b)) was placed in a 55 ml SPPS reaction vessel. Boc-[Taeg]$_8$-Lys(ClZ)-MBHA resin was assembled by single couplings ("Synthetic Protocol 4") utilizing 2.5 equivalents of BocTaeg-OPfp in about 30% DMF/CH$_2$Cl$_2$. The progress of the synthesis was monitored at all stages by the quantitative ninhydrin reaction (see Table II).

(d) Stepwise Assembly of Boc-[Taeg]$_{10}$-Lys(ClZ)-MBHA Resin

About 1 g of wet Boc-[Taeg]$_8$-Lys(ClZ)-MBHA resin (~0.09 mmol growing chains; taken out of totally ~4 g wet resin prepared in section (c)) was placed in a 20 ml SPPS reaction vessel. Boc-[Taeg]$_{10}$-Lys(ClZ)-MBHA resin was assembled by the single-coupling protocol employed in the preceding section utilizing 2.5 equivalents of BocTaeg-OPfp in about 30% DMF/CH$_2$Cl$_2$. The reaction volume was 3 ml (vigorous shaking). The synthesis was monitored by the quantitative ninhydrin reaction (see Table II).

| Synthetic Step | Residue Coupled | Substitution After Deprotection (mmol/g) | | Remaining Free Amino Groups After ($\mu$mol/g) | | Estimated Extent of Coupling (%) |
|---|---|---|---|---|---|---|
| | | Measd | Theoret | Single Coupling | Acetylation | |
| "0" | BocLys(ClZ) | 0.32 | 0.28 | | 0.93 | |
| 1 | BocTaeg | 0.23 | 0.26 | 0.97 | 0.54 | >99.9 |
| 2 | BocTaeg | 0.21 | 0.24 | 0.92 | 0.46 | 99.8 |
| 3 | BocTaeg | 0.19 | 0.23 | 1.00 | 0.57 | 99.7 |
| 4 | BocTaeg | 0.18 | 0.21 | 1.85 | | 99.3 |
| 5 | BocTaeg | 0.17 | 0.20 | 2.01 | 0.19 | 99.9 |
| 6 | BocTaeg | 0.15 | 0.19 | 1.69 | 0.10 | 99.0 |
| 7 | BocaTeg | 0.11 | 0.18 | 1.11 | 0.66 | 99.1 |
| 8 | BocTaeg | 0.12 | 0.17 | 1.82 | 0.44 | 99.0 |
| 9 | BocTaeg | 0.10 | 0.17 | 5.63 | 0.56 | 94.8 |
| 10 | BocTaeg | 0.11 | 0.16 | 1.54 | 0.67 | 99.1 |

(e) Synthesis of Ac—[Taeg]$_{10}$-Lys(ClZ)-MBHA Resin

Following deprotection of a portion of Boc-[Taeg]$_{10}$-Lys(ClZ)-MBHA resin (estimated dry weight is about 45 mg), the resin was next acetylated quantitatively with a 2 ml mixture of acetic anhydride/pyridine/CH$_2$Cl$_2$ (1:1:2, v/v/v) for 2 h in a 3 ml solid-phase reaction vessel.

(f) Cleavage, Purification, and Identification of H—[Taeg]$_{10}$-Lys-NH$_2$

A portion of protected Boc-[Taeg]$_{10}$-Lys(ClZ)-BHA resin was treated as described in Example 17c to yield about 24 mg of crude material upon HF cleavage of 76 mg dry H—[Taeg]$_5$-Lys(ClZ)-BHA resin. The main peak at 15.2 min (which includes impurities such as deletion peptides and various byproducts) accounted for about 78% of the total absorbance. The main peak also accounted for about 88% of the "main peak plus deletion peaks" absorbance, which is in good agreement with the overall estimated coupling yield of 90.1% obtained by summarizing the individual coupling yields in Table II. A 7.2 mg portion of the crude product was purified from two batches by use of a semi-preparative reverse-phase column, (collecting the main peak in a beaker cooled with dry ice/2-propanol). Each contained 3.6 mg in 1 ml of H$_2$O. The frozen solution was lyophilized directly (without prior removal of acetonitrile on a speed vac) to give 4.2 mg of 82% pure H—[Taeg]$_{10}$-Lys-NH$_2$.

(g) Cleavage, Purification, and Identification of Ac—[Taeg]$_{10}$-Lys-NH$_2$

A 400.0 mg portion of protected Ac—[Taeg]$_{10}$-Lys(ClZ)-BHA resin (dry weight) was cleaved as described in Example 17c, except for the TFA treatment to yield 11.9 mg of crude material. The main peak at 15.8 min accounted for about 75% of the total absorbance. A 4.8 mg portion of the crude product was purified to give approximately 3.5 mg of >95% pure Ac—[Taeg]$_{10}$-Lys-NH$_2$. For (M+H)$^+$ the calculated m/z value=2849.8 and the measured m/z value=2848.8.

(h) Synthetic Protocol 3.

(1) Boc-deprotection with TFA/CH$_2$Cl$_2$ (1:1, v/v), 100 ml, 3×1 min and 1×30 min; (2) washing with CH$_2$Cl$_2$, 100 ml, 6×1 min; (3) neutralization with DIEA/CH$_2$Cl$_2$ (1:19, v/v), 100 ml, 3×2 min; (4) washing with CH$_2$Cl$_2$, 100 ml, 6×1 min, and drain for 1 min; (5) 2–5 mg sample of PNA-resin is taken out and dried thoroughly for a quantitative ninhydrin analysis to determine the substitution; (6) addition of 2.5 equiv. (3.75 mmol; 2.064 g) BocTaeg-OPfp dissolved in 35 ml CH$_2$Cl$_2$ (final concentration of pentafluorophenylester ~0.1 M); the coupling reaction was allowed to proceed for a total of 20–24 h with shaking; (7) washing with DMF, 100 ml, 1×2 min (to remove precipitate of BocTaeg-OH); (8) washing with CH$_2$Cl$_2$, 100 ml, 4×1 min; (9) neutralization with DIEA/CH$_2$Cl$_2$ (1:19, v/v), 100 ml, 2×2 min; (10) washing with CH$_2$Cl$_2$, 100 ml, 6×1 min; (11) 2–5 mg sample of protected PNA-resin is taken out for a rapid qualitative ninhydrin test and a further 2–5 mg is dried thoroughly for a quantitative ninhydrin analysis to determine the extent of coupling; (12) blocking of unreacted amino groups by acetylation with a 100 ml mixture of acetic anhydride/pyridine/CH$_2$Cl$_2$ (1:1:2, v/v/v) for 2 h; (13) washing with CH$_2$Cl$_2$, 100 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses. ps (i) Synthetic Protocol 4.

(1) Boc-deprotection with TFA/CH$_2$Cl$_2$ (1:1, v/v), 25 ml, 3×1 min and 1×30 min; (2) washing with CH$_2$Cl$_2$, 25 ml, 6×1 min; (3) neutralization with DIEA/CH$_2$Cl$_2$ (1:19, v/v), 25 ml, 3×2 min; (4) washing with CH$_2$Cl$_2$, 25 ml, 6×1 min, and drain for 1 min; (5) 2–5 mg sample of PNA-resin is taken out and dried thoroughly for a quantitative ninhydrin analysis to determine the substitution; (6) addition of 2.5 equiv. (0.92 mmol; 0.506 g) BocTaeg-OPfp dissolved in 6 ml CH$_2$Cl$_2$ followed by addition of 3 ml DMF (final concentration of pentafluorophenylester ~0.1 M); the coupling reaction was allowed to proceed for a total of 20–24 hrs with shaking; (7) washing with DMF, 25 ml, 1×2 min; (8) washing with CH$_2$Cl$_2$, 25 ml, 4×1 min; (9) neutralization with DIEA/CH$_2$Cl$_2$ (1:19, v/v), 25 ml, 2×2 min; (10) washing with CH$_2$Cl$_2$, 25 ml, 6×1 min; (11) 2–5 mg sample of protected PNA-resin is taken out for a rapid qualitative ninhydrin test and a further 2–5 mg is dried thoroughly for a quantitative ninhydrin analysis to determine the extent of coupling; (12) blocking of unreacted amino groups by acetylation with a 25 ml mixture of acetic anhydride/pyridine/CH$_2$Cl$_2$ (1:1:2, v/v/v) for 2 h (except after the first cycle); (13) washing with CH$_2$Cl$_2$, 25 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

EXAMPLE 20

Solid-Phase Synthesis of H—[Taeg]$_5$-Caeg-[Taeg]$_4$-Lys-NH$_2$ (a) Stepwise Assembly of Boc-[Taeg]$_5$-Caeg-[Taeg]$_4$-Lys (ClZ)-MBHA Resin About 2.5 g of wet Boc-[Taeg]$_3$-Lys(ClZ)-MBHA resin (~⅙ of the total remaining about 16 g wet resin; ~0.75 g dry resin ~0.15 mmol growing chains) was placed in a 6 ml SPPS reaction vessel. Boc-[Taeg]$_5$-Caeg-[Taeg]$_4$-Lys(ClZ)-MBHA resin was assembled by double coupling of all Taeg-residues utilizing the usual 2.5 equivalents of BocTaeg-OPfp in 2.5 ml about 30% DMF/CH$_2$Cl$_2$, except that the first residue was single-coupled. Incorporation of the C(Z)aeg-residue was accomplished by coupling with 2.0 equivalents of BocC(Z)aeg-OPfp in TFE/CH$_2$Cl$_2$ (1:2, v/v). The progress of the synthesis was monitored at all stages by the quantitative ninhydrin reaction (see Table III).

| Synthetic Step | Residue Coupled | Substitution After Deprotection (mmol/g) | | Remaining Free Amino Groups After (μmol/g) | | Acetylation | Estimated Extent of Coupling |
|---|---|---|---|---|---|---|---|
| | | Measd. | Theoret. | 1st Coupl | 2nd Coupl | | |
| 3 | | 0.19 | 0.23 | 1.00 | | 0.57 | |
| 4 | BocTaeg | 0.17 | 0.21 | 4.88 | | 97.3 | 97.3 |
| 5 | BocC(Z)aeg | 0.11 | 0.20 | 70.20 | 27.98 | 1.33 | 78.4 (46) |
| 6 | BocTaeg | 0.10 | 0.19 | 24.79 | 4.58 | 2.40 | 95.4 (75) |
| 7 | BocTaeg | 0.09 | 0.18 | 8.55 | 1.61 | 0.20 | >99.9 (93) |
| 8 | BocTaeg | 0.08 | 0.17 | 6.53 | 0.80 | 0.45 | 99.0 (91) |
| 9 | BocTaeg | 0.07 | 0.16 | 9.26 | 3.66 | 0.61 | 94.8 (86) |
| 10 | BocTaeg | 0.07 | 0.15 | 5.32 | 1.48 | 0.60 | 98.8 (93) |

(b) Cleavage, Purification, and Identification of H—[Taeg]$_5$-Caeg-[Taeg]$_4$-Lys-NH$_2$ A portion of protected Boc-[Taeg]$_{15}$-Caeg-[Taeg]$_4$-Lys(ClZ)-BHA resin was treated as described in Example I section (c) to yield about 14.4 mg of crude material upon HF cleavage of 66.9 mg dry H—[Taeg]$_5$-Caeg-[Taeg]$_4$-Lys(ClZ)-BHA resin. The main peak at 14.5 min accounted for >50% of the total absorbance. A 100.0 mg portion of the crude product was purified (8 batches; each dissolved in 1 ml H$_2$O) to give approximately 9.1 mg of 96% pure H—[Taeg]$_5$-Caeg-[Taeg]$_4$-Lys-NH$_2$ (FIG. 13b). For (M+H)$^+$ the calculated m/z value=2793.8 and the measured m/z value=2790.6.

EXAMPLE 21

N-Benzyloxycarbonyl-N'-(bocaminoethyl)glycine

Aminoethyl glycine (52.86 g; 0.447 mol) was dissolved in water (900 ml) and dioxane (900 ml) was added. The pH was adjusted to 11.2 with 2N NaOH. While the pH was kept at 11.2, tert-butyl-p-nitrophenyl carbonate (128.4 g; 0.537 mol) was dissolved in dioxane (720 ml) and added dropwise over the course of 2 hours. The pH was kept at 11.2 for at least three more hours and then left with stirring overnight. The yellow solution was cooled to 0° C. and the pH was adjusted to 3.5 with 2 N HCl. The mixture was washed with chloroform (4×100 ml), and the pH of the aqueous phase was readjusted to 9.5 with 2 N NaOH at 0° C. Benzyloxycarbonyl chloride (73.5 ml; 0.515 mol) was added over half an hour, while the pH was kept at 9.5 with 2 N NaOH. The pH was adjusted frequently over the next 4 hours, and the solution was left with stirring overnight. On the following day the solution was washed with ether (3×600 ml) and the pH of the solution was afterwards adjusted to 1.5 with 2 N HCl at 0° C. The title compound was isolated by extraction with ethyl acetate (5×1000 ml). The ethyl acetate solution was dried over magnesium sulfate and evaporated to dryness, in vacuo. This afforded 138 g, which was dissolved in ether (300 ml) and precipitated by the addition of petroleum ether (1800 ml). Yield 124.7 g (79%). M.p. 64.5–85° C. Anal. for $C_{17}H_{24}N_2O_6$ found(calc.) C: 58.40(57.94); H: 7.02(6.86); N: 7.94(7.95). $^1$H-NMR (250 MHz, $CDCl_3$) 7.33 & 7.32 (5H, Ph); 5.15 & 5.12 (2H, PhC$\underline{H}_2$); 4.03 & 4.01 (2H, NC$\underline{H}_2CO_2$H); 3.46 (b, 2H, BocNHC$H_2$C$\underline{H}_2$); 3.28 (b, 2H, BocNHC$\underline{H}_2$C$H_2$); 1.43 & 1.40 (9H, $^t$Bu). HPLC (260 nm) 20.71 min. (80.2%) and 21.57 min. (19.8%). The UV-spectra (200 nm–300 nm) are identical, indicating that the minor peak consists of Bis-Z-AEG.

EXAMPLE 22

N'-Boc-aminoethyl glycine ethyl ester

N-Benzyloxycarbonyl-N'-(bocaminoethyl)glycine (60.0 g; 0.170 mol) and N,N-dimethyl-4-aminopyridine (6.00 g) were dissolved in absolute ethanol (500 ml), and cooled to 0° C. before the addition of DCC (42.2 g; 0.204 mol). The ice bath was removed after 5 minutes and stirring was continued for 2 more hours. The precipitated DCU (32.5 g dried) was removed by filtration and washed with ether (3×100 ml). The combined filtrate was washed successively with diluted potassium hydrogen sulfate (2×400 ml), diluted sodium hydrogencarbonate (2×400 ml) and saturated sodium chloride (1×400 ml). The organic phase was filtered, then dried over magnesium sulfate, and evaporated to dryness, in vacuo, which yielded 66.1 g of an oily substance which contained some DCU.

The oil was dissolved in absolute ethanol (600 ml) and was added 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel (600 g $SiO_2$) chromatography. After elution with 300 ml 20% petroleum ether in methylene chloride, the title compound was eluted with 1700 ml of 5% methanol in methylene chloride. The solvent was removed from the fractions with satisfactory purity, in vacuo and the yield was 8.49 g. Alternatively 10 g of the crude material was purified by Kugel Rohr distillation. $^1$H-NMR (250 MHz, $CD_3OD$); 4.77 (b. s, NH); 4.18 (q, 2H, MeC$\underline{H}_2$—); 3.38 (s, 2H, NC$\underline{H}_2CO_2$Et); 3.16 (t, 2H, BocNHC$\underline{H}_2CH_2$); 2.68 (t, 2H, BocNHC$H_2$C$\underline{H}_2$); 1.43 (s, 9H, $^t$Bu) and 1.26 (t, 3H, $CH_3$) $^{13}$C-NMR 171.4 ($\underline{C}$OEt); 156.6 (CO); 78.3 (($CH_3)_3\underline{C}$); 59.9 ($CH_2$); 49.0 ($CH_2$); 48.1 ($CH_2$); 39.0 ($CH_2$); 26.9 ($CH_2$) and 12.6 ($CH_3$).

EXAMPLE 23

N'-Boc-aminoethyl glycine methyl ester

The above procedure was used, with methanol being substituted for ethanol. The final product was purified by column purification.

EXAMPLE 24

1-(Boc-aeg)thymine ethyl ester

N'-Boc-aminoethyl glycine ethyl ester (13.5 g; 54.8 mmol), DhbtOH (9.84 g; 60.3 mmol) and 1-carboxymethyl thymine (11.1 g; 60.3 mmol) were dissolved in DMF (210 ml). Methylene chloride (210 ml) then was added. The solution was cooled to 0° C. in an ethanol/ice bath and DCC (13.6 g; 65.8 mmol) was added. The ice bath was removed after 1 hour and stirring was continued for another 2 hours at ambient temperature. The precipitated DCU was removed by filtration and washed twice with methylene chloride (2×75 ml). To the combined filtrate was added more methylene chloride (650 ml). The solution was washed successively with diluted sodium hydrogen carbonate (3×500 ml), diluted potassium hydrogen sulfate (2×500 ml), and saturated sodium chloride (1×500 ml). Some precipitate was removed from the organic phase by filtration, The organic phase was dried over magnesium sulfate and evaporated to dryness, in vacuo. The oily residue was dissolved in methylene chloride (150 ml), filtered, and the title compound was precipitated by the addition of petroleum ether (350 ml) at 0° C. The methylene chloride/petroleum ether procedure was repeated once. This afforded 16.0 g (71%) of a material which was more than 99% pure by HPLC.

EXAMPLE 25

1-(Boc-aeg)thymine

The material from above was suspended in THF (194 ml, gives a 0.2 M solution), and 1 M aqueous lithium hydroxide (116 ml) was added. The mixture was stirred for 45 minutes at ambient temperature and then filtered to remove residual DCU. Water (40 ml) was added to the solution which was then washed with methylene chloride (300 ml). Additional water (30 ml) was added, and the alkaline solution was washed once more with methylene chloride (150 ml). The aqueous solution was cooled to 0° C. and the pH was adjusted to 2 by the dropwise addition of 1 N HCl (approx. 110 ml). The title compound was extracted with ethyl acetate (9×200 ml), the combined extracts were dried over magnesium sulfate and were evaporated to dryness, in vacuo. The residue was evaporated once from methanol, which after drying overnight afforded a colourless glassy solid. Yield 9.57 g (64%). HPLC >98% $R_T$=14.8 min.

Anal. for $C_{16}H_{24}N_4O_7$o0.25 $H_2O$ Found (calc.) C: 49.29 (49.42); H: 6.52(6.35); N: 14.11(14.41). Due to the limited rotation around the secondary amide, several of the signals were doubled in the ratio 2:1 (indicated in the list by mj. for major and mi. for minor). $^1$H-NMR (250 MHz, DMSO-$d_6$): 12.75 (b.s., 1H, $CO_2$H); 11.28 (s, "1H", mj., imide NH);

11.26 (s, "1H", mi., imide NH); 7.30 (s, "1H", mj., T H-6); 7.26 (s, "1H", mi., T H-6); 6.92 (b.t., "1", mj., BocNH); 6.73 (b.t., "1", mi., BocNH); 4.64 (s, "2H", mj., C$\underline{H}_2$CON); 4.46 (s, "2H", mj., C$\underline{H}_2$CON); 4.19 (s, "2H", mi., C$\underline{H}_2$CO$_2$H); 3.97 (s, "2H", mj., C$\underline{H}_2$CO$_2$H); 3.63–3.01 (unresolved m, includes water, C$\underline{H}_2$C$\underline{H}_2$); 1.75 (s, 3H, C$\underline{H}_3$) and 1.38 (s, 9H, $^t$Bu).

EXAMPLE 26

N$^4$-Benzyloxycarbonyl-1-(Boc-aeg)cytosine

N'-Boc-aminoethyl glycine ethyl ester (5.00 g; 20.3 mmol), DhbtOH (3.64 g; 22.3 mmol) and N$^4$-benzyloxycarbonyl-1-carboxymethyl cytosine (6.77 g; 22.3 mmol) were suspended in DMF (100 ml). Methylene chloride (100 ml) then was added. The solution was cooled to 0° C. and DCC (5.03 g; 24.4 mmol) was added. The ice bath was removed after 2 h and stirring was continued for another hour at ambient temperature. The reaction mixture then was evaporated to dryness, in vacuo. The residue was suspended in ether (100 ml) and stirred vigorously for 30 min. The solid material was isolated by filtration and the ether wash procedure was repeated twice. The material was then stirred vigorously for 15 min with dilute sodium hydrogencarbonate (approx. 4% solution, 100 ml), filtered and washed with water. This procedure was then repeated once, which after drying left 17.0 g of yellowish solid material. The solid was then boiled with dioxane (200 ml) and filtered while hot. After cooling, water (200 ml) was added. The precipitated material was isolated by filtration, washed with water, and dried. According to HPLC (observing at 260 nm) this material has a purity higher than 99%, besides the DCU. The ester was then suspended in THF (100 ml), cooled to 0° C., and 1 N LiOH (61 ml) was added. After stirring for 15 minutes, the mixture was filtered and the filtrate was washed with methylene chloride (2×150 ml). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 ml) and petroleum ether (300 ml) was added. Filtration and wash afforded 7.1 g (69%) after drying. HPLC showed a purity of 99% R$_T$=19.5 min, and a minor impurity at 12.6 min (approx. 1%) most likely the Z-de protected monomer. Anal. for C$_{23}$H$_{29}$N$_5$O$_8$ found(calc.) C: 54.16(54.87); H: 5.76(5.81) and N: 13.65(13.91). $^1$H-NMR (250 MHz, DMSO-d$_6$). 10.78 (b.s, 1H, CO$_2\underline{H}$); 7.88 (2 overlapping dublets, 1H, Cyt H-5); 7.41–7.32 (m, 5H, Ph); 7.01 (2 overlapping doublets, 1H, Cyt H-6); 6.94 & 6.78 (unres. triplets, 1H, BocN$\underline{H}$); 5.19 (S, 2H, PhC$\underline{H}_2$); 4.81 & 4.62 (s, 2H, C$\underline{H}_2$CON); 4.17 & 3.98 (s, 2H, C$\underline{H}_2$CO$_2$H); 3.42–3.03 (m, includes water, C$\underline{H}_2$C$\underline{H}_2$) and 1.38 & 1.37 (s, 9H, $^t$Bu). $^{13}$C-NMR. 150.88; 128.52; 128.18; 127.96; 93.90; 66.53; 49.58 and 28.22. IR: Frequency in cm$^{31\ 1}$ (intensity). 3423 (26.4), 3035 (53.2), 2978(41.4), 1736(17.3), 1658(3.8), 1563(23.0), 1501(6.8) and 1456 (26.4).

EXAMPLE 27

9-Carboxymethyl adenine ethyl ester

Adenine (10.0 g, 74 mmol) and potassium carbonate (10.29 g, 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether. Yield 3.4 g (20%). M.p. 215.5–220° C. Anal. for C$_9$H$_{11}$N$_5$O$_2$ found(calc.): C: 48.86 (48.65); H: 5.01(4.91); N: 31.66(31.42). $^1$H-NMR (250 MHz; DMSO-d$_6$): (s, 2H, H-2 & H-8), 7.25 (b. s., 2H, NH$_2$), 5.06 (s, 2H, NCH$_2$), 4.17 (q, 2H, J=7.11 Hz, OCH$_2$) and 1.21 (t, 3H, J=7.13 Hz, NCH$_2$). $^{13}$C-NMR. 152.70, 141.30, 61.41, 43.97 and 14.07. FAB-MS. 222 (MH+). IR: Frequency in cm$^{-1}$ (intensity). 3855 (54.3), 3274(10.4), 3246(14.0), 3117 (5.3), 2989(22.3), 2940(33.9), 2876(43.4), 2753(49.0), 2346 (56.1), 2106(57.1), 1899(55.7), 1762(14.2), 1742(14.2), 1742(1.0), 1671(1.8), 1644(10.9), 1606(0.6), 1582(7.1), 1522(43.8), 1477(7.2), 1445(35.8) and 1422(8.6). The position of alkylation was verified by X-ray crystallography on crystals, which were obtained by recrystallization from 96% ethanol.

EXAMPLE 28

N$^6$-Benzyloxycarbonyl-9-carboxymethyl adenine ethyl ester

9-Carboxymethyladenine ethyl ester (3.40 g, 15.4 mmol) was dissolved in dry DMF (50 ml) by gentle heating, cooled to 20° C., and added to a solution of N-ethyl-benzyloxycarbonylimidazole tetrafluoroborate (62 mmol) in ethylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleumeum ether (50 ml). This procedure was repeated once to give 3.45 g (63%) of the title compound. M.p. 132–35° C. Analysis for C$_{17}$H$_{17}$N$_5$O$_4$ found (calc.): C: 56.95(57.46); H: 4.71(4.82); N: 19.35(19.71). $^1$H-NMR (250 MHz; CDCl$_3$): 8.77 (s, 1H, H-2 or H-8); 7.99 (s, 1H, H-2 or H-8); 7.45–7.26 (m, 5H, Ph); 5.31 (s, 2H, N—C$\underline{H}_2$); 4.96 (s, 2H, Ph—C$\underline{H}_2$); 4.27 (q, 2H, J=7.15 Hz, C$\underline{H}_2$CH$_3$) and 1.30 (t, 3H, J=7.15 Hz, CH$_2$C$\underline{H}_3$). $^{13}$C-NMR: 153.09; 143.11; 128.66; 67.84; 62.51; 44.24 and 14.09. FAB-MS: 356 (MH+) and 312 (MH+—CO$_2$). IR: frequency in cm$^{31\ 1}$ (intensity). 3423 (52.1); 3182 (52.8); 3115(52.1); 3031(47.9); 2981(38.6); 1747(1.1); 1617(4.8); 15.87(8.4); 1552(25.2); 1511(45.2); 1492(37.9); 1465(14.0) and 1413(37.3).

EXAMPLE 29

N$^6$-Benzyloxycarbonyl-9-carboxymethyl adenine

N$^6$-Benzyloxycarbonyl-9-carboxymethyladenine ethyl ester (3.20 g; 9.01 mmol) was mixed with methanol (50 ml) cooled to 0° C. Sodium Hydroxide Solution (50 ml; 2N) was added, whereby the material quickly dissolved. After 30 min at 0° C., the alkaline solution was washed with methylene chloride (2×50ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for $C_{15}H_{13}N_5O_4$ found(calc.): C: 46.32(55.05); H: 4.24(4.00); N: 18.10 (21.40) and C/N: 2.57(2.56). $^1$H-NMR(250 MHz; DMSO-$d_6$): 8.70 (s, 2H, H-2 and H-8); 7.50–7.35 (m, 5H, Ph); 5.27 (s, 2H, N—C$\underline{H}_2$); and 5.15 (s, 2H, Ph—C$\underline{H}_2$). $^{13}$C-NMR. 168.77, 152.54, 151.36, 148.75, 145.13, 128.51, 128.17, 127.98, 66.76 and 44.67.IR (KBr) 3484(18.3); 3109(15.9); 3087(15.0); 2966(17.1); 2927(19.9); 2383(53.8); 1960 (62.7); 1739(2.5); 1688(5.2); 1655(0.9); 1594(11.7); 1560 (12.3); 1530(26.3); 1499(30.5); 1475(10.4); 1455(14.0); 1429(24.5) and 1411(23.6). FAB-MS: 328 (MH+) and 284 (MH+—$CO_2$). HPLC (215 nm, 260 nm) in system 1: 15.18 min, minor impurities all less than 2%.

EXAMPLE 30

$N^6$-Benzyloxycarbonyl-1-(Boc-aeg)adenine ethyl ester

N'-Boc-aminoethyl glycine ethyl ester (2.00 g; 8.12 mmol), DhbtOH (1.46 g; 8.93 mmol) and $N^6$-benzyloxycarbonyl-9-carboxymethyl adenine (2.92 g; 8.93 mmol) were dissolved in DMF (15 ml). Methylene chloride (15 ml) then was added. The solution was cooled to 0° C. in an ethanol/ice bath. DCC (2.01 g; 9.74 mmol) was added. The ice bath was removed after 2.5 h and stirring was continued for another 1.5 hour at ambient temperature. The precipitated DCU was removed by filtration and washed once with DMF (15 ml), and twice with methylene chloride (2×15 ml). To the combined filtrate was added more methylene chloride (100 ml). The solution was washed successively with dilute sodium hydrogen carbonate (2×100 ml), dilute potassium hydrogen sulfate (2×100 ml), and saturated sodium chloride (1×100 ml). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 ml) and activated carbon was added. After stirring for 5 minutes, the solution was filtered. The filtrate was mixed with water (30 ml) and was left with stirring overnight. The next day, the white precipitate was removed by filtration, washed with water, and dried, affording 1.16 g (26%) of a material with a purity higher than 98% by HPLC. Addition of water to the mother liquor afforded another 0.53 g with a purity of approx. 95%. Anal. for $C_{26}H_{33}N_7O_7 \cdot H_2O$ found(calc.) C: 55.01(54.44; H: 6.85 (6.15) and N: 16.47(17.09). $^1$H-NMR (250 MHz, CDCl$_3$) 8.74 (s, 1H, Ade H-2); 8.18 (b. s, 1H, ZNH); 8.10 & 8.04 (s, 1H, H-8); 7.46–7.34 (m, 5H, Ph); 5.63 (unres. t, 1H, BocNH); 5.30 (s, 2H, PhC$\underline{H}_2$); 5.16 & 5.00 (s, 2H, C$\underline{H}_2$CON); 4.29 & 4.06 (s, 2H, C$\underline{H}_2$CO$_2$H); 4.20 (q, 2H, OC$\underline{H}_2$CH$_3$); 3.67–3.29 (m, 4H, C$\underline{H}_2$C$\underline{H}_2$); 1.42 (s, 9H, $^t$Bu) and 1.27 (t, 3H, OCH$_2$C$\underline{H}_3$). The spectrum shows traces of ethanol and DCU.

EXAMPLE 31

$N^6$-Benzyloxycarbonyl-1-(Boc-aeg)adenine $N^6$-Benzyloxycarbonyl-1-(Boc-aeg)adenine ethyl ester (1.48 g; 2.66 mmol) was suspended in THF (13 ml) and the mixture was cooled to 0° C. Lithium hydroxide (8 ml; 1 N) was added. After 15 min of stirring, the reaction mixture was filtered, extra water (25 ml) was added, and the solution was washed with methylene chloride (2×25 ml). The pH of the aqueous solution was adjusted to pH 2.0 with 1 N HCl. The precipitate was isolated by filtration, washed with water, and dried, and dried affording 0.82 g (58%). The product repre- cipitated twice with methylene chloride/petroleum ether, 0.77 g (55%) after drying. M.p. 119° C. (decomp.) Anal. for $C_{24}H_{29}N_7O_7 \cdot H_2O$ found(calc.) C: 53.32(52.84); H: 5.71 (5.73); N: 17.68(17.97). FAB-MS. 528.5 (MH+). $^1$H-NMR (250 MHz, DMSO-$d_6$). 12.75 (very b, 1H, CO$_2$H); 10.65 (b. s, 1H, ZNH); 8.59 (d, 1H, J=2.14 Hz, Ade H-2); 8.31 (s, 1H, Ade H-8); 7.49–7.31 (m, 5H, Ph); 7.03 & 6.75 (unresol. t, 1H, BocNH); 5.33 & 5.16 (s, 2H, CH$_2$CON); 5.22 (s, 2H, PhC$\underline{H}_2$); 4.34–3.99 (s, 2H, CH$_2$CO$_2$H); 3.54–3.03 (m's, includes water, C$\underline{H}_2$C$\underline{H}_2$) and 1.39 & 1.37 (s, 9H, $^t$Bu). $^{13}$C-NMR. 170.4; 166.6; 152.3; 151.5; 149.5; 145.2; 128.5; 128.0; 127.9; 66.32; 47.63; 47.03; 43.87 and 28.24.

EXAMPLE 32

2-Amino-6-chloro-9-carboxymethylpurine

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h. under nitrogen. Water (150 ml) was added and the solution was filtered through Celite to give a clear yellow solution. The solution was acidified to a pH of 3 with 4 N hydrochloric acid. The precipitate was filtered and dried, in vacuo, over sicapent. Yield (3.02 g; 44.8%). $^1$H-NMR(DMSO-d6): d=4.88 ppm (s, 2H); 6.95 (s, 2H); 8.10 (s, 1H).

EXAMPLE 33

2-Amino-6-benzyloxy-9-carboxymethylpurine

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (4.05 g; 18.0 mmol) in DMF (85 ml) was slowly added, and the resulting suspension stirred overnight at 20° C. Sodium hydroxide solution (1N, 100 ml) was added and the clear solution was washed with ethyl acetate (3×100 ml). The water phase then was acidified to a pH of 3 with 4 N hydrochloric acid. The precipitate was taken up in ethyl acetate (200 ml), and the water phase was extracted with ethyl acetate (2×100 ml). The combined organic phases were washed with saturated sodium chloride solution (2×75 ml), dried with anhydrous sodium sulfate, and taken to dryness by evaporation, in vacuo. The residue was recrystallized from ethanol (300 ml). Yield after drying, in vacou, over sicapent: 2.76 g (52%). M.p. 159–65° C. Anal. (calc., found) C(56.18; 55.97), H(4.38; 4.32), N(23.4; 23.10). $^1$H-NMR (DMSO-d$_6$): 4.82 ppm.(s, 2H); 5.51 (s, 2H); 6.45 (s, 2H); 7.45 (m, 5H); 7.82 (s, 1H).

EXAMPLE 34

N-([2-Amino-6-benzyloxy-purine-9-yl]-acetyl)-N-(2-Boc-aminoethyl)-glycine [BocGaeg-OH monomer]

2-Amino-6-benzyloxy-9-carboxymethyl-purine (0.50 g; 1.67 mmol), methyl-N(2-[tert-butoxycarbonylamino]ethyl)-glycinate (0.65 g; 2.80 mmol), diisopropylethyl amine (0.54 g; 4.19 mmol), and bromo-tris-pyrrolidino-phosphonium-hexafluorophosphate (PyBroP®) (0.798 g; 1.71 mmol) were stirred in DMF (2 ml) for 4 h. The clear solution was poured into an ice-cooled solution of sodium hydrogen carbonate (1 N; 40 ml) and extracted with ethyl acetate (3 +40 ml). The organic layer was washed with potassium hydrogen sulfate solution (1 N; 2×40 ml), sodium hydrogen carbonate (1 N; 1×40 ml) and saturated sodium chloride solution (60 ml).

After drying with anhydrous sodium sulfate and evaporation, in vacuo, the solid residue was recrystallized from ethyl acetate/hexane (20 ml (2:1)) to give the methyl ester in 63% yield (MS-FAB 514 (M+1). Hydrolysis was accomplished by dissolving the ester in ethanol/water (30 ml (1:2)) containing conc. sodium hydroxide (1 ml). After stirring for 2 h, the solution was filtered and acidified to a pH of 3, by the addition of 4 N hydrochloric acid. The title compound was obtained by filtration. Yield: 370 mg (72% for the hydrolysis). Purity by HPLC was more than 99%. Due to the limited rotation around the secondary amide several of the signals were doubled in the ratio 2:1 (indicated in the list by mj. for major and mi. for minor). $^1$H-NMR(250, MHz, DMSO-$d_6$): d=1.4 ppm. (s, 9H); 3.2 (m, 2H); 3.6 (m, 2H); 4.1 (s, mj., CONRC$\underline{H}_2$COOH); 4.4 (s, mi., CONRC$\underline{H}_2$COOH); 5.0 (s, mi., Gua-C$\underline{H}_2$CO—); 5.2 (s, mj., Gua-C$\underline{H}_2$CO); 5.6 (s, 2H); 6.5 (s, 2H); 6.9 (m, mi., BocNH); 7.1 (m, mj., BocNH); 7.5 (m., 3H); 7.8 (s, 1H); 12,8 (s; 1H). $^{13}$C-NMR. 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 35

3-Boc-amino-1,2-propanediol

3-Amino-1,2-propanediol (40.00 g, 0.440 mol, 1.0 eq.) was dissolved in water (1000 ml) and cooled to 0° C. Di-tert-butyl dicarbonate (115.0 g, 0.526 mol, 1.2 eq.) was added in one portion. The reaction mixture was heated to room temperature on a water bath during stirring. The pH was maintained at 10.5 with a solution of sodium hydroxide (17.56 g, 0.440 mol, 1.0 eq.) in water (120 ml). When the addition of aqueous sodium hydroxide was completed, the reaction mixture was stirred overnight at room temperature. Subsequently, ethyl acetate (750 ml) was added to the reaction mixture, followed by cooling to 0° C. The pH was adjusted to 2.5 with 4 N sulphuric acid with vigorous stirring. The phases were separated and the water phase was washed with additional ethyl acetate (6×350 ml). The volume of the organic phase was reduced to 900 ml by evaporation under reduced pressure. The organic phase then was washed with a saturated aqueous solution of potassium hydrogen sulfate diluted to twice its volume (1×1000 ml) and with saturated aqueous sodium chloride 1×500 ml). The organic phase was dried (MgSO$_4$) and evaporated under reduced pressure to yield 50.12 g (60%) of the title compound. The product could be solidified by evaporation from methylene chloride and subsequent freezing. $^1$H-NMR (CDCl$_3$/TMS): d=1.43 (s, 9H, Me$_3$C), 3.25 (m, 2H, CH$_2$), 3.57 (m, 2H, CH$_2$), 3.73 (m, 1H, CH). $^{13}$C-NMR (CDCl$_3$/TMS): d=28.2 (Me$_3$C), 42.6 (CH$_2$), 63.5, 71.1 (CH$_2$OH, CHOH), 79.5 (Me$_3$C), 157.0 (C=O).

EXAMPLE 36

2-(Boc-amino)ethyl-L-alanine methyl ester

3-Boc-amino-1,2-propanediol (20.76 g, 0.109 mol, 1 eq.) was suspended in water (150 ml). Potassium m-periodate (24.97 g, 0.109 mol, 1 eq.) was added and the reaction mixture was stirred for 2 h at room temperature under nitrogen. The reaction mixture was filtered and the water phase extracted with chloroform (6×250 ml) The organic phase was dried (MgSO$_4$) and evaporated to afford an almost quantitative yield of Boc-aminoacetaldehyde as a colourless oil, which was used without further purification in the following procedure.

Palladium-on-carbon (10%, 0.8 g) was added to MeOH (250 ml) under nitrogen with cooling (0° C.) and vigorous stirring.

Anhydrous sodium acetate (4.49 g, 54.7 mmol, 2 eqv) and L-alanine methyl ester, hydrochloride (3.82 g, 27.4 mmol, 1 eqv) were added. Boc-aminoacetaldehyde (4.79 g, 30.1 mmol, 1.1 eqv) was dissolved in MeOH (150 ml) and added to the reaction mixture. The reaction mixture was hydrogenated at atmospheric pressure and room temperature until hydrogen uptake had ceased. The reaction mixture was filtered through celite, which was washed with additional MeOH. The MeOH was removed under reduced pressure. The residue was suspended in water (150 ml) and pH adjusted to 8.0 by dropwise addition of 0.5 N NaOH with vigorous stirring. The water phase was extracted with methylene chloride (4×250 ml). The organic phase was dried (MgSO$_4$), filtered through celite, and evaporated under reduced pressure to yield 6.36 g (94%) of the title compound as a clear, slightly yellow oil. MS (FAB-MS): m/z (%)=247 (100, M+1), 191 (90), 147 (18). $^1$H-NMR (250 MHz, CDCl$_3$). 1.18 (d, J=7.0 Hz, 3H, Me), 1.36 (s, 9H, Me$_3$C), 1.89 (b, 1H, NH), 2.51 (m, 1H, CH$_2$), 2.66 (m, 1H, CH$_2$), 3.10 (m, 2H, CH$_2$), 3.27 (q, J=7.0 Hz, 1H, CH), 3.64 (s, 3H, OMe), 5.06 (b, 1H, carbamate NH). $^{13}$C-NMR. d=18.8 (Me), 28.2 (Me$_3$C), 40.1, 47.0 (CH$_2$), 51.6 (OMe), 56.0 (CH), 155.8 (carbamate C=O), 175.8 (ester C=O).

EXAMPLE 37

N-(Boc-aminoethyl)-N-(1-thyminylacetyl)-L-alanine methyl ester

To a solution of Boc-aminoethyl-(L)-alanine methyl ester (1.23 g, 5.0 mmol) in DMF (10 ml) was added Dhbt-OH (0,90 g, 5.52 mmol) and 1-thyminylacetic acid (1.01 g, 5.48 mmol). When the 1-thyminylacetic acid was dissolved, dichloromethane (10 ml) was added and the solution was cooled on an ice bath. After the reaction mixture had reached 0° C., DCC (1.24 g, 6.01 mmol) was added. Within 5 min after the addition, a precipitate of DCU was seen. After a further 5 min, the ice bath was removed. Two hours later, TLC analysis showed the reaction to be finished. The mixture was filtered and the precipitate washed with dichloromethane (100 ml). The resulting solution was extracted twice with 5% sodium hydrogen carbonate (150 ml) and twice with saturated potassium hydrogen sulfate (25 ml) in water (100 ml). After a final extraction with saturated sodium chloride (150 ml), the solution was dried with magnesium sulfate and evaporated to give a white foam. The foam was purified by column chromatography on silica gel using dichloromethane with a methanol gradient as eluent. This yielded a pure compound (>99% by HPLC) (1.08 g, 52.4%). FAB-MS: 413 (M+1) and 431 (M+1+water). $^1$H-NMR (CDCl$_3$): 4.52 (s, 2H, CH'$_2$); 3,73 (s, 3H, OMe); 3.2–3.6 (m, 4H, ethyl CH$_2$'s); 1.90 (s, 3H, Me in T); 1.49 (d, 3H, Me in Ala, J=7.3 Hz); 1.44 (s, 9H, Boc).

EXAMPLE 38

N-(Boc-aminoethyl)-N-(1-thyminylacetyl)-L-alanine

The methyl ester of the title compound (2.07 g, 5.02 mmol) was dissolved in methanol (100 ml), and cooled on an ice bath. 2 M sodium hydroxide (100 ml) was added. After stirring for 10 min, the pH of the mixture was adjusted to 3 with 4 M hydrogen chloride. The solution was subsequently extracted with ethyl acetate (3×100 ml). The combined organic extracts were dried over magnesium sulfate.

After evaporation, the resulting foam was dissolved in ethyl acetate (400 ml) and a few ml of methanol to dissolve the solid material. Petroleum ether then was added until precipitation started. After standing overnight at −20° C., the precipitate was removed by filtration. This gave 1.01 g (50.5%) of pure compound (>99% by HPLC). The compound can be recrystallized from 2-propanol. FAB-MS: 399 (M+1). $^1$H-NMR (DMSO-d$_6$): 11.35 (s, 1H, COO); 7.42 (s, 1H, H'$_6$); 4.69 (s, 2H, CH'$_2$); 1.83 (s, 3H, Me in T); 1.50–1.40 (m, 12H, Me in Ala+Boc).

EXAMPLE 39

(a) N-(Boc-aminoethyl)-N-(1-thyminylacetyl)-D-alanine methyl ester

To a solution of Boc-aminoethyl alanine methyl ester (2.48 g, 10.1 mmol) in DMF (20 ml) was added Dhbt-OH (1.80 g, 11.0 mmol) and thyminylacetic acid (2.14 g, 11.6 mmol). After dissolution of the 1-thyminylacetic acid, methylene chloride (20 ml) was added and the solution cooled on an ice bath. When the reaction mixture had reached 0° C., DCC (2.88 g, 14.0 mmol) was added. Within 5 min after the addition a precipitate of DCU was seen. After 35 min the ice bath was removed. The reaction mixture was filtered 3.5 h later and the precipitate washed with methylene chloride (200 ml). The resulting solution was extracted twice with 5% sodium hydrogen carbonate (200 ml) and twice with saturated potassium hydrogen sulfate in water (100 ml). After a final extraction with saturated sodium chloride (250 ml), the solution was dried with magnesium sulfate and evaporated to give an oil. The oil was purified by short column silica gel chromatography using methylene chloride with a methanol gradient as eluent. This yielded a compound which was 96% pure according to HPLC (1.05 g, 25.3%) after precipitation with petroleum ether. FAB-MS: 413 (M+1). $^1$H-NMR (CDCl$_3$): 5.64 (t, 1H, BocNH, J=5.89 Hz); 4.56 (d, 2H, CH'$_2$); 4.35 (q, 1H, CH in Ala, J=7.25 Hz); 3.74 (s, 3H, OMe); 3.64–3.27 (m, 4H, ethyl H's); 1.90 (s, 3H, Me in T); 1.52–1.44 (t, 12H, Boc+Me in Ala).

(b) N-(Boc-aminoethyl)-N-(1-thyminylacetyl)-D-alanine

The methyl ester of the title compound (1.57 g, 3.81 mmol) was dissolved in methanol (100 ml) and cooled on an ice bath. Sodium hydroxide (100 ml; 2 M) was added. After stirring for 10 min the pH of the mixture was adjusted to 3 with 4 M hydrogen chloride. The solution then was extracted with ethyl acetate (3×100 ml). The combined organic extracts were dried over magnesium sulfate. After evaporation, the oil was dissolved in ethyl acetate (200 ml). Petroleum ether was added (to a total volume of 600 ml) until precipitation started. After standing overnight at −20° C., the precipitate was removed by filtration. This afforded 1.02 g (67.3%) of the title compound, which was 94% pure according to HPLC. FAB-MS: 399 (M+1). $^1$H-NMR: 11.34 (s, 1H, COOH); 7.42 (s, 1H, H'$_6$); 4.69 (s, 2H, CH'$_2$); 4.40 (q, 1H, CH in Ala, J=7.20 Hz); 1.83 (s, 3H, Me in T); 1.52–1.40 (m, 12H, Boc+Me in Ala).

EXAMPLE 40

N-(N'-Boc-3'-aminopropyl)-N-[(1-thyminyl)acetyl] glycine methyl ester

N-(N'-Boc-3'-aminopropyl)glycine methyl ester (2.84 g, 0.0115 mol) was dissolved in DMF (35 ml), followed by addition of DhbtOH (2.07 g, 0.0127 mol) and 1-thyminylacetic acid (2.34 g, 0.0127 mol). Methylene chloride (35 ml) was added and the mixture cooled to 0° C. on an ice bath. After addition of DCC (2.85 g, 0.0138 mol), the mixture was stirred at 0° C. for 2 h, followed by 1 h at room temperature. The precipitated DCU was removed by filtration, washed with methylene chloride (25 ml), and a further amount of methylene chloride (150 ml) was added to the filtrate. The organic phase was extracted with sodium hydrogen carbonate (1 volume saturated diluted with 1 volume water, 6×250 ml), potassium sulfate (1 volume saturated diluted with 4 volumes water, 3×250 ml), and saturated aqueous sodium chloride (1×250 ml), dried over magnesium sulfate, and evaporated to dryness, in vacuo. The solid residue was suspended in methylene chloride (35 ml) and stirred for 1 h. The precipitated DCU was removed by filtration and washed with methylene chloride (25 ml). The filtrate was evaporated to dryness, in vacuo, and the residue purified by column chromatography on silica gel, eluting with a mixture of methanol and methylene chloride (gradient from 3–7% methanol in methylene chloride). This afforded the title compound as a white solid (3.05 g, 64%). M.p. 76–79° C. (decomp.). Anal. for C$_{18}$H$_{28}$N$_4$O$_7$, found (calc.) C: 52.03 (52.42) H: 6.90 (6.84) N: 13.21 (13.58). The compound showed satisfactory $^1$H and $^{13}$C-NMR spectra.

EXAMPLE 41

N-(N'-Boc-3'-aminopropyl)-N-[(1-thyminyl)acetyl] glycine

N-(N'-Boc-3'-aminopropyl)-N-[(1-thyminyl)acetyl] glycine methyl ester (3.02 g, 0.00732 mol) was dissolved in methanol (25 ml) and stirred for 1.5 h with 2 M sodium hydroxide (25 ml). The methanol was removed by evaporation, in vacuo, and pH adjusted to 2 with 4 M hydrochloric acid at 0° C. The product was isolated as white crystals by filtration, washed with water (3×10 ml), and dried over sicapent, in vacuo. Yield 2.19 g (75%). Anal. for C$_{17}$H$_{26}$N$_4$O$_7$, H$_2$O, found (calc.) C: 49.95 (49.03) H: 6.47 (6.29) N: 13.43 (13.45). The compound showed satisfactory $^1$H and $^{13}$C-NMR spectra.

EXAMPLE 42

3-(1-Thyminyl)-propanoic acid methyl ester

Thymine (14.0 g, 0.11 mol) was suspended in methanol. Methyl acrylate (39.6 ml, 0.44 mol) was added, along with catalytic amounts of sodium hydroxide. The solution was refluxed in the dark for 45 h, evaporated to dryness, in vacuo, and the residue dissolved in methanol (8 ml) with heating. After cooling on an ice bath, the product was precipitated by addition of ether (20 ml), isolated by filtration, washed with ether (3×15 ml), and dried over sicapent, in vacuo. Yield 11.23 g (48%). M.p. 112–119° C. Anal. for C$_9$H$_{12}$N$_2$O$_4$, found (calc.) C: 51.14 (50.94) H: 5.78 (5.70) N: 11.52 (13.20). The compound showed satisfactory $^1$H and $^{13}$C-NMR spectra.

EXAMPLE 43

3-(1-Thyminyl)-propanoic acid 3-(1-Thyminyl)-propanoic acid methyl ester (1.0 g, 0.0047 mol) was suspended in 2 M sodium hydroxide (15 ml), boiled for 10 min. The pH was adjusted to 0.3 with conc. hydrochloric acid. The solution was extracted with ethyl acetate (10×25 ml). The organic phase was extracted with saturated aqueous sodium chloride, dried over magnesium sulfate, and evaporated to dryness, in vacuo, to give the title compound as a white solid (0.66 g, 71%). M.p. 118–121° C. Anal. for $C_8H_{10}N_2O_4$, found (calc.) C: 48.38 (48.49) H: 5.09 (5.09) N: 13.93 (14.14). The compound showed satisfactory $^1H$ and $^{13}C$-NMR spectra.

EXAMPLE 44

N-(N'-Boc-aminoethyl)-N-[(1-thyminyl)propanoyl] glycine ethyl ester

N-(N'-Boc-aminoethyl)glycine ethyl ester (1.0 g, 0.0041 mol) was dissolved in DMF (12 ml). DhbtOH (0.73 g, 0.0045 mol) and 3-(1-thyminyl)-propanoic acid (0.89 g, 0.0045 mol) were added. Methylene chloride (12 ml) then was added and the mixture was cooled to 0° C. on an ice bath. After addition of DCC (1.01 g, 0.0049 mol), the mixture was stirred at 0° C. for 2 h, followed by 1 h at room temperature. The precipitated DCU was removed by filtration, washed with methylene chloride (25 ml), and a further amount of methylene chloride (50 ml) was added to the filtrate. The organic phase was extracted with sodium hydrogen carbonate (1 volume saturated diluted with 1 volume water, 6×100 ml), potassium sulfate (1 volume saturated diluted with 4 volumes water, 3×100 ml), and saturated aqueous sodium chloride (1×100 ml), dried over magnesium sulfate, and evaporated to dryness, in vacuo. The solid residue was suspended in methylene chloride (15 ml), and stirred for 1 h. The precipitated DCU was removed by filtration and washed with methylene chloride. The filtrate was evaporated to dryness, in vacuo, and the residue purified by column chromatography on silica gel, eluting with a mixture of methanol and methylene chloride (gradient from 1 to 6% methanol in methylene chloride). This afforded the title compound as a white solid (1.02 g, 59%). Anal. for $C_{19}H_{30}N_4O_7$, found (calc.) C: 53.15 (53.51) H: 6.90 (7.09) N: 12.76 (13.13). The compound showed satisfactory 1H and $^{13}C$-NMR spectra.

EXAMPLE 45

N-(N'-Boc-aminoethyl)-N-[(1-thyminyl)propanoyl] glycine

N-(N'-Boc-aminoethyl)-N-[(1-thyminyl)propanoyl] glycine ethyl ester (0.83 g, 0.00195 mol) was dissolved in methanol (25 ml). Sodium hydroxide (25 ml; 2 M) was added. The solution was stirred for 1 h. The methanol was removed by evaporation, in vacuo, and the pH adjusted to 2 with 4 M hydrochloric acid at 0° C. The product was isolated by filtration, washed with ether (3×15 ml), and dried over sicapent, in vacuo. Yield 0.769 g, 99%). M.p. 213° C. (decomp.).

EXAMPLE 46

Mono-Boc-ethylenediamine (2)

tert-Butyl-4-nitrophenyl carbonate (1) (10.0 g; 0.0418 mol) dissolved in DMF (50 ml) was added dropwise over a period of 30 min to a solution of ethylenediamine (27.9 ml; 0.418 mol) and DMF (50 ml) and stirred overnight. The mixture was evaporated to dryness, in vacuo, and the resulting oil dissolved in water (250 ml). After cooling to 0° C., pH was adjusted to 3.5 with 4 M hydrochloric acid. The solution then was filtered and extracted with chloroform (3×250 ml). The pH was adjusted to 12 at 0° C. with 2 M sodium hydroxide, and the aqueous solution extracted with methylene chloride (3×300 ml). After treatment with sat. aqueous sodium chloride (250 ml), the methylene chloride solution was dried over magnesium sulfate. After filtration, the solution was evaporated to dryness, in vacuo, resulting in 4.22 g (63%) of the product (oil). $^1H$-NMR (90 MHz; $CDCl_3$): δ 1.44 (s, 9H); 2.87 (t, 2H); 3.1 (q, 2H); 5.62 (s, broad).

EXAMPLE 47

(N-Boc-aminoethyl)-β-alanine methyl ester, HCl

Mono-Boc-ethylenediamine (2) (16.28 g; 0.102 mol) was dissolved in acetonitrile (400 ml) and methyl acrylate (91.50 ml; 1.02 mol) was transferred to the mixture with acetonitrile (200 ml). The solution was refluxed overnight under nitrogen in the dark to avoid polymerization of methyl acrylate. After evaporation to dryness, in vacuo, a mixture of water and ether (200+200 ml) was added, and the solution was filtered and vigorously stirred. The aqueous phase was extracted one more time with ether and then freeze dried to yield a yellow solid. Recrystallization from ethyl acetate yielded 13.09 g (46%) of the title compound. M.p. 138–140° C. Anal. for $C_{11}H_{23}N_2O_4Cl$, found (calc.) C: 46.49 (46.72) H: 8.38 (8.20) N: 9.83 (9.91) Cl: 12.45 (12.54). $^1H$-NMR (90 MHz; DMSO-$d_6$): δ 1.39 (s, 9H); 2.9 (m, 8H); 3.64 (s, 3H).

EXAMPLE 48

N-[(1-Thyminyl)acetyl]-N'-Boc-aminoethyl-β-alanine methyl ester (N-Boc-amino-ethyl)-β-alanine methyl ester, HCl (3) (2.0 g; 0.0071 mol) and 1-thyminylacetic acid pentafluorophenyl ester (5) (2.828 g; 0.00812 mol) were dissolved in DMF (50 ml). Triethyl amine (1.12 ml; 0.00812 mol) was added and the mixture stirred overnight. After addition of methylene chloride (200 ml) the organic phase was extracted with aqueous sodium hydrogen carbonate (3×250 ml), half-sat. aqueous potassium hydrogen sulfate (3×250 ml), and sat. aqueous sodium chloride (250 ml) and dried over magnesium sulfate. Filtration and evaporation to dryness, in vacuo, resulted in 2.9 g (99%) yield (oil). $^1H$-NMR (250 MHz; $CDCl_3$): due to limited rotation around the secondary amide several of the signals were doubled; δ 1.43 (s, 9H); 1.88 (s, 3H); 2.63 (t, 1H); 2.74 (t, 1H); 3.25–3.55 (4×t, 8H); 3.65 (2×t, 2H); 3.66 (s, 1.5); 3.72 (s, 1.5); 4.61 (s, 1H); 4.72 (s, 2H); 5.59 (s, 0.5H); 5.96 (s, 0.5H); 7.11 (s, 1H); 10.33 (s, 1H).

EXAMPLE 49

N-[(1-Thyminyl)acetyl]-N'-Boc-aminoethyl-β-alanine

N-[(1-Thyminyl)acetyl]-N'-Boc-aminoethyl-β-alanine methyl ester (3.0 g; 0.0073 mol) was dissolved in 2 M sodium hydroxide (30 ml), the pH adjusted to 2 at 0° C. with 4 M hydrochloric acid, and the solution stirred for 2 h. The precipitate was isolated by filtration, washed three times with cold water, and dried over sicapent, in vacuo. Yield 2.23 g (77%). M.p. 170–176° C. Anal. for $C_{17}H_{26}N_4O_7$, $H_2O$, found (calc.) C: 49.49 (49.03) H: 6.31 (6.78) N: 13.84 (13.45). $^1H$-NMR (90 MHz; DMSO-$d_6$): δ 1.38 (s, 9H); 1.76 (s, 3H); 2.44 and 3.29 (m, 8H); 4.55 (s, 2H); 7.3 (s, 1H); 11.23 (s, 1H). FAB-MS: 399 (M+1).

EXAMPLE 50

N-[(1-($N^4$-Z)-cytosyl)acetyl]-N'-Boc-aminoethyl-β-alanine methyl ester (N-Boc-amino-ethyl)-β-alanine methyl ester, HCl (3) (2.0 g; 0.0071 mol) and 1-(N-4-Z)-cytosylacetic acid pentafluorophenyl ester (5) (3.319 g; 0.0071 mol) were dissolved in DMF (50 ml). Triethyl amine (0.99 ml; 0.0071 mol) was added and the mixture stirred overnight. After addition of methylene chloride (200 ml), the organic phase was extracted with aqueous sodium hydrogen carbonate (3×250 ml), half-sat. aqueous potassium hydrogen sulfate (3×250 ml), and sat. aqueous sodium chloride (250 ml), and dried over magnesium sulfate. Filtration and evaporation to dryness, in vacuo, resulted in 3.36 g of solid compound which was recrystallized from methanol. Yield 2.42 g (64%). M.p. 158–161° C. Anal. for $C_{25}H_{33}N_5O_8$, found (calc.) C: 55.19 (56.49) H: 6.19 (6.26) N: 12.86 (13.18). $^1$H-NMR (250 MHz; $CDCl_3$): due to limited rotation around the secondary amide several of the signals were doubled; δ 1.43 (s, 9H); 2.57 (t, 1H); 3.60–3.23 (m's, 6H); 3.60 (s, 1.5H); 3.66 (s, 1.5H); 4.80 (s, 1H); 4.88 (s, 1H); 5.20 (s, 2H); 7.80–7.25 (m's, 7H). FAB-MS: 532 (M+1).

EXAMPLE 51

N-[(1-($N^4$-Z)-cytosyl)acetyl]-N'-Boc-aminoethyl-β-alanine

N-[(1-(N-4-Z)-cytosyl)acetyl]-N'-Boc-aminoethyl-β-alanine methyl ester (0.621 g; 0.0012 mol) was dissolved in 2 M sodium hydroxide (8.5 ml) and stirred for 2h. Subsequently, pH was adjusted to 2 at 0° C. with 4 M hydrochloric acid and the solution stirred for 2 h. The precipitate was isolated by filtration, washed three times with cold water, and dried over sicapent, in vacuo. Yield 0.326 g (54%). The white solid was recrystallized from 2-propanol and washed with petroleum ether. Mp. 163° C. (decomp.). Anal. for $C_{24}H_{31}N_5O_8$, found (calc.) C: 49.49 (49.03) H: 6.31 (6.78) N: 13.84 (13.45). $^1$H-NMR (250 MHz; $CDCl_3$): due to limited rotation around the secondary amide several of the signals were doubled; δ 1.40 (s, 9H); 2.57 (t, 1H); 2.65 (t, 1H); 3.60–3.32 (m's, 6H); 4.85 (s, 1H); 4.98 (s, 1H); 5.21 (s, 2H); 5.71 (s, 1H, broad); 7.99–7.25 (m's, 7H). FAB-MS: 518 (M+1).

EXAMPLE 52

Example of a PNA-oligomer with a guanine residue (a) Solid-Phase Synthesis of H—[Taeg]$_5$-[Gaeg]-[Taeg]$_4$-Lys-NH$_2$ The protected PNA was assembled onto a Boc-Lys(ClZ) modified MBHA resin with a substitution of approximately 0.15 mmol/g (determined by quantitative Ninhydrin reaction). Capping of uncoupled amino groups was only carried out before the incorporation of the BocGaeg-OH monomer.

(b) Stepwise Assembly of H—[Taeg]$_5$-[Gaeg]-(Taeg]$_4$-Lys-NH$_2$ (synthetic protocol)

Synthesis was initiated on 102 mg (dry weight) of pre-swollen (overnight in DCM) and neutralized Boc-Lys(ClZ)-MBHA resin. The steps performed were as follows: (1) Boc-deprotection with TFA/DCM (1:1, v/v), 1×2 min and 1×½ h, 3 ml; (2) washing with DCM, 4×20 sec, 3 ml; washing with DMF, 2×20 sec, 3 ml; washing with DCM, 2×20 sec, 3 ml, and drain for 30 sec; (3) neutralization with DIEA/DCM (1:19 v/v), 2×3 min, 3 ml; (4) washing with DCM, 4×20 sec, 3 ml, and drain for 1 min.; (5) addition of 4 equiv. diisopropyl carbodiimide (0.06 mmol; 9.7 μl) and 4 equiv. (0.06 mmol; 24 mg) BocTaeg-OH or (0.06 mmol; 30 mg) BocGaeg-OH dissolved in 0.6 ml DCM/DMF (1:1, v/v) (final concentration of monomer 0.1 M), the coupling reaction was allowed to proceed for ½ h shaking at room temperature; (6) suction was applied for 20 seconds (7) washing with DMF, 2×20 sec and 1×2 min, 3 ml; washing with DCM 4×20 sec, 3 ml; (8) neutralization with DIEA/ DCM (1:19 v/v), 2×3 min, 3 ml; (9) washing with DCM 4×20 sec, 3 ml, and drain for 1 min.; (10) qualitative Kaiser test; (11) blocking of unreacted amino groups by acetylation with $Ac_2O$/pyridine/DCM (1:1:2, v/v), 1×½ h, 3 ml; and (12) washing with DCM, 4×20 sec, 2×2 min and 2×20 sec, 3 ml. Steps 1–12 were repeated until the desired sequence was obtained. All qualitative Kaiser tests were negative (straw-yellow colour with no coloration of the beads) indicating near 100% coupling yield. The PNA-oligomer was cleaved and purified by the normal procedure. FAB-MS: 2832.11 [M*+1·(calc. 2832.15)

EXAMPLE 53

Solid-Phase Synthesis of H-Taeg-Aaeg-[Taeg]$_8$-Lys-NH$_2$ (a) Stepwise Assembly of Boc-Taeg-A(Z)aeg-[Taeg]$_8$-Lys (ClZ)-MBHA Resin.

About 0.3 g of wet Boc-(Taeg]$_8$-Lys(ClZ)-MBHA resin was placed in a 3 ml SPPS reaction vessel. Boc-Taeg-A(Z) aeg-[Taeg]$_8$-Lys(ClZ)-MBHA resin was assembled by in situ DCC coupling (single) of the A(Z)aeg residue utilizing 0.19 M of BocA(Z)aeg-OH together with 0.15 M DCC in 2.5 ml 50% DMF/$CH_2Cl_2$ and a single coupling with 0.15 M BocTaeg-OPfp in neat $CH_2Cl_2$ ("Synthetic Protocol 5"). The synthesis was monitored by the quantitative ninhydrin reaction, which showed about 50% incorporation of A(Z)aeg and about 96% incorporation of Taeg.

(b) Cleavage, Purification, and Identification of H-Taeg-Aaeg-[Taeg]$_8$-Lys-NH$_2$.

The protected Boc-Taeg-A(Z)aeg-[Taeg]$_8$-Lys(ClZ)-BAH resin was treated as described in Example 40c to yield about 15.6 mg of crude material upon HF cleavage of 53.1 mg dry H-Taeg-A(Z)aeg-[Taeg]$_8$-Lys(ClZ)-BHA resin. The main peak at 14.4 min accounted for less than 50% of the total absorbance. A 0.5 mg portion of the crude product was purified to give approximately 0.1 mg of H-Taeg-Aaeg-[Taeg]$_8$-Lys-NH$_2$. For (MH+)$^+$ the calculated m/z value was 2816.16 and the measured m/z value was 2816.28.

(c) Synthetic Protocol 5

(1) Boc-deprotection with TFA/$CH_2Cl_2$ (1:1, v/v), 2.5 ml, 3×1 min and 1×30 min; (2) washing with $CH_2Cl_2$, 2.5 ml, 6×1 min; (3) neutralization with DIEA/$CH_2Cl_2$ (1:19, v/v), 2.5 ml, 3×2 min; (4) washing with $CH_2Cl_2$, 2.5 ml, 6×1 min, and drain for 1 min; (5) 2–5 mg sample of PNA-resin is taken out and dried thoroughly for a quantitative ninhydrin analysis to determine the substitution; (6) addition of 0.47 mmol (0.25 g) BocA(Z)aeg-OH dissolved in 1.25 ml DMF followed by addition of 0.47 mmol (0.1 g) DCC in 1.25 ml $CH_2Cl_2$ or 0.36 mmol (0.20 g) BocTaeg-OPfp in 2.5 ml $CH_2Cl_2$; the coupling reaction was allowed to proceed for a total of 20–24 hrs shaking; (7) washing with DMF, 2.5 ml, 1×2 min; (8) washing with $CH_2Cl_2$, 2.5 ml, 4×1 min; (9) neutralization with DIEA/$CH_2Cl_2$ (1:19, v/v), 2.5 ml, 2×2 min; (10) washing with $CH_2Cl_2$, 2.5 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/pyridine/$CH_2Cl_2$ (1:1:2, v/v/v) for 2 h (except after the last cycle); and (13) washing with $CH_2Cl_2$, 2.5 ml, 6×1 min; (14) 2×2–5 mg samples of protected PNA-resin are taken out, neutralized with DIEA/$CH_2Cl_2$ (1:19, v/v) and washed with $CH_2Cl_2$ for ninhydrin analyses.

EXAMPLE 54

Solid-Phase Synthesis of H—[Taeg]$_2$-Aaeg-[Taeg]$_5$-Lys-NH$_2$ (a) Stepwise Assembly of Boc-[Taeg]$_2$-A(Z)aeg-[Taeg]$_5$-Lys(ClZ)-MBHA Resin.

About 0.5 g of wet Boc-[Taeg]$_5$-Lys(ClZ)-MBHA resin was placed in a 5 ml SPPS reaction vessel. Boc-[Taeg]$_2$-A(Z)aeg-[Taeg]$_5$-Lys(ClZ)-MBHA resin was assembled by in situ DCC coupling of both the A(Z)aeg and the Taeg residues utilising 0.15 M to 0.2 M of protected PNA monomer (free acid) together with an equivalent amount of DCC in 2 ml neat CH$_2$Cl$_2$ ("Synthetic Protocol 6"). The synthesis was monitored by the quantitative ninhydrin reaction which showed a total of about 82% incorporation of A(Z)aeg after coupling three times (the first coupling gave about 50% incorporation; a fourth HOBt-mediated coupling in 50% DMF/CH2Cl2 did not increase the total coupling yield significantly) and quantitative incorporation (single couplings) of the Taeg residues.

(b) Cleavage, Purification, and Identification of H—[Taeg]$_2$-Aaeg-[Taeg]$_5$-Lys-NH$_2$.

The protected Boc-[Taeg]$_2$-A(Z)aeg-[Taeg]$_5$-Lys(ClZ)-BHA resin was treated as described in Example 40c to yield about 16.2 mg of crude material upon HF cleavage of 102.5 mg dry H—[Taeg]$_2$-A(Z)aeg-[Taeg]$_5$-Lys(ClZ)-BHA resin. A small portion of the crude product was purified. For (MH+)$^+$, the calculated m/z value was 2050.85 and the measured m/z value was 2050.90

(c) Synthetic Protocol 6

(1) Boc-deprotection with TFA/CH$_2$Cl$_2$ (1:1, v/v), 2 ml, 3×1 min and 1×30 min; (2) washing with CH$_2$Cl$_2$, 2 ml, 6×1 min; (3) neutralization with DIEA/CH$_2$Cl$_2$ (1:19, v/v), 2 ml, 3×2 min; (4) washing with CH$_2$Cl$_2$, 2 ml, 6×1 min, and drain for 1 min; (5) 2–5 mg sample of PNA-resin was taken out and dried thoroughly for a quantitative ninhydrin analysis to determine the substitution; (6) addition of 0.44 mmol (0.23 g) BOcA(Z)aeg-OH dissolved in 1.5 ml CH$_2$Cl$_2$ followed by addition of 0.44 mmol (0.09 g) DCC in 0.5 ml CH$_2$Cl$_2$ or 0.33 mmol (0.13 g) BocTaeg-OH in 1.5 ml CH$_2$Cl$_2$ followed by addition of 0.33 mmol (0.07 g) DCC in 0.5 ml CH$_2$Cl$_2$; the coupling reaction was allowed to proceed for a total of 20–24 hrs with shaking; (7) washing with DMF, 2 ml, 1×2 min; (8) washing with CH$_2$Cl$_2$, 2 ml, 4×1 min; (9) neutralization with DIEA/CH$_2$Cl$_2$ (1:19, v/v), 2 ml, 2×2 min; (10) washing with CH$_2$Cl$_2$, 2 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/pyridine/CH$_2$Cl$_2$ (1:1:2, v/v/v) for 2 h (except after the last cycle); (13) washing with CH$_2$Cl$_2$, 2 ml, 6×1 min; and (14) 2×2–5 mg samples of protected PNA-resin were taken out, neutralized with DIEA/CH$_2$Cl$_2$ (1:19, v/v) and washed with CH$_2$Cl$_2$ for ninhydrin analyses.

EXAMPLE 55

An example with a "no base" substitution.

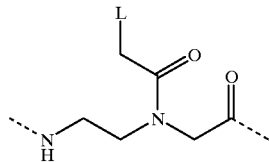

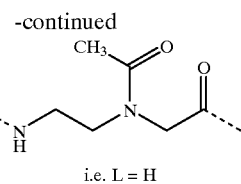

i.e. L = H

| PNA | DNA | | T$_m$ |
|---|---|---|---|
| H-T$_{10}$-LysNH$_2$ | (dA)$_{10}$ | (See ID SEQ NO:10) | 73° C. |
| H-T$_4$(Ac)T$_5$-LysNH$_2$ | (dA)$_{10}$ | | 49° C. |
| H-T$_4$(AC)T$_5$-LysNH$_2$ | (dA)$_4$(dG)(dA)$_5$ | (See ID SEQ NO:3) | 37° C. |
| H-T$_4$(Ac)T$_5$-LysNH$_2$ | (dA)$_4$(dC)(dA)$_5$ | (See ID SEQ NO:4) | 41° C. |
| H-T$_4$(Ac)T$_5$-LysNH$_2$ | (dA)$_4$(dT)(dA)$_5$ | | 41° C. |
| H-T$_4$(Ac)T$_5$-LysNH$_2$ | (dA)$_5$(dG)(dA)$_4$ | | 36° C. |
| H-T$_4$(Ac)T$_5$-LysNH$_2$ | (dA)$_5$(dC)(dA)$_4$ | (See ID SEQ NO:6) | 40° C. |
| H-T$_4$(Ac)T$_5$-LysNH$_2$ | (dA)$_5$(dT)(dA)$_4$ | (See ID SEQ NO:7) | 40° C. |

Thus it can be seen that compared with H-T$_{10}$-LysNH$_2$, replacement of one thymine ligand by H results in a drop of Tm to 48° C. from 73° C. The effect of also introducing a single base mismatch is also shown.

Certain biochemical/biological properties of PNA ligomers are illustrated by the following experiments.

1. Sequence Discrimination at the dsDNA Level (Example 63, FIG. 20)

Using the S$_1$-nuclease probing technique, the disrimination of binding of the T$_{10}$, T$_5$CT$_4$ (T$_9$C) & T$_2$CT$_2$CT$_4$ T$_8$C$_2$) PNA to the recognition sequences A$_{10}$, A$_5$GA$_4$ (A$_9$G) & A$_2$GA$_2$GA$_4$ (A$_8$G$_2$) cloned into the BamHI, SalI or PstI site of the plasmid pUC19 was analyzed. The results (FIG. 20) show that the three PNAs bind to their respective recognition sequences with the following relative efficiencies: PNA-T$_{10}$: A$_{10}$>A$_9$G>>A$_8$G$_2$, PNA-T$_9$C: A$_9$G>A$_{10}$>>A$_8$G$_2$, PNA-T$_8$C$_2$: A$_8$G$_2$≧A$_9$G>>A$_{10}$. Thus at 37° C. one mismatch out of ten gives reduced efficiency (5–10 times estimated) whereas two mismatches are not accepted.

2. Displacement of a Single Strand DNA from a ds-DNA by Hybridisation of PNAs T$_{10}$/T$_9$C/T$_8$C$_2$ (FIG. 20)—Example 63

3. Kinetics of PNA-T$_{10}$-dsDNA Strand Displacement Complex Formation (Example 64, FIG. 21)

Figure 21:
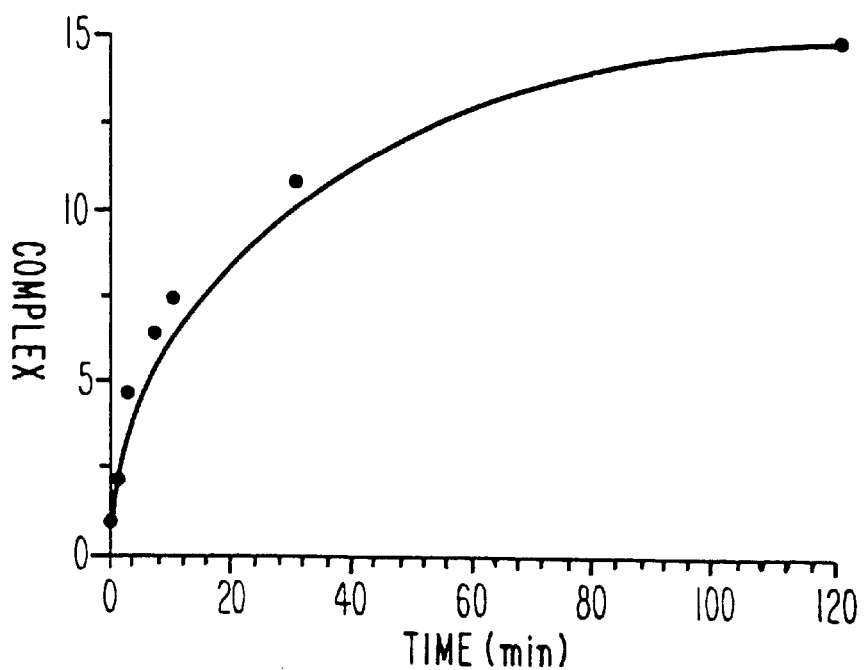
FIG. 21 shows a graph based on densitometric scanning of PAGE autoradiographs demonstrating the kinetics of the binding of PNA-$T_{10}$ to a double stranded target.

Complex formation was probed by S$_1$-nuclease at various times following mixing of PNA and $^{32}$P-end labelled dsDNA fragment (FIG. 21).

4. Stability of PNA-dsDNA Complex (Example 65, FIG. 22)

Complexes between PNA-T$_n$ and $^{32}$P-dsDNA (A$_{10}$/T$_{10}$) target were formed (60 min, 37° C.). The complexes were then incubated at the desired temperature in the presence of excess oligo-dA$_{10}$ for 10 min, cooled to RT and probed with KMnO$_4$. The results (FIG. 22) show that the thermal stability of the PNA-dsDNA complexes mirror that of the PNA oligonucleotide complexes in terms of "Tm".

5. Inhibition of Restriction Enzyme Cleavage by PNA (Example 64, FIG. 23)

Figure 23:
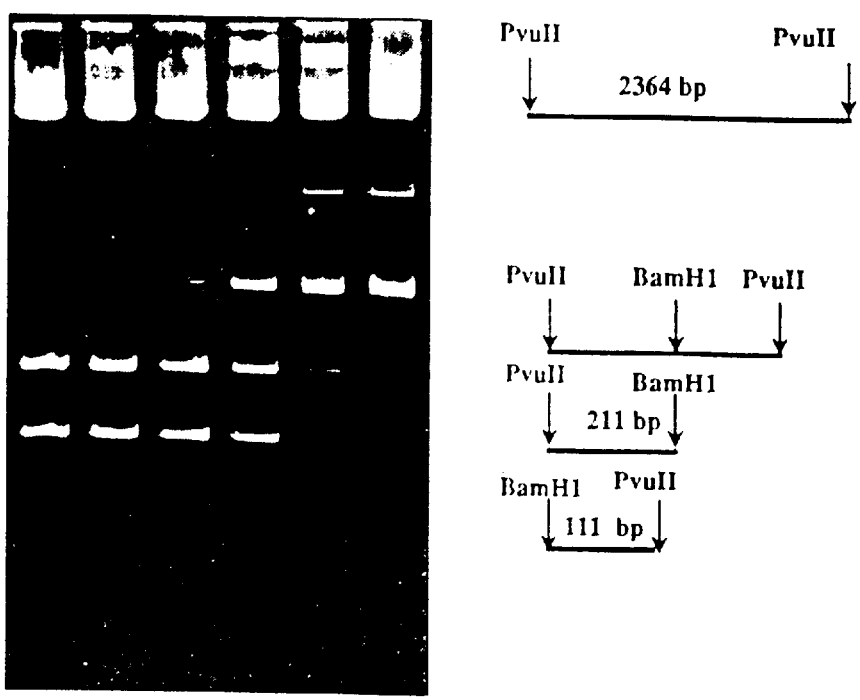
FIG. 23 show an electrophoretic gel staining demonstrating that restriction enzyme activity towards DNA is inhibited when PNA is bound proximal to the restriction enzyme recognition site.

The plasmid construct, pT10, contains a $dA_{10}/dT_{10}$ tract cloned into the BamHI site in pUC19. Thus, cleavage of pT10 with BamHI and PvuII results in two small DNA fragments of 211 and 111 bp, respectively. In the presence of PNA-$T_{10}$, a 336 bp fragment is obtained corresponding to cleavage only by PvuII (FIG. 23). Thus cleavage by BamHI is inhibited by PNA bound proximal to the restriction enzyme site. The results also show that the PNA-dsDNA complex can be formed in 100% yield. Similar results were obtained using the pTSC2 plasmid and PNA-T8C2.

6. Binding of $^{125}$I-labeled PNA to Oligonucleotides (Example 63, FIG. 24)

Figure 24:
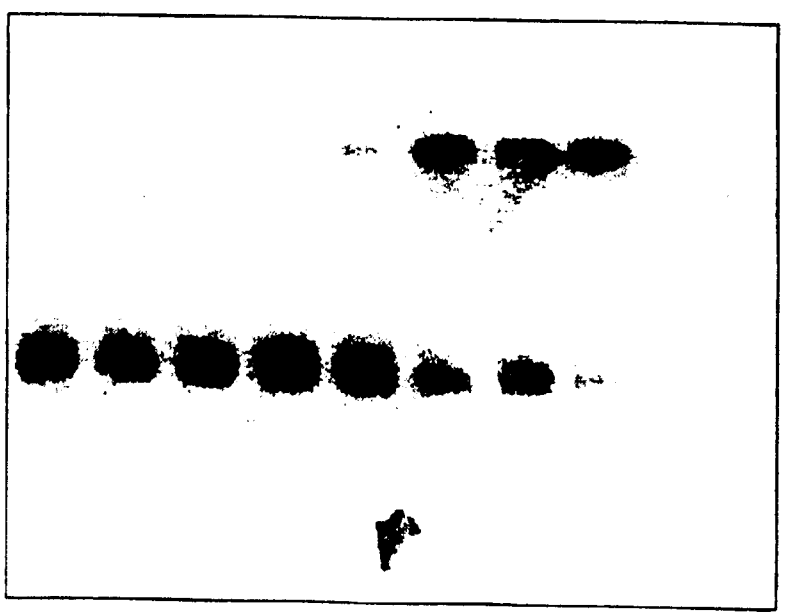
FIG. 24 shows a PAGE autoradiograph demonstrating that $^{125}$I-labeled PNA-$T_{10}$ binds to a complementary $dA_{10}$ oligonucleotide.

A Tyr-PNA-$T_{10}$-Lys-$NH_2$ was labeled with 125I using $Na^{125}I$ and chloramine-T and purified by HPLC. The $^{125}$I-PNA-$T_{10}$ was shown to bind to oligo-$dA_{10}$ by PAGE and autoradiography (FIG. 24). The binding could be competed by excess denatured calf thymus DNA.

Figure 11A:
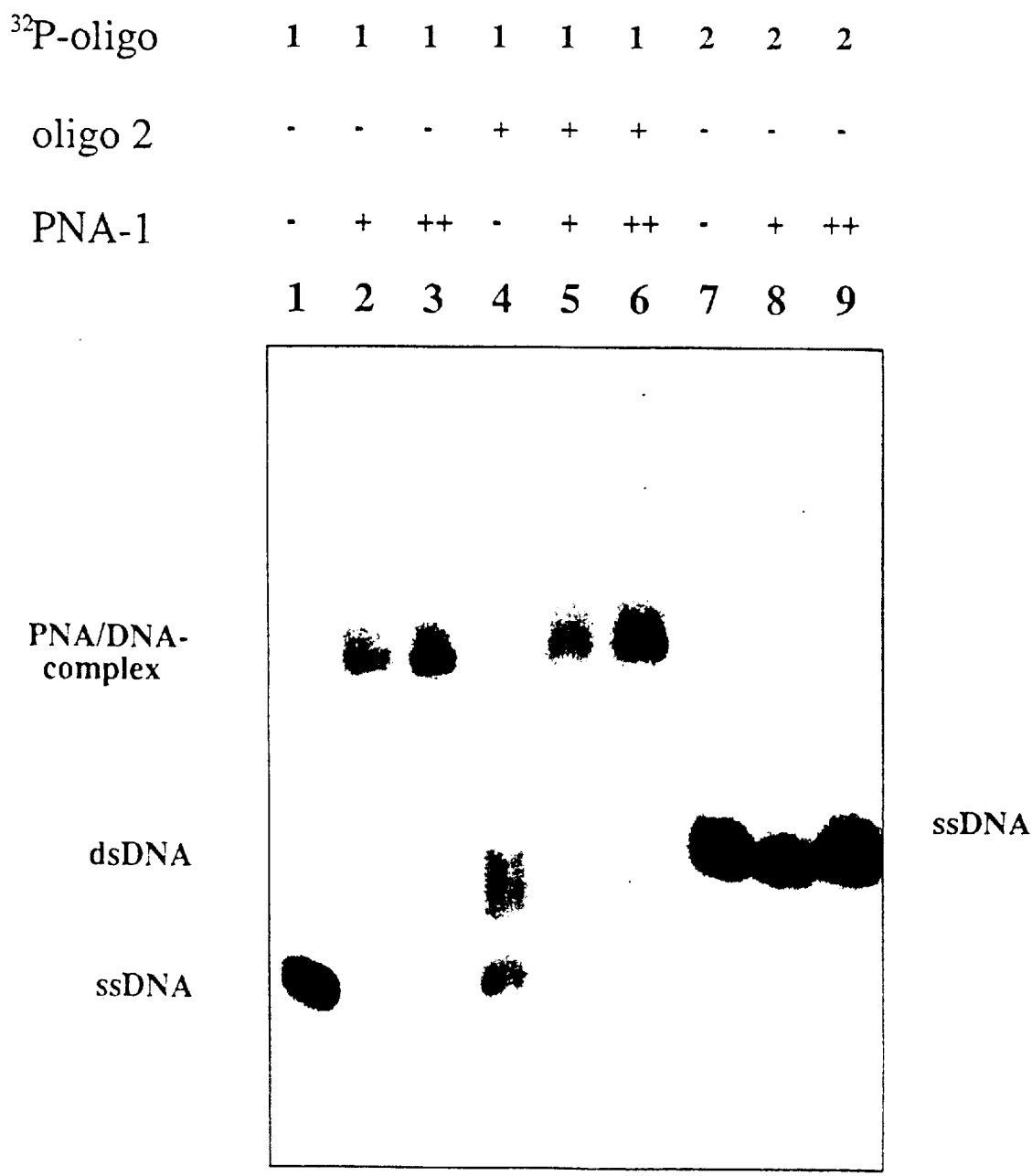
FIGS. 11a and 11b show binding of $AcrT_{10}$-Lys to $dA_{10}$. 5'-$^{32}$P-labelled oligonucleotide (1) (5'-$GATCCA_{10}G$) ID SEQ NO:22 was incubated in the absence or presence of $AcrT_{10}$-Lys and in the absence or presence of oligonucleotide (2) (5'-$GATCCT_{10}G$) and the samples were analyzed by polyacrylamide gel electrophoresis (PAGE) and autoradiography under "native conditions" (FIG. 11a) or under "denaturing conditions" (FIG. 11b).

Reverting to point (1) above, the sequence-specific recognition of dsDNA is illustrated by the binding of a PNA, consisting of 10 thymine substituted 2-aminoethylglycyl units, which C-terminates in a lysine amide and N-terminates in a complex 9-aminoacridine ligand (9-$Acr^1$-$(Taeg)_{10}$-Lys-$NH_2$, FIGS. 11a and b) to a $dA_{10}/dT_{10}$ target sequence. The target is contained in a 248 bp $^{32}$P-end-labelled DNA-fragment.

Figure 5:
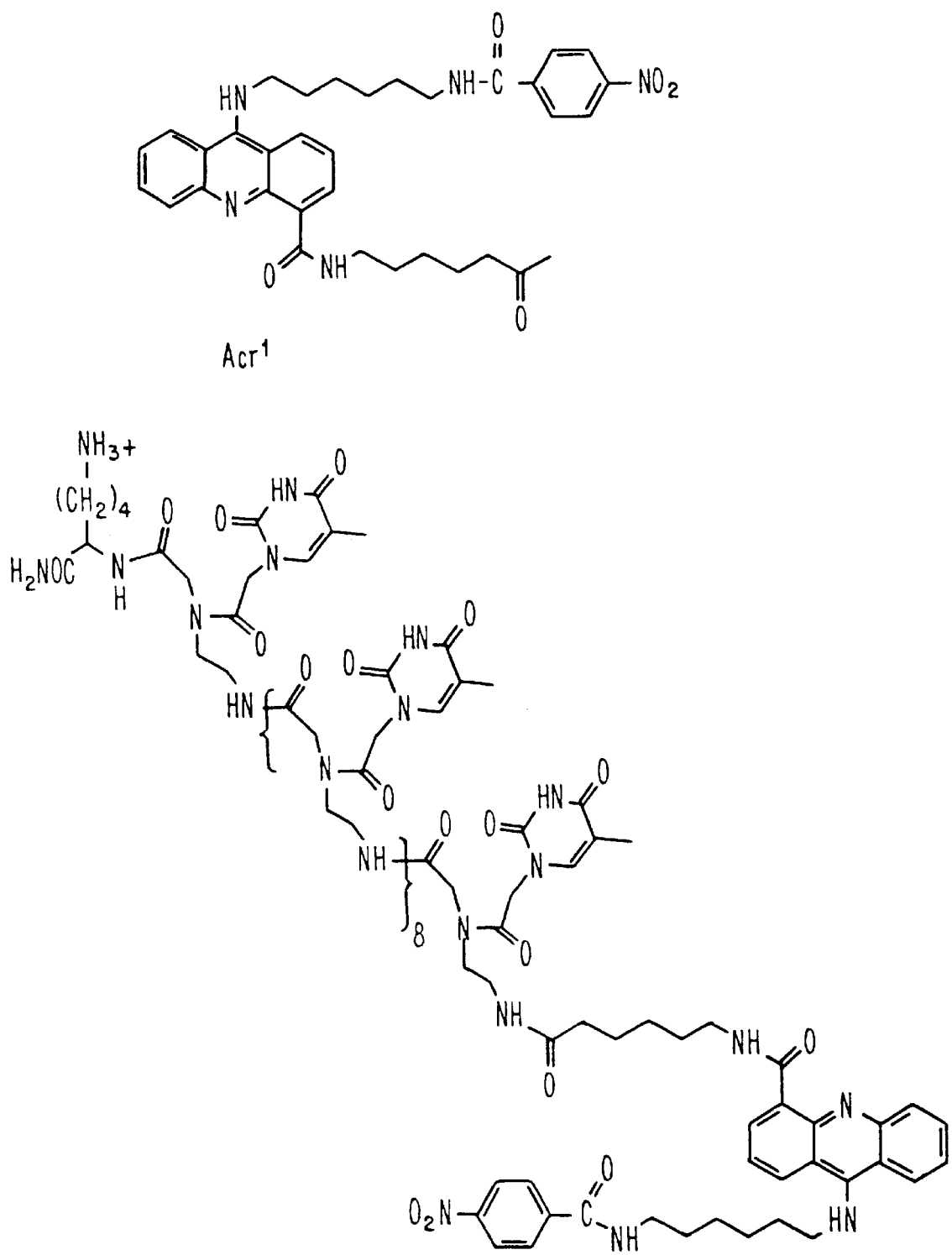
FIG. 5 shows the Acr1 ligand and a PNA, $Acr^1$-$(Taeg)_{10}$-Lys-$NH_2$.
Figure 6:
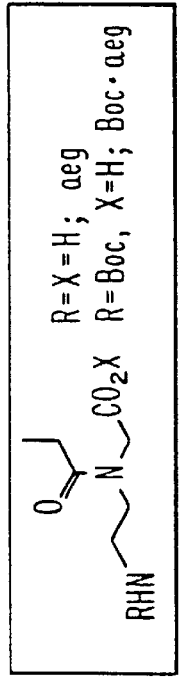
FIG. 6 provides a general scheme for the preparation of monomer synthons.
Figure 6:
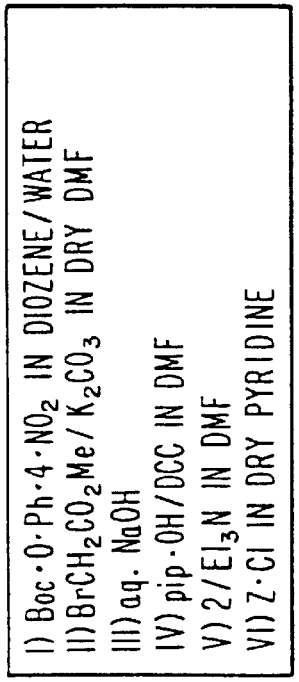
Figure 6:
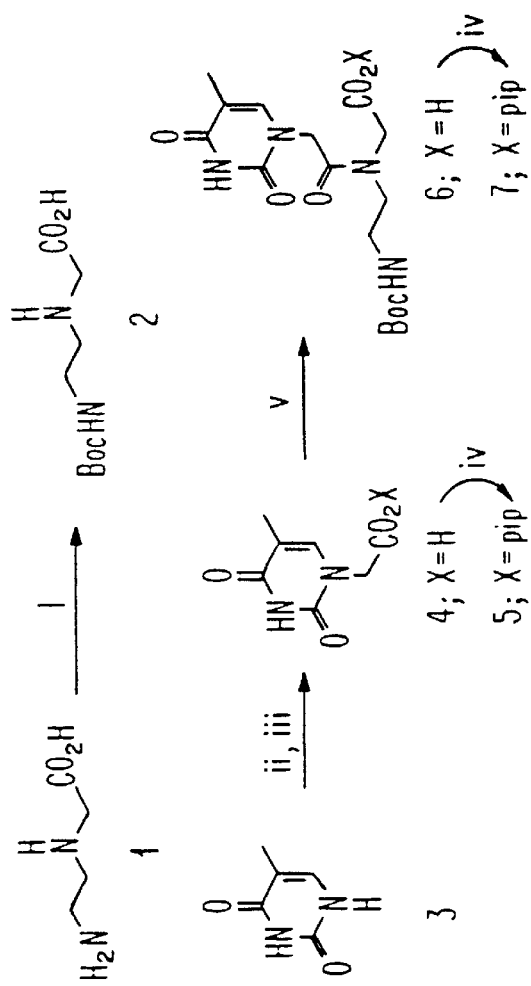
Figure 6:
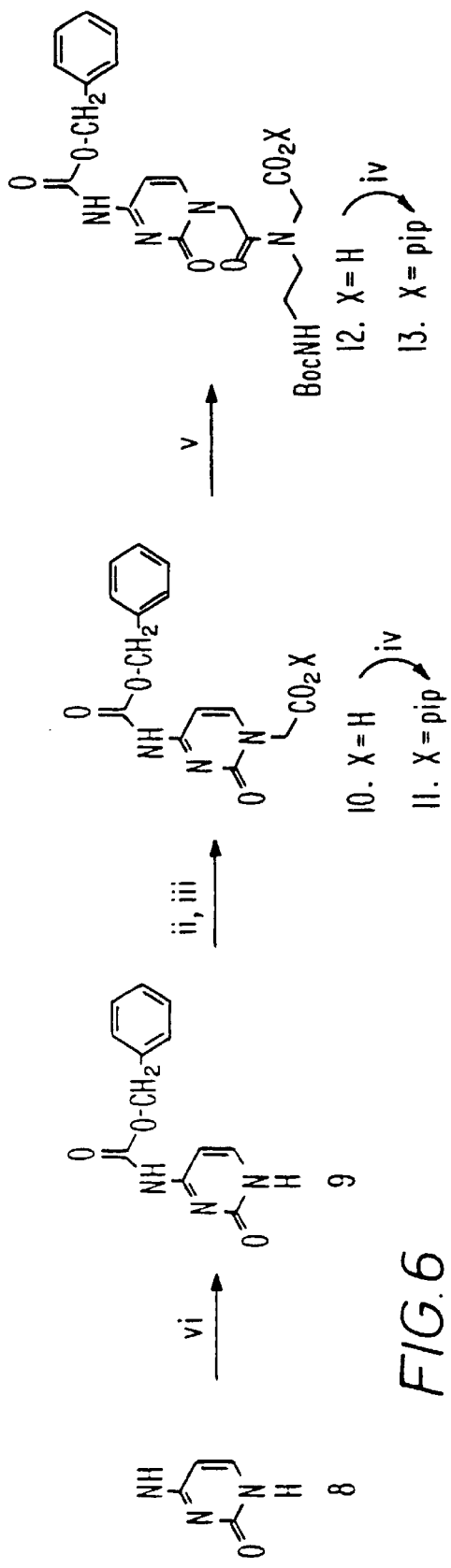
Figure 7:
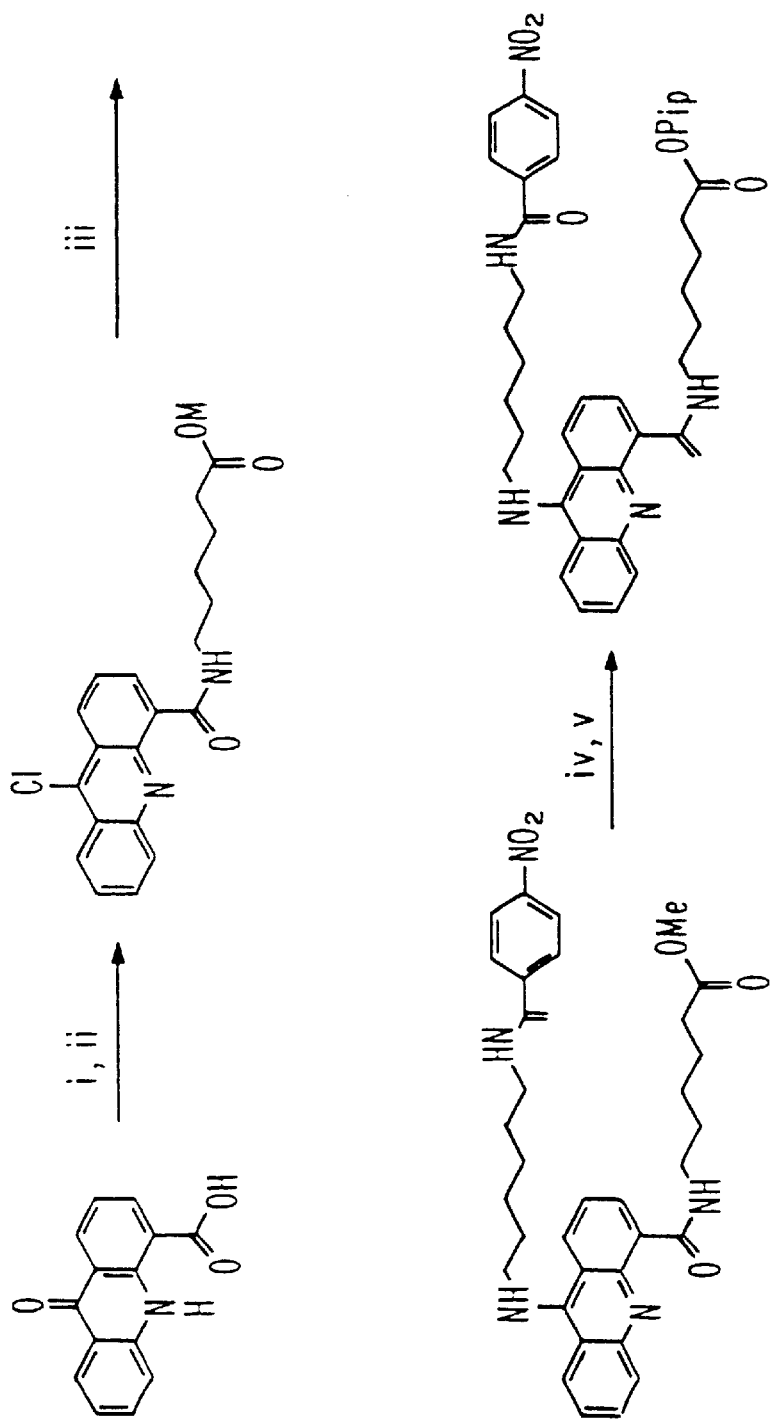
FIG. 7 provides a general scheme for the preparation of the $Acr^1$ ligand.

Strand displacement was ascertained by the following type of experiments:

1) The 9-$Acr^1$ ligand (FIG. 5), which is equipped with a 4-nitrobenzamido group to ensure cleavage of DNA upon irradiation, is expected only to cleave DNA in close proximity to its binding site. Upon irradiation of the PNA with the above 248 bp DNA fragment, selective cleavage at the $dA_{10}/dT_{10}$ sequence is observed (FIG. 3a).

2) In a so-called photofootprinting assay, where a synthetic diazo-linked acridine under irradiation cleaves DNA upon interaction with DNA (except where the DNA is protected by said binding substance).

Figure 3:
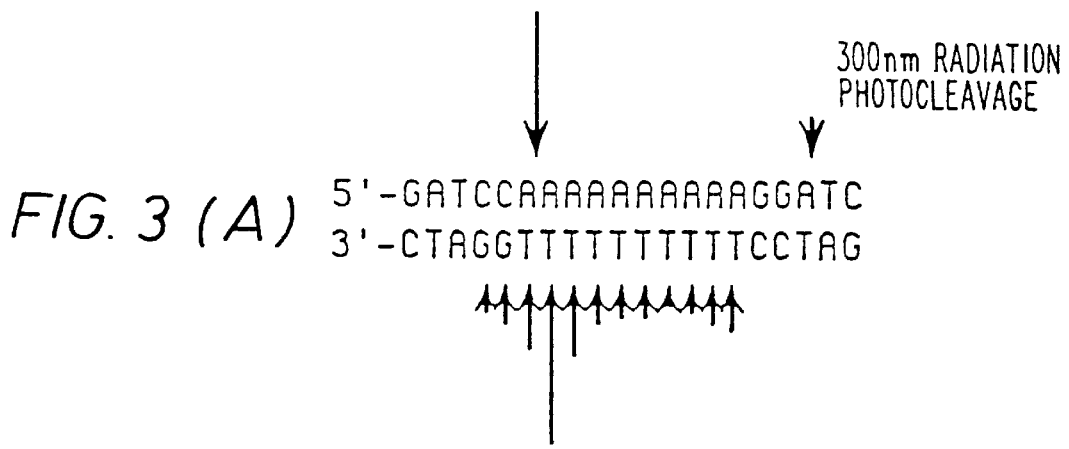
FIGS. 3(A), 3(B), 3(C), and 3(D) provide a schematic illustration of photocleavage by $Acr^1$-$(Taeg)_{10}$-Lys-$NH_2$ (Acr $T_{10}$ Lys-$NH_2$); photofootprint by the diazo-linked acridine of $Acr^1$-$(Taeg)_{10}$-Lys-$NH_2$ and preferred $KMnO_4$-cleavage; and $S_1$-nuclease enhanced cleavage and micrococcus nuclease cleavage of $Acr^1$-$(Taeg)_{10}$-Lys-$NH_2$ binding site, respectively. The sequence shown in the figure is double stranded (See ID SEQ NO:8).
Figure 3:
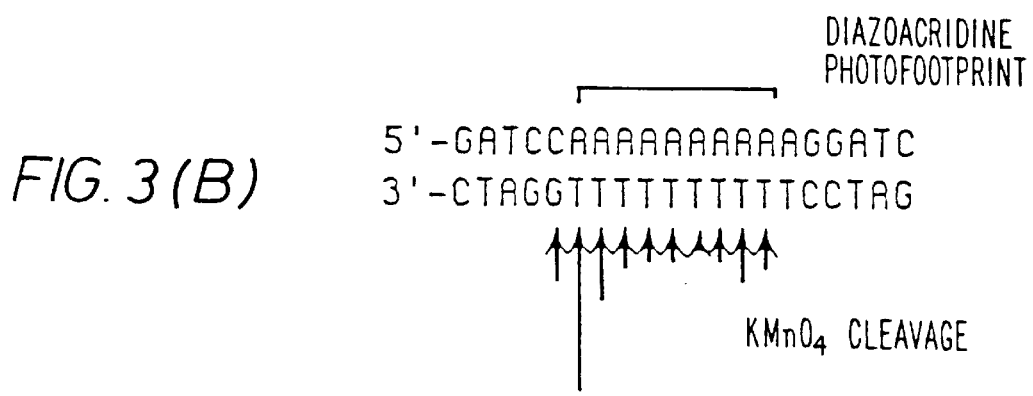
Figure 3:
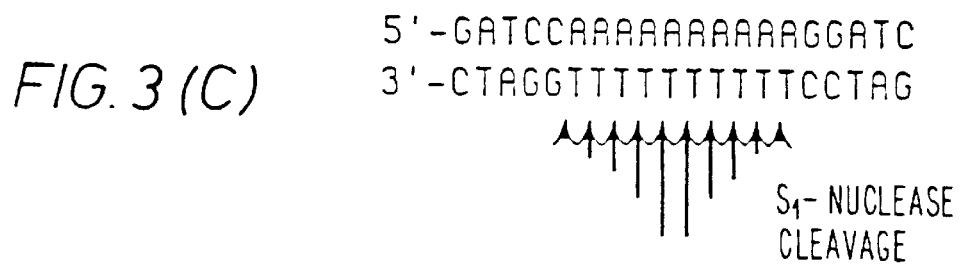
Figure 3:
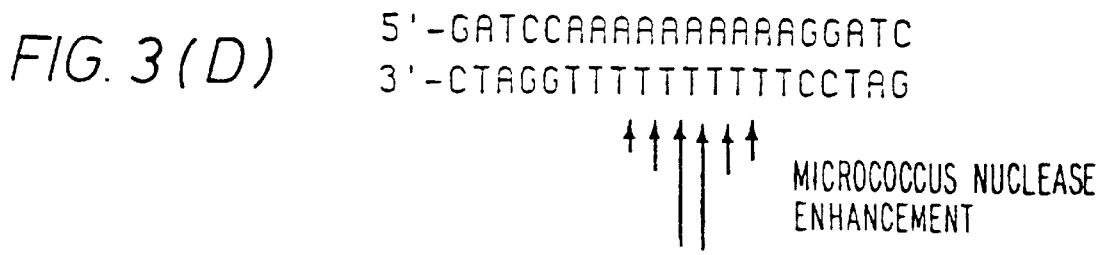

Such an experiment was performed with the above 248 bp dsDNA fragment, which showed clear protection against photocleavage of the PNA binding site (FIG. 3b).

3) In a similar type of experiment, the DNA-cleaving enzyme micrococcus nuclease, which is also hindered in its action by most DNA-binding reagents, showed increased cleavage at the $T_{10}$-target (FIG. 3c).

4) In yet another type of experiment, the well-known high susceptibility of single strand thymine ligands (as opposed to double strand thymine ligands) towards potassium permanganate oxidation was employed. Oxidation of the 248 bp in the presence of the reagent showed only oxidation of the $T_{10}$-strand of the target (FIG. 3b).

5) In a similar type of demonstration, the single strand specificity of $S_1$ nuclease clearly showed that only the $T_{10}$-strand of the target was attacked (FIG. 3d).

The very efficient binding of $(Taeg)_{10}$, $(Taeg)_{10}$-Lys-$NH_2$ and $Acr^1$-$(Taeg)_{10}$-Lys-$NH_2$ (FIG. 5) to the corresponding $dA_{10}$ was furthermore illustrated in two ways:

1. As shown in Example 56 below PNA-oligonucleotide complexes will migrate slower than the single stranded oligonucleotide upon electrophoresis in polyacrylamide gels. Consequently, such experiments were performed with $Acr^1$-$(Taeg)_{10}$-Lys-$NH_2$ and $^{32}$P-end-labelled $dA_{10}$. This showed retarded migration under conditions where a normal $dA_{10}/dT_{10}$ duplex is stable, as well as under conditions where such a duplex is unstable (denaturing gel). A control experiment was performed with a mixture of $Acr^1$-$(Taeg)_{10}$-Lys-$NH_2$ and $^{32}$P-end-labelled $dT_{10}$ which showed no retardation under the above conditions.

2. Upon formation of DNA duplexes (dsDNA) from single strand DNA, the extinction coefficient decreases (hypochromicity). Thus, the denaturing of DNA can be followed by measuring changes in the absorbance, for example, as a function of $T_m$, the temperature where 50% of a duplex has disappeared to give single strands.

Duplexes were formed from the single-stranded oligodeoxyribonucleotides and the PNAs listed below. Typically 0.3 $OD_{260}$ of the T-rich strand was hybridized with 1 equivalent of the other strand by heating to 90° C. for 5 min, cooling to room temperature and kept for 30 min and finally stored in a refrigerator at 5° C. for at least 30 min. The buffers used were all 10 mM in phosphate and 1 mM in EDTA. The low salt buffer contained no sodium chloride, whereas the medium salt buffer contained 140 mM NaCl and the high salt buffer 500 mM NaCl. The pH of all the buffers was 7.2. The melting temperature of the hybrids were determined on a Gilford Response apparatus. The following extinction coefficients were used A: 15.4 ml/$\mu$mol.cm; T: 8.8; G: 11.7 and C: 7.3 for both normal oligonucleotides and PNA. The melting curves were recorded in steps of 0.5 C/min. The $T_m$ were determined from the maximum of the 1st derivative of the plot of $A_{260}$ vs temperature.

List of oligodeoxyribonucleotides:
1. 5'-AAA-AAA-AA (See SEQ ID NO:12)
2. 5'-AAA-AAA-AAA-A (See SEQ ID NO:1)
3. 5'-TTT-TTT-TTT-T (See SEQ ID NO:11)
4. 5'-AAA-AAG-AAA-A (See SEQ ID NO:5)
5. 5'-AAG-AAG-AAA-A (See SEQ ID NO:9)
6. 5'-AAA-AGA-AAA-A (See SEQ ID NO:2)
7. 5'-AAA-AGA-AGA-A (See SEQ ID NO:13)
8. 5'-TTT-TCT-TTT-T (See SEQ ID NO:14)
9. 5'-TTT-TCT-TCT-T (See SEQ ID NO:15)
10. 5'-TTT-TTC-TTT-T (See SEQ ID NO:16)
11. 5'-TTT-TTC-TTC-T (See SEQ ID NO:17)
12. 5'-TTC-TTC-TTT-T (See SEQ ID NO:18)
13. 5'-TTT-TTT-TTT-TTT-TTT (See SEQ ID NO:19)
14. 5'-AAA-AAA-AAA-AAA-AAA (See SEQ ID NO:20)

| Oligo/PNA | Low Salt | Medium Salt | High Salt |
|---|---|---|---|
| 1 + b | 56.0 | 51.5 | 50.0 |
| 2 + a | 73.0 | 72.5 | 73.0 |
| 2 + c |  | 41.5 and 52.0* |  |
| 2 + e | 84.5 | 86.0 | ~90 |
| 2 + f |  | 74 |  |
| 4 + a | 60.0 | 59.0 | 61.5 |
| 4 + c | 74.5 | 72.0 | 72.5 |
| 4 + f |  | 62.0 |  |
| 5 + a |  | 47.0 |  |
| 5 + c |  | 57.5 |  |
| 5 + f |  | 46.5 |  |
| 7 + a |  | 46.0 |  |
| 7 + c |  | 58.0 |  |
| 7 + f |  | 43.5 |  |

-continued

| Oligo/PNA | Low Salt | Medium Salt | High Salt |
|---|---|---|---|
| 7 + 12 |  | 23.0 |  |
| 13 + 14 |  | 39.0 |  |

\* = Two distinct melting temperatures are seen, indicating local melting before complete denaturation List of PNAs
a. TTT-TTT-TTT-T-Lys-NH$_2$
b. TTT-TTT-TT-Lys-NH$_2$
c. TTT-TTC-TTT-T-Lys-NH$_2$
d. TTC-TTC-TTT-T-Lys-NH$_2$
e. Acr-TTT-TTT-TTT-T-Lys-NH$_2$
f. Ac-TTT-TTT-TTT-T-Lys-NH$_2$ The hybrid formed between RNA-A (poly rA) and PNA-T$_{10}$-Lys-NH$_2$ melts at such high temperature that it cannot be measured (>90 C). But specific hybridization is demonstrated by the large drop in A$_{260}$ by mixing with RNA-A but not G, C and U. The experiment is done by mixing 1 ml of a solution of the PNA and 1 ml of a solution the RNA, each with A$_{260}$=0.6, and then measuring the absorbance at 260 nm. Thereafter the sample is heated to 90° C. for 5 min, cooled to room temperature and kept at this temperature for 30 minutes and finally stored at 5° C. for 30 min.

| RNA | PNA | A$_{260}$ Before Mixing | A$_{260}$ After Mixing | A$_{260}$ After Mixing and Heating |
|---|---|---|---|---|
| RNA-A | PNA-T$_{10}$lys-NH$_2$ | 0.600 | 0.389 | 0.360 |
| RNA-U | PNA-T$_{10}$-lys-NH$_2$ | 0.600 | 0.538 | 0.528 |
| RNA-G | PNA-T$_{10}$-lys-NH$_2$ | 0.600 | 0.514 | 0.517 |
| RNA-C | PNA-T$_{10}$-lys-NH$_2$ | 0.600 | 0.540 | 0.532 |

From the above measurements the following conclusions can be made. There is base stacking, since a melting curve is observed. The PNA-DNA hybrid is more stable than a normal DNA-DNA hybrid, and the PNA-RNA is even more stable. Mismatches cause significant drops in the T$_m$-value, whether the mispaired base is in the DNA or in the PNA-strand. The T$_m$-value is only slightly dependent on ionic strength, as opposed to normal oligonucleotides.

EXAMPLE 56

Binding of Acr$^1$-(Taeg)$_{10}$-Lys-NH$_2$ to dA$_{10}$ (FIG. 11a)

Acr$^1$-(Taeg)$_{10}$-Lys (100 ng) was incubated for 15 min at room temperature with 50 cps 5'-[$^{32}$P]-end-labelled oligonucleotide [d(GATCCA$_{10}$G)] in 20 μl TE buffer (10 mM Tris-HCl, 1 mM EDTA, pH 7.4). The sample was cooled in ice (15 min) and analyzed by gel electrophoresis in polyacrylamide (PAGE). To 10 μl of the sample was added 2 μl 50% glycerol, 5μl TBE (TBE=90 mM Tris-borate, 1 mM EDTA, pH 8.3), and the sample was analysed by PAGE (15% acrylamide, 0.5% bisacrylamide) in TBE buffer at 4° C. A 10 μl portion of the sample was lyophilized and redissolved in 10 μl 80% formamide, 1 TBE, heated to 90° C. (5 min), and analyzed by urea/PAGE (15% acrylamide, 0.5% bisacrylamide, 7 M urea) in TBE. [$^{32}$P]-containing DNA bands were visualized by autoradiography using intensifying screens and Agfa Curix RPI X-ray films exposed at −80° C. for 2 h.

Oligonucleotides were synthesized on a Biosearch 7500 DNA synthesizer, labelled with γ[$^{32}$P]-ATP (Amersham, 5000 Ci/mmol) and polynucleotide kinase, and purified by PAGE using standard techniques (Maniatis et al. (1986): A laboratory manual, Cold Spring Harbor Laboratories).

Figure 11B:
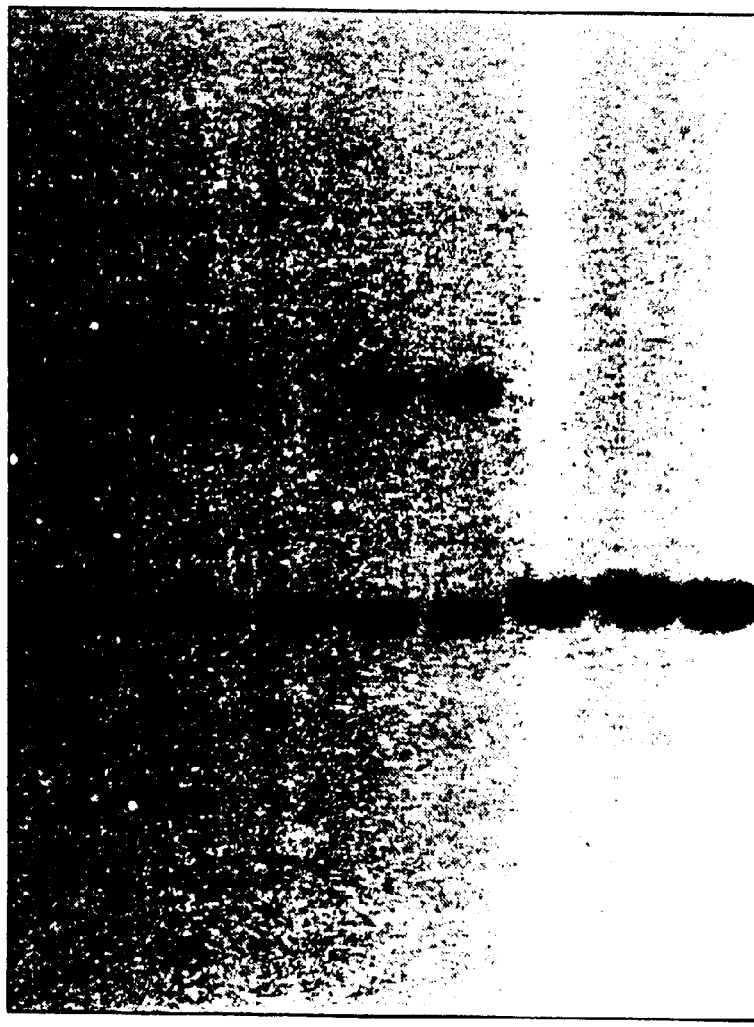

In FIG. 11a and in FIG. 11b, the 5'-$^{32}$P-labelled oligonucleotide 1 is 5'-GATCCA$_{10}$G. This was incubated in the absence (lanes 1 and 4) or presence of Acr-T$_{10}$-Lys-NH$_2$ (in lanes 2 and 5, 25 pmol; lanes 3 and 6, 75 pmol) and also in the absence (lanes 1 to 3) or presence (lanes 4 to 6) of "oligo-2" which was 5'-GATCCT$_{10}$G. 5'-$^{32}$P-labelled oligo 2 was incubated in the absence (lane 7) or presence of the same PNA (lane 8, 25 pmol; lane 9, 75 pmol) and analysed by PAGE as described above in detail.

The results in FIG. 11a show retardation of the ssDNA as it is hybridised by PNA (lanes 1 to 3) and the ability of PNA to compete with a DNA oligonucleotide, for labelled complementary oligonucleotide (lanes 4 to 6). The intensity of the band attributable to dsDNA grows faster as the PNA concentration is raised and is replaced by a band representing the slower moving PNA-DNA hybride. Lanes 7 to 9 show that the PNA has no effect on the Too oligo DNA with which it is non-complementary.

In FIG. 11b, which was run under DNA denaturing conditions the PNA-DNA duplexes remain undenatured.

EXAMPLE 57

Formation of strand displacement complex

A dA$_{10}$-dT$_{10}$ target sequence contained within a plasmid DNA sequence was constructed by cloning of two oligonucleotides (d(GATCCA$_{10}$G)+d(GATCCT$_{10}$G)) into the BamHI restriction enzyme site of pUC19 using the Escherichia coli JM101 strain by standard techniques (Maniatis et al., 1986). The desired plasmid (designated pT10) was isolated from one of the resulting clones and purified by the alkaline extraction procedure and CsCl centrifugation (Maniatis et al., 1986). A 3'-[$^{32}$P]-end-labelled DNA fragment of 248 bp containing the dA$_{10}$/dT$_{10}$ target sequence was obtained by cleaving the pT10 DNA with restriction enzymes EcoRI and PvuII, labelling of the cleaved DNA with α[$^{32}$P]-dATP (4000 Ci/mmol, Amersham) using the Klenow fragment of E. coli DNA polymerase (Boehringer Mannheim), and purifying the 248 bp DNA fragment by PAGE (5% acrylamide, 0.06% bisacrylamide, TBE buffer). This DNA fragment was obtained with [$^{32}$P]-end-labelling at the 5'-end by treating the EcoRI-cleaved pT10 plasmid with bacterial alkaline phosphatase (Boehringer Mannheim), purifying the plasmid DNA by gel electrophoresis in low melting temperature agarose, and labelling with γ[32P] ATP and polynucleotide kinase. Following treatment with PvuII, the 248 bp DNA fragment was purified as above.

The complex between Acr$^1$-(Taeg)$_{10}$-Lys-NH$_2$ and the 248 bp DNA fragment was formed by incubating 50 ng of Acr$^1$-(Taeg)$_{10}$-Lys-NH$_2$ with 500 cps $^{32}$P-labelled 248 bp fragment and 0.5 μg calf thymus DNA in 100 μl 25 mM Tris-HCl, 1 mM MgCl$_2$, 0.1 mM CaCl$_2$, pH 7.4 for 60 min at 37° C. as described further below.

EXAMPLE 58

Probing of strand displacement complex with
(a) Staphylococcus Nuclease (FIG. 12b lanes 8 to 10)

The strand displacement complex was formed as described above. The complex was treated with Staphylococcus nuclease (Boehringer Mannheim) at 750 U/ml for 5 min at 20° C. and the reaction was stopped by addition of EDTA to 25 mM. The DNA was precipitated with 2 vols. of ethanol, 2% potassium acetate redissolved in 80% formamide, TBE, heated to 90° C. (5 min), and analyzed by high resolution PAGE (10% acrylamide, 0.3% bisacrylamide, 7 M urea) and autoradiography. Lane 8 contains zero PNA, lane 9 40 pmol and lane 10 120 pmol. As the PNA is included, we see the emergence of footprint indicating increasing susceptability to digestion by Staphlococcus nuclease and hence increasing displacement of ssDNA from dsDNA.

(b) Affinity Photocleavage (FIGS. 12a+12b; lanes 1 to 3 in each case)

The complex was formed in TE buffer. A sample contained in an Eppendorf tube was irradiated from above at 300 nm (Philips TL 20 W/12 fluorescent light tube, 24 $Jm^{-2}s^{-1}$) for 30 min. The DNA was precipitated as above, taken up in 1 M piperidine, and heated to 90° C. for 20 min. Following lyophilization, the DNA was analysed by PAGE as above. Once again, in each case lane 1 contains no PNA, and lanes 2 and 3 contain 40 pmol and 120 pmol of PNA respectively. The DNA strand bound to PNA (the $A_{10}$ strand) cleaves at the location of the acridine ester (lanes 1 to 3 of FIG. 12a) producing a new band (arrowed) whilst the strand displaced by PNA (the $T_{10}$ strand) cleaves randomly producing a footprint.

(c) Potassium Permanganate (FIG. 12b lanes 4 to 6)

with nuclease $S_1$ (Boehringer Mannheim) at 0.5 U/ml for 5 min at 20° C. The reaction was stopped and treated further as described under "Staphylococcus nuclease". The quantity of PNA used was zero (lanes 1 to 3) or 120 pmol (lanes 4 to 6) lane 7 shows size standards. Once again, cleavage of the $T_{10}$ DNA strand displaced by PNA is seen.

EXAMPLE 59

Sensitivity of hybridisation to (1) orientation (2) pH and (3) sequence mismatch The PNA-oligomer H-T4C2TCTC-LysNH$_2$ was prepared by Synthetic Protocol 6, purified by reverse phase HPLC, and identified by FAB-mass spectrometry; found(calc.) 2746.8 (2447.15). Hybridization experiments with this sequence resolve the issue of orientation, since it is truly asymmetrical. Such experiments also resolve the issues of pH-dependency of the Tm, and the stoichiometry of complexes formed.

Hybridization experiments with the PNA-oligomer H-T$_4$C$_2$TCTC-LysNH$_2$ were performed as follows:

| Row | Hybridized with | pH | Tm | § |
|---|---|---|---|---|
| 1 | 5'-(dA)$_4$(dG)$_2$(dA)(dG)(dA)(dG) See SEQ ID NO:23 | 7.2 | 55.5 | 2:1 |
| 2 | 5'-(dA)$_4$(dG)$_2$(dA)(dG)(dA)(dG) | 9.0 | 26.0 | 2:1 |
| 3 | 5'-(dA)$_4$(dG)$_2$(dA)(dG)(dA)(dG) | 5.0 | 88.5 | 2:1 |
| 4 | 5'-(dG)(dA)(dG)(dA)(dG)$_2$(dA)$_4$ | 7.2 | 38.0 | 2:1 |
| 5 | 5'-(dG)(dA)(dG)(dA)(dG)$_2$(dA)$_4$ | 9.0 | 31.5 | — |
| 6 | 5'-(dG)(dA)(dG)(dA)(dG)$_2$(dA)$_4$ See SEQ ID NO:24 | 5.0 | 52.5 | — |
|   |   |   | 61.0 |   |
| 7 | 5'-(dA)$_4$(dG)(dT)(dA)(dG)(dA)(dG) | 7.2 | 39.0 | — |
| 8 | 5'-(dA)$_4$(dG)(dT)(dA)(dG)(dA)(dG) | 9.0 | <20 | — |
| 9 | 5'-(dA)$_4$(dG)(dT)(dA)(dG)(dA)(dG) See SEQ ID NO:25 | 5.0 | 51.5 | — |
| 10 | 5'-(dA)$_4$(dG)$_2$(dT)(dG)(dA)(dG) See SEQ ID NO:26 | 7.2 | 31.5 | — |
| 11 | 5'-(dG)$_4$(dG)$_2$(dT)(dG)(dA)(dG) | 5.0 | 50.5 | — |
| 12 | 5'-(dG)(dA)(dG)(dA)(dT)(dG)(dA)$_4$ See SEQ ID NO:27 | 7.2 | 24.5 | — |
| 13 | 5'-(dG)(dA)(dG)(dA)(dT)(dG)(dA)$_4$ | 9.0 | <20 | — |
| 14 | 5'-(dG)(dA)(dG)(dA)(dT)(dG)(dA)$_4$ | 5.0 | 57.0 | — |
| 15 | 5'-(dG)(dA)(dG)(dT)(dG)$_2$(dA)$_4$ See SEQ ID NO:28 | 7.2 | 25.0 | — |
| 16 | 5'-(dG)(dA)(dG)(dT)(dG)$_2$(dA)$_4$ | 5.0 | 39.5 | — |
|   |   |   | 52.0 |   |

§ = stoichiometry determined by UV-mixing curves
— = not determined

The complex was formed in 100 μl TE and 5 μl 20 mM KMnO$_4$ was added. After 15 s at 20° C., the reaction was stopped by addition of 50 μl 1.5 M sodium acetate, pH 7.0, 1 M 2-mercaptoethanol. The DNA was precipitated, treated with piperidine and analyzed, as above. The same PNA concentrations are used in lanes 4 to 6 as in lanes 1 to 3. Once again, one can see the emergence of a footprint showing cleavage of displaced ssDNA by permanganate.

(d) Photofootprinting (FIG. 12a lanes 5 to 6)

The complex was formed in 100 μl TE and diazo-linked acridine (0.1 μg/μl) (DHA, Nielsen et al. (1988) Nucl. Acids Res. 16, 3877–88) was added. The sample was irradiated at 365 nm (Philips TL 20 W/09N, 22 $Jm^{-2}s^{-1}$) for 30 min and treated as described for "affinity photocleavage". In the presence of PNA, (lane 6) the DNA is protected and bands corresponding to cleavage in the protected region disappear.

(e) S$_1$-nuclease (FIG. 12c lanes 1 to 3)

The complex was formed in 50 mM sodium acetate, 200 mM NaCl, 0.5% glycerol, 1 mM ZnCl$_2$, pH 4.5 and treated These results show that a truly mixed sequence gave rise to well defined melting curves. The PNA-oligomers can actually bind in both orientations (compare row 1 and 4), although there is preference for the N-terminal/5'-orientation. Introducing a single mismatch opposite either T or C caused a lowering of $T_m$ by more than 16° C. at pH 7.2; at pH 5.0 the $T_m$-value was lowered more than 27° C. This shows that there is a very high degree a sequence-selectivity.

As indicated above, there is a very strong pH-dependency for the $T_m$-value, indicating that Hoogsteen basepairing is important for the formation of hybrids. Therefore, it is not surprising that the stoichiometry was found to be 2:1.

The lack of symmetry in the sequence and the very large lowering of $T_m$ when mismatches are present show that the Watson-Crick strand and the Hoogsteen strand are parallel when bound to complementary DNA. This is true for both of the orientations, i.e., 5'/N-terminal and 3'/N-terminal.

EXAMPLE 60

Sequence discrimination in hybridisation

The results of hybridization experiments with H-T$_5$GT$_4$-LysNH$_2$ to the deoxyoligonucleotides shown below were as follows:

| Row | Deoxyoligonucleotide | T$_m$ |
|---|---|---|
| 1 | 5'-(dA)5(dA)(dA)4-3' | 55.0 |
| 2 | 5'-(dA)5(dG)(dA)4-3' | 47.0 |
| 3 | 5'-(dA)5(dC)(dA)4-3' | 56.5 |
| 4 | 5'-(dA)5(dT)(dA)4-3' | 46.5 |
| 5 | 5'-(dA)4(dG)(dA)5-3' | 48.5 |
| 6 | 5'-(dA)4(dC)(dA)5-3' | 55.5 |
| 7 | 5'-(dA)4(dT)(dA)5-3' | 47.0 |

As shown by comparing rows 1, 3, and 6 with rows 2, 4, 5, and 7, G can in this mode discriminate between C/A and G/T in the DNA-strand, i.e., sequence discrimination is observed. The complex in row 3 was furthermore determined to be 2 PNA: 1 DNA complex by UV-mixing curves.

EXAMPLE 61

Sequence specificity in hybridisation using a modified backbone

Hybridization data for a PNA-oligomer with a single unit with an extended backbone (the β-alanine modification) is as follows:

| PNA | DNA | T$_m$ |
|---|---|---|
| H-T$_{10}$-LysNH$_2$ | (dA)$_{10}$ | 73° C. |
| H-T$_4$(βT)T$_5$-LysNH$_2$ | (dA)$_{10}$ | 57° C. |
| H-T$_4$(βT)T$_5$-LysNH$_2$ | (dA)$_4$(dG)(dA)$_5$ | 47° C. |
| H-T$_4$(βT)T$_5$-LysNH$_2$ | (dA)$_4$(dC)(dA)$_5$ | 49° C. |
| H-T$_4$(βT)T$_5$-LysNH$_2$ | (dA)$_4$(dT)(dA)$_5$ | 47° C. |

Although the melting temperature decreases, the data demonstrates that base specific recognition is retained.

EXAMPLE 62

Iodination Procedure—Radiolabelling

A 5 μg portion of Tyr-PNA-T$_{10}$-Lys-NH$_2$ is dissolved in 40 μl 100 mM Na-phosphate, pH 7.0, and 1 mCi Na$^{125}$I and 2 μl chloramine-T (50 mM in CH$_3$CN) are added. The solution is left at 20° C. for 10 min and then passed through a 0.5+5 cm Sephadex G10 column. The first 2 fractions (100 μl each) containing radioactivity are collected and purified by HPLC: reversed phase C-18 using a 0–60% CH$_3$CN gradient in 0.1% CF$_3$COOH in H$_2$O. The $^{125}$I-PNA elutes right after the PNA peak. The solvent is removed under reduced pressure.

EXAMPLE 63

Figure 20:
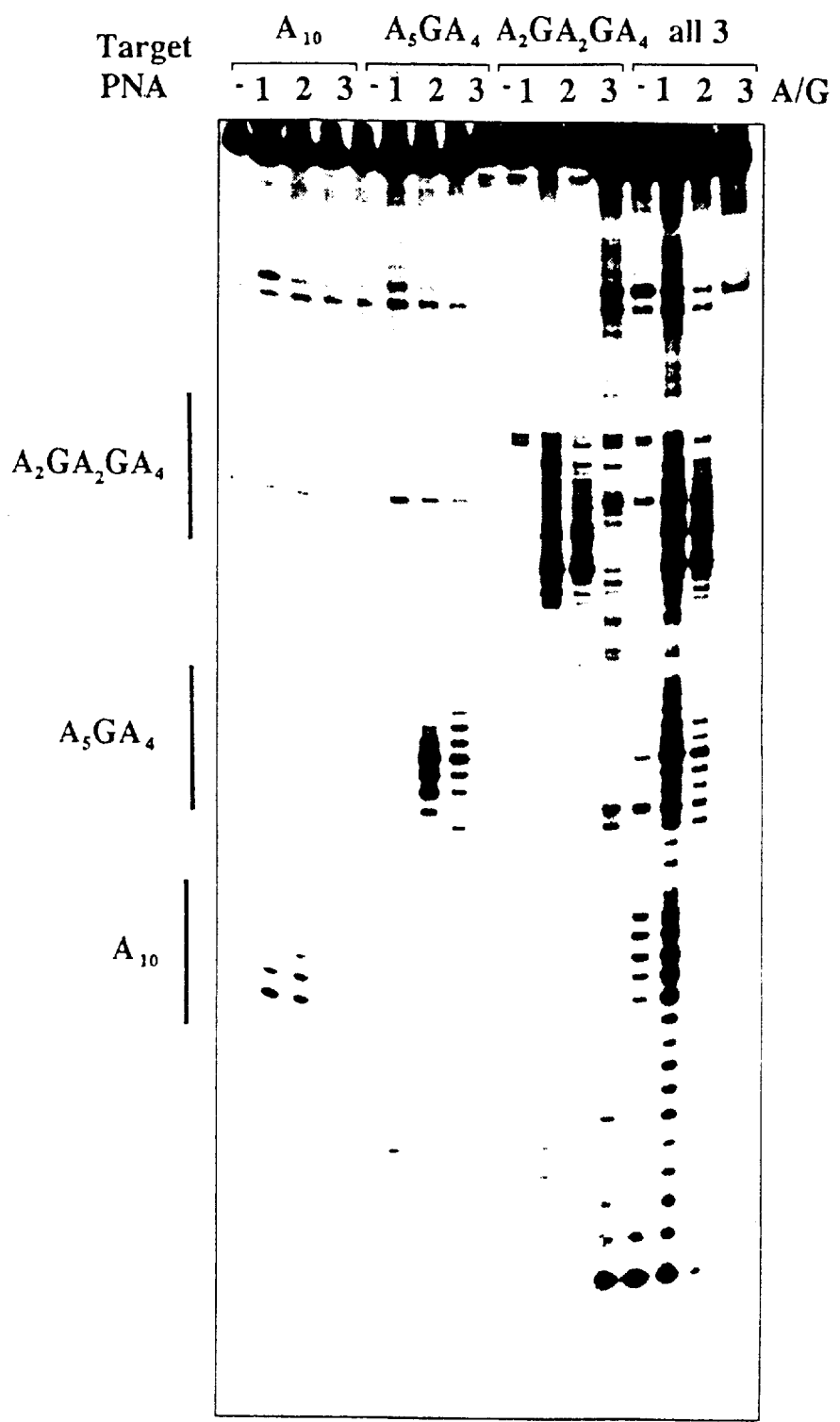
FIG. 20 shows a PAGE autoradiograph demonstrating that PNAs-$T_{10}$, -$T_9C$ and -$T_8C_2$ bind to double stranded DNA with high sequence specificity.

Binding of PNAs-T$_{10}$/T$_9$C/T$_8$C$_2$ to double stranded DNA targets A$_{10}$/A$_9$G/A$_8$G$_2$ (FIG. 20)

A mixture of 200 cps double stranded $^{32}$P-labeled EcoRI-PvuII fragment (the large fragment labeled at the 3'-end of the EcoRI site) of the indicated plasmid, 0.5 μg carrier calf thymus DNA, and 300 ng the indicated PNA in 100 μl buffer (200 mM NaCl, 50 mM Na-acetate, pH 4.5, 1 mM ZnSO$_4$) was incubated at 37° C. for 120 min. 50 units of nuclease S$_1$ were added and incubated at 20° C. for 5 min. The reaction was stopped by addition of 3 μl 0.5 M EDTA and the DNA was precipitated by addition of 250 μl 2% potassium acetate in ethanol. The DNA was analyzed by electrophoresis in 10% polyacrylamide sequencing gels and the radiolabelled DNA bands visualized by autoradiography. The complete band patterns produced show the production by strand displacement of single stranded DNA which is attacked by the nuclease to produce a mixture of shorter oligonucleotides. Comparison of the results for the three PNA's used in each case shows the selectivity for each target which is obtained.

The target plasmid were prepared by cloning of the appropriate oligonucleotides into pUC19. Target A$_{10}$: oligonucleotides GATCCA$_{10}$G & GATCCT$_{10}$G cloned into the BamHI site (plasmid designated pT10). Target A$_5$GA$_4$: oligonucleotides TCGACT$_4$CT$_5$G (See SEQ ID NO:29) & TCGACA$_5$GA$_4$G cloned into the SalI site (plasmid pT9C). Target A$_2$GA$_2$GA$_4$: oligonucleotides GA$_2$GA$_2$GA$_4$TGCA (See SEQ ID NO: 31) & GT$_4$CT$_2$CT$_2$CTGCA (See SEQ ID NO: 32) into the PstI site (plasmid pT8C2). The positions of the targets in the gel are indicated by bars to the left. A/G is an A+G sequence ladder of target P10.

EXAMPLE 64

Inhibition of restriction enzyme cleavage by PNA (FIG. 23)

A 2 μg portion of plasmid pT10 was mixed with the indicated amount of PNA-T$_{10}$ in 20 μl TE buffer (10 mM Tris-HCl, 1 mM EDTA, pH 7.4) and incubated at 37° C. for 120 min. 2 μl 10×concentrated buffer (10 mM Tris-HCl, pH 7.5, 10 mM, MgCl$_2$, 50 mM NaCl, 1 mM DTT) and PvuII (2 units) and BamHI (2 units) were added and the incubation was continued for 60 min. The DNA was analyzed by gel electrophoresis in 5% polyacrylamide and the DNA was visualized by ethidium bromide staining.

In the presence of a significant proportion of PNA (0.2, 0.6), the cleavage pattern of enzyme Bam HI was changed indicating that the enzyme was inhibited by the presence of PNA alongside the cleavage site.

EXAMPLE 65

Kinetics of PNA-T$_{10}$-dsDNA strand displacement complex formation (FIG. 21)

A mixture of 200 cps double stranded $^{32}$P-labeled EcoRI-PvuII fragment of pT10 (the large fragment labeled at the 3'-end of the EcoRI site), 0.5 μg carrier calf thymus DNA, and 300 ng of PNA-T$_{10}$-LysNH$_2$ in 100 μl buffer (200 mM NaCl, 50 mM Na-acetate, pH 4.5, 1 mM ZnSO$_4$) were incubated at 37° C. At the times indicated, 50 U of S$_1$ nuclease was added to each of 7 samples and incubation was continued for 5 min at 20° C. Any single stranded DNA produced by strand displacement is digested by the nuclease. The DNA was then precipitated by addition of 250 μl 2% potassium acetate in ethanol and analyzed by electrophoresis in a 10% polyacrylamide sequencing gel. The amount of strand displacement complex was calculated in arbitrary units from the intensity of the S$_1$-cleavage at the target sequence, as measured by densitometric scanning of autoradiographs. The formation of the complex over time can be seen.

EXAMPLE 66

Figure 22:
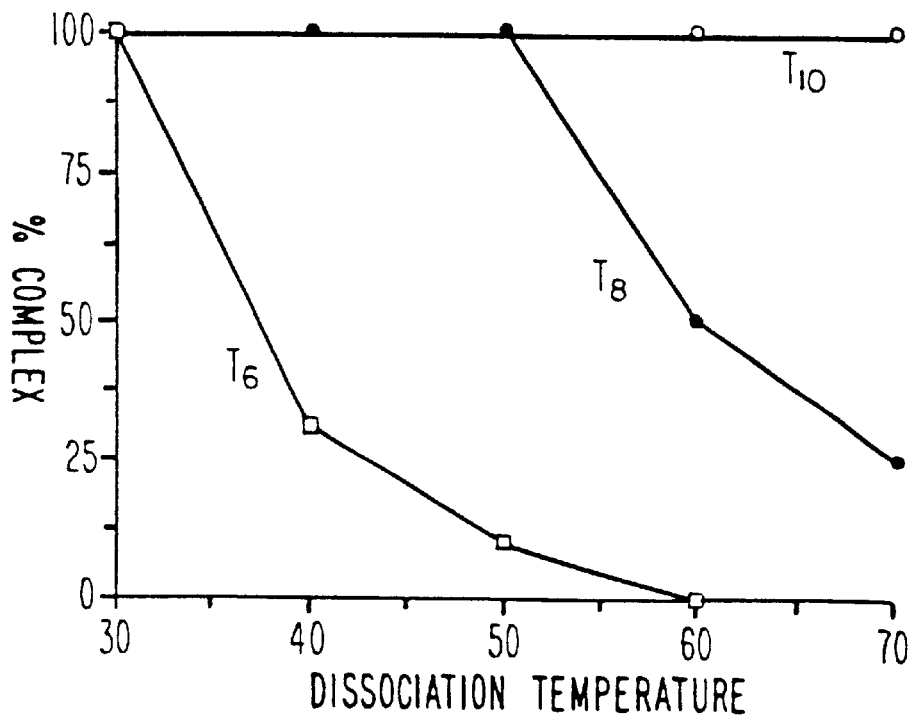
FIG. 22 shows a graph based on densitometric scanning of PAGE autoradiographs demonstrating the thermal stabilities of PNAs of varying lengths bound to an $A_{10}/T_{10}$ double stranded DNA target.

Stability of PNA-dsDNA complexes (FIG. 22)

A mixture of 200 cps $^{32}$P-pT10 fragment (as in Example 65), 0.5 μg calf thymus DNA and 300 ng of the desired PNA (either $T_{10}$-LysNH$_2$, $T_8$-LysNH$_2$ or $T_6$-LysNH$_2$) was incubated in 100 µl 200 mM NaCl, 50 mM Na-acetate, pH 4.5, 1 mM ZnSO$_4$ for 60 min at 37° C. A 2 µg portion of oligonucleotide GATCCA$_{10}$G was added to compete with the PNA for the labelled oligonucleotide and each sample was heated for 10 min at the temperature indicated, cooled in ice for 10 min and warmed to 20° C. 50 U of S$_1$ nuclease was added and the quantity of radio-activity liberated as single nucleotides was measured.

The expected $T_m$ values for a $T_{10}$ DNA duplex would be 20° C., for $T_8$—16° C., and for $T_6$—12° C. The corresponding PNA/DNA values are shown to be $T_{10}$>70° C., $T_8$—60° C., and for $T_6$—37° C.

EXAMPLE 67

Immobilisation of pNA

For the preparation of PNA-Sepharose 10 mg of cyanogen bromide activated Sepharose (Sigma) was incubated with 10 µg PNA in 100 µl 50 mM Na-phosphate, pH 7.5 for 60 min at 37° C. The Sepharose was isolated by centrifugation and washed three times with 250 µl 50 mM Na-phosphate, pH 7.5.

EXAMPLE 68

Binding of 5'-$^{32}$P-endlabeled oligonucleotide to PNA-Sepharose 1 mg PNA-Sepharose (Example 67) in 100 µl TE was incubated with 50 cps (~100 ng) P-labeled oligonucleotide for 16 hr at 20° C. The Sepharose was isolated by centrifugation and washed two times with 500 µl TE. Bound oligonucleotide was determined by liquid scintillation counting using the "Cerenkov" method. Results are shown in the Table below for three different PNA-Sepharose and four oligo-DNA's. The specificity of the capture by the immobilised PNA's is clearly seen, only one base pair mismatch being tolerated.

| % Binding of $^{32}$P-oligo to PNA-Sepharose PNA on solid support (CNBr-Sepharose) | | | | |
|---|---|---|---|---|
|  | T10 | T9C | T8C2 | none |
| DNA |  |  |  |  |
| A10 | 51 | 45 | 15 | 8 |
| A9G | 11 | 50 | 52 | 8 |
| A8G2 | 11 | 45 | 42 | 4 |
| mix | 11 | 13 | 14 | 15 |

In the table A10 is 5'-GATCCAAAAAAAAAAG, A9G is 5'-TCGACAAAAAGAAAAG (See SEQ ID NO:30), A8G2 is 5'-GAAGAAGAAACTGAC (See SEQ ID NO:33) & mix is 5'-GATCACGCGTATACGCGT (See SEQ ID NO:34). The PNAs are: T10: H-T$_{10}$LysNH$_2$, T9C: H-T$_5$CT$_4$-LysNH$_2$, T8C2: H-T$_2$CT$_2$CT$_4$-LysNH$_2$, none:ethanolamine.

Figure 25A:
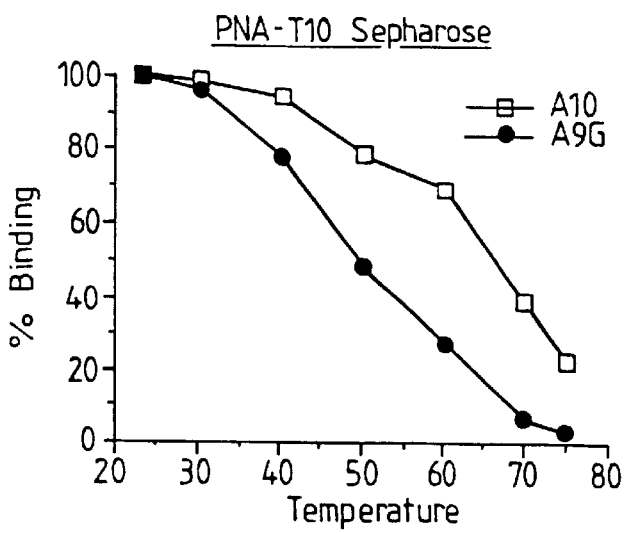
FIGS. 25a to c show the percentage binding achieved at varying temperatures between an immobilised PNA and matching or one base mismatched oligo-DNAs.
Figure 25B:
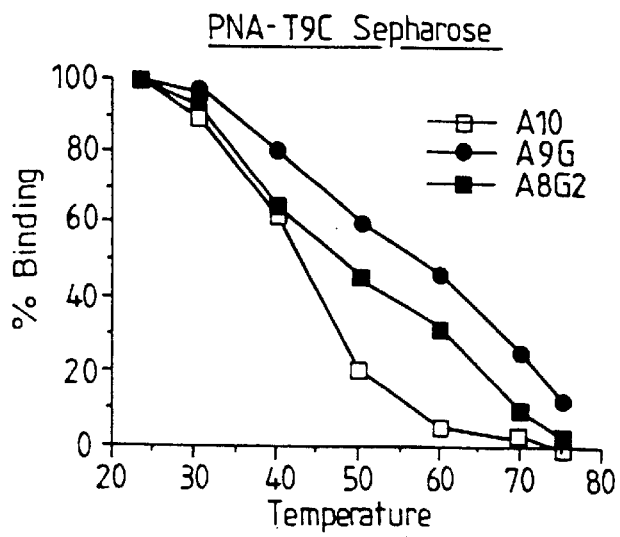
Figure 25C:
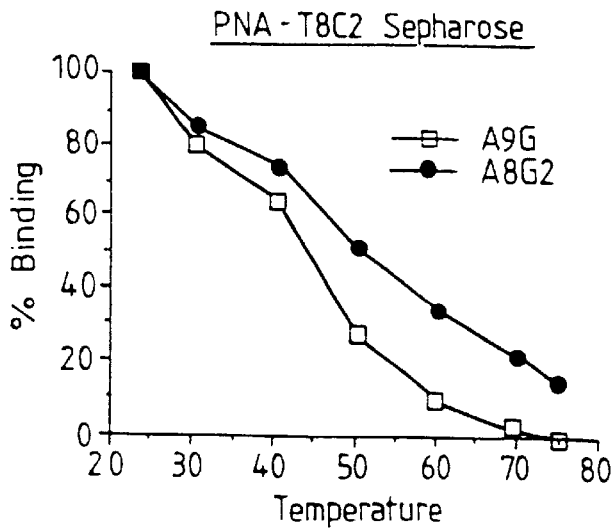

EXAMPLE 69 (FIGS. 25a, b & c)

Temperature dependence of stability of $^{32}$P-oligonucleotide-binding to PNA-Sepharose Oligonucleotides were bound to PNA-Sepharose as described in Examples 67 and 68. In each case, the $^{32}$P-oligonucleotide-PNA-Sepharose was subsequently washed at increasing temperatures. The Sepharose was isolated by centrifugation, the radioactivity determined by "Cerenkov" counting, and the Sepharose was again taken up in 500 µl TE, incubated at the next desired temperature, centrifuged etc. The figure shows the results normalised to initial binding. The oligonucleotide and PNA-Sepharose were as described in the Table of Example 68. The shifts between the curves show the lowered stability of the oligonucleotide binding when one mismatch is present.

EXAMPLE 70

Inhibition of Transcription by PNA (FIG. 26)

A mixture of 100 ng plasmid DNA (cleaved with restriction enzyme PvuII (see below) and 100 ng of PNA in 15 µl 10 mM Tris-HCl, 1 mM EDTA, pH 7.4 was incubated at 37° C. for 60 min. Subsequently, 4 µl 5×concentrated buffer (0.2 M Tris-HCl (pH 8.0), 40 mM MgCl$_2$, 10 mM spermidine, 125 mM NaCl) were mixed with 1 µl NTP-mix (10 mM ATP, 10 mM CTP, 10 mM GTP, 1 mM UTP, 0.1 µCi/µl $^{32}$P-UTP, 5 mM DTT, 2 µg/ml tRNA, 1 µg/ml heparin) and 3 units RNA polymerase. Incubation was continued for 10 min at 37° C. The RNA was then precipitated by addition of 60 µl 2% potassium acetate in 96% ethanol at −20° C. and analyzed by electrophoresis in 8% polyacrylamide sequencing gels. RNA transcripts were visualized by autoradiography. The plasmid used was: Lane 1 to 5; pA10KS (the A$_{10}$ target is positioned on the transcribed strand). Lane 6 to 10: pT10KS (the A$_{10}$ target is positioned on the non-transcribed strand). The plasmid was treated with the following restriction enzymes prior to the experiment: Lanes 1, 4, 6 and 9: PyuII; lanes 2, 5, 7 and 10: Xha I; lanes 3 and 8: BamHI. The samples of lanes 4, 5, 9 and 10 contained PNA, while the rest did not. It can be seen from the gel that when PNA T$_{10}$ is bound to the transcribed strand of the plasmid, transcription of RNA is arrested at the PNA binding site. If the PNA is bound to the non-transcribed strand of the plasmid, transcription is not arrested.

EXAMPLE 71

Figure 27:
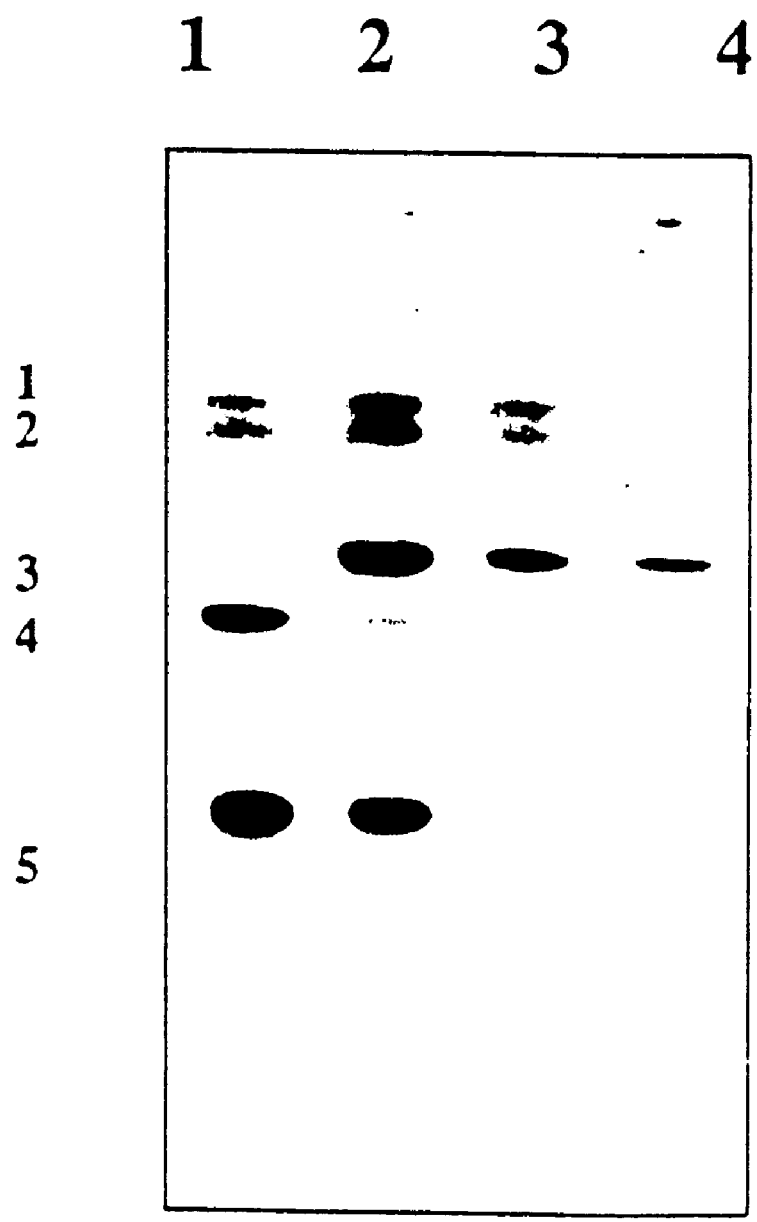
FIG. 27 is an autoradiograph of a mixture of labelled plasmid dsDNA's captured on an immobilised complementary to one of them and washed at varying temperatures.

Affinity PNA—Sepharose (FIG. 27)

1 mg of PNA-T$_{10}$ Sepharose (see Example 67) in 100 µl TE was incubated with ~50 cps of the following 32P-5'-endlabelled oligonucleotides:

1: 5'-GAT CCG GCA AAT CGG CAA TAC GGC ATA ACG GCT AAA CGG CTT TAC GGC TTA TCG GCT ATT CGG CAT TTC GGC AAT TCG (See SEQ ID NO:35),

2: 5'-GAT CCG GCT TAA CGG CAA TTC GCT TAT ACG GCA TAT CGG CTA ATC GGC ATT ACG GCT TTT CGG G (See SEQ ID:36),

3: 5'-GAC AAA CAT ACA ATT TCA ACA GAA CCA AAA AAA AAA AAA A (See SEQ ID NO:37),

4: 5'-ACT GAC TAC CTA GGT TTA CCC TGC CAG TCA (See SEQ ID NO:38),

5: 5'-GAA ACG GAT AGC TGC A (See SEQ ID NO:39), for 16 hrs at 20° C. The Sepharose was isolated by centrifugation and washed 3 times with TE. Oligonucleotides were subsequently washed off with 500 µl TE at increasing temperatures, precipitated with I ml ethanol, 2% potassium acetate and analysed by electrophoresis in 20% polyacrylamide, 7 M urea gel run in TBE buffer and detected by autoradiography (−70° C., 16 hrs. intensifying screen). The results are shown in FIG. 26. The lanes are as follows:

Lane 1: oligonucleotides not bound to the Sephadex;

Lane 2: oligonucleotides washed off at 40° C.;

Lane 3: oligonucleotides washed off at 60° C.;

Lane 4: oligonucleotides washed off at 80° C.

Only plasmid 3 is complementary to the PNA. It can be seen that by washing at up to 80° C. essentially only the complementary plasmid is retained on the PNA-Sepharose. This example illustrates the extraction of an oligonucleotide from a mixture thereof by affinity capture using PNA.

EXAMPLE 72

Quantitative assay of a DNA sequence in a ds plasmid by pNA-strand displacement

Figure 28:
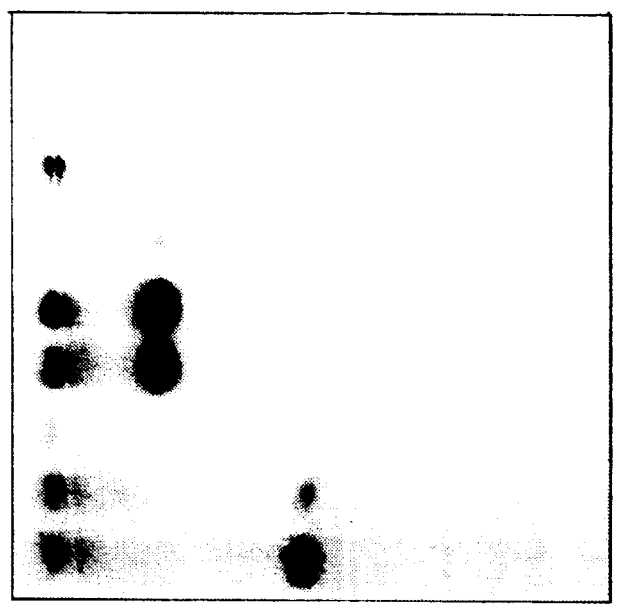
FIG. 28 combines an ethidium bromide gel and an autoradiograph thereof illustrating the quantitative determination of plasmid dsDNA by strand displacement by PNA.
Figure 28:
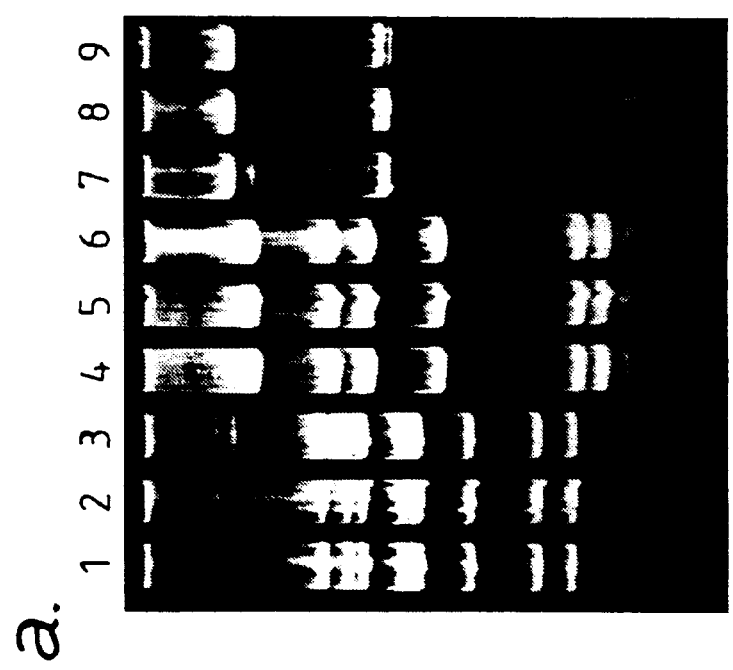

3 µg plasmid DNA digested by the respective restriction enzymes indicated below in 10 µl 50 mM Tris-HCl, 1 mM EDTA, pH 7.4 was incubated with 5000 cpm (~10 ng) $^{125}$I-PNA-$T_{10}$-Tyr and the quantity of cold PNA $T_{10}$Tyr indicated by the total PNA amounts given below for 60 mins at 37° C. The DNA was precipitated with 25 µl ethanol, 2% potassium acetate, and subsequently analysed by electrophoresis in 6% polyacrylamide in TBE buffer. The gel was stained with ethidium bromide and subsequently subject to autoradiography (–70° C., 16 hrs intensifying screen). The results are seen in FIG. 28. "A" is the ethidium stained gel and "b" is the corresponding autoradiogram. The plasmids used were:

Lanes 1 to 3: $pT_{10}$+HaeIII;

Lanes 4 to 6: $pT_{10}$×Hinfl;

Lanes 7 to 9: $pT_{10}$×PvuII.

The total amount of PNA-$T_{10}$-Tyr in each sample was:

Lanes 1, 4 and 7: ~10 ng;

Lanes 2, 5 and 8: 25 ng;

Lanes 3, 6 and 9: 250 ng.

The ethidium bromide gel (a) shows the size of the DNA fragments produced (including DNA-PNA hybrids). The autoradograph (b) shows which band in gel (a) contains PNA. The presence of a strand displacement complex can be seen in lane 1 as can the effect on the intensity of this band of increasing the proportion of cold PNA in lanes 2 and 3. Similar results are seen for each of the other two plasmids in lanes 4 to 6 and 7 to 9. The location of the PNA-DNA band in each case can be used to identify the plasmid and the based intensity can be used to quantitate the amount of plasmid present.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

---

What is claimed is:

1. A method of capturing a nucleic acid comprising contacting under hybridising conditions said nucleic acid with a nucleic acid analogue selected from the group consisting of:
   (a) a peptide nucleic acid (PNA) comprising a polyamide backbone bearing a plurality of ligands at respective spaced locations along said backbone, said ligands being each independently naturally occurring nucleobases, non-naturally occurring nucleobases or nucleobase-binding groups, each said ligand being bound directly or indirectly to a nitrogen atom in said backbone, and said ligand bearing nitrogen atoms mainly being separated from one another in said backbone by from 4 to 8 intervening atoms;
   (b) a nucleic acid analogue containing a peptide nucleic acid (PNA) capable of hybridizing to a nucleic acid of complementary sequence to form a hybrid which is more stable against denaturation by heat than a hybrid between the conventional deoxyribonucleotide corresponding to said analogue and said nucleic acid; and
   (c) a nucleic acid analogue containing a peptide nucleic acid (PNA) capable of hybridizing to a double stranded nucleic acid in which one strand has a sequence complementary to said analogue, so as to displace the other strand from said one strand;
immobilised to a solid support, which nucleic acid analogue has a sequence of ligands suitable to hybridise to said nucleic acid.

2. A method as claimed in claim 1, wherein said captured nucleic acid is detected, recognised, quantitated or identified by treatment with a nucleic acid recognition agent whilst bound to said immobilised nucleic acid analogue.

3. A method as claimed in claim 2, wherein the captured nucleic acid has a first region hybridised to said immobilised nucleic acid analogue and a second region which is not so hybridised and is treated with a labelled nucleic acid or nucleic acid analogue which is adapted to hybridise to at least part of said second region and said label is detected.

4. A method as claimed in claim 1, for capturing a mRNA wherein said immobilised nucleic acid analogue comprises sequential ligands hybridisable to poly A tails of said mRNA to capture said mRNA.

5. A method as claimed in claim 4, wherein said sequential ligands are thymine.

6. A method as claimed in claim 1 wherein said nucleic acid once captured is released from said immobilized nucleic acid analogue by subjecting the immobilized nucleic acid analogue and captured nucleic acid to dehybridizing conditions.

7. A method of recognition, detection or quantitation of a target nucleic acid comprising hybridising said target to a labelled nucleic acid analogue of sufficiently complementary sequence to hybridise therewith under hybridising conditions and detecting or quantitating said label of the nucleic acid analogue so hybridised to said target, said nucleic acid analogue selected from the group consisting of:
   (a) a peptide nucleic acid (PNA) comprising a polyamide backbone bearing a plurality of ligands at respective spaced locations along said backbone, said ligands being each independently naturally occurring nucleobases, non-naturally occurring nucleobases or nucleobase-binding groups, each said ligand being bound directly or indirectly to a nitrogen atom in said backbone, and said ligand bearing nitrogen atoms mainly being separated from one another in said backbone by from 4 to 8 intervening atoms;
   (b) a nucleic acid analogue containing a peptide nucleic acid (PNA) capable of hybridizing to a nucleic acid of complementary sequence to form a hybrid which is more stable against denaturation by heat than a hybrid between the conventional deoxyribonucleotide corresponding to said analogue and said nucleic acid; and
   (c) a nucleic acid analogue containing a peptide nucleic acid (PNA) capable of hybridizing to a double stranded nucleic acid in which one strand has a sequence complementary to said analogue, so as to displace the other strand from said one strand.

8. A method as claimed in claim 7, wherein said target nucleic acid is immobilised on a substrate prior to said hybridisation.

9. A method as claimed in claim 8, wherein said target nucleic acid is immobilised to said substrate by the hybridisation of a first region thereof to a capture nucleic acid or nucleic acid analogue having a sequence sufficiently complementary to said first region to hybridise therewith and which is itself immobilised to said substrate and wherein said labelled nucleic acid analogue hybridises to a second region of said target.

10. A method for displacing one strand of a nucleic acid duplex comprising hybridizing to said duplex a nucleic acid analogue containing a peptide nucleic acid (PNA) having an affinity for the other strand of said duplex sufficient to be able to displace said one strand therefrom.

11. A method of detecting, identifying or quantitating a double stranded target nucleic acid comprising hybridising thereto a displacing nucleic acid analogue capable of displacing one strand from a double stranded target in which the other strand is of complementary sequence to said displacing nucleic acid analogue, wherein said displacing nucleic acid analogue is of sufficiently complementary sequence to said other strand of said double stranded target to hybridise thereto so as to displace said one strand of said target in single stranded form, and detecting or quantitating the presence of said one displaced strand as a detection, identification or quantitation of said double stranded target nucleic acid.

12. A method as claimed in claim 11, wherein the displaced strand is broken down into fragments and the presence of said fragments is detected.

13. A method as claimed in claim 12, wherein said displaced strand is broken down by attack by a nuclease.

14. A method for the recognition, detection, identification or quantification of a nucleic acid, comprising hybridizing the nucleic acid and a nucleic acid analogue which analogue is selected from the group consisting of
   (a) a peptide nucleic acid (PNA) comprising a polyamide backbone bearing a plurality of ligands at respective spaced locations along said backbone, said ligands being each independently naturally occurring nucleobases, non-naturally occurring nucleobases or nucleobase-binding groups, each said ligand being bound directly or indirectly to a nitrogen atom in said backbone, and said ligand bearing nitrogen atoms mainly being separated from one another in said backbone by from 4 to 8 intervening atoms;
   (b) a nucleic acid analogue containing a peptide nucleic acid (PNA) capable of hybridizing to a nucleic acid of complementary sequence to form a hybrid which is more stable against denaturation by heat than a hybrid between the conventional deoxyribonucleotide corresponding to said analogue and said nucleic acid; and
   (c) a nucleic acid analogue containing a peptide nucleic acid (PNA) capable of hybridizing to a double stranded nucleic acid in which one strand has a sequence complementary to said analogue, so as to displace the other strand from said one strand; and recognizing, detecting, identifying or quantitating the hybrid so formed.

15. A method as claimed in claim 14, wherein said analogue is said PNA and said ligand bearing nitrogen atoms in said PNA backbone are each aza nitrogen atoms.

* * * * *